US011317909B2

(12) United States Patent
Whitman et al.

(10) Patent No.: US 11,317,909 B2
(45) Date of Patent: May 3, 2022

(54) SURGICAL DEVICE HAVING MULTIPLE DRIVERS

(71) Applicant: Covidien LP, Mansfield, MA (US)

(72) Inventors: Michael P. Whitman, New Hope, PA (US); Donald Malinouskas, Monroe, CT (US); Peter Datcuk, Quakerstown, PA (US); David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 292 days.

(21) Appl. No.: 16/570,193

(22) Filed: Sep. 13, 2019

(65) Prior Publication Data

US 2020/0000463 A1     Jan. 2, 2020

Related U.S. Application Data

(60) Continuation of application No. 15/053,335, filed on Feb. 25, 2016, now Pat. No. 10,420,548, which is a
(Continued)

(51) Int. Cl.
*A61B 17/068*     (2006.01)
*A61B 17/072*     (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ........ A61B 2017/00398; A61B 17/072; A61B 17/07207; A61B 17/068;
(Continued)

(56) References Cited

U.S. PATENT DOCUMENTS

| 1,881,706 A | 2/1931 | Larsen |
| 1,798,902 A | 3/1931 | Raney |

(Continued)

FOREIGN PATENT DOCUMENTS

| CA | 2473512 A1 | 1/2005 |
| CN | 101779876 A | 7/2010 |

(Continued)

OTHER PUBLICATIONS

EP Search Report for corresponding EP08831651 dated Oct. 21, 2010 (3 pages).

(Continued)

*Primary Examiner* — Robert F Long
*Assistant Examiner* — Xavier A Madison
(74) *Attorney, Agent, or Firm* — Carter, DeLuca & Farrell LLP

(57) ABSTRACT

A surgical device is provided, the surgical device including a first driver for performing a first movement function; a second driver for performing a second movement function; a first rotatable drive shaft configured, upon actuation, to cause selective engagement of one of the first and second drivers with a second rotatable drive shaft, wherein the second rotatable drive shaft is configured to drive the selectively engaged one of the first and second drivers. Third and fourth drivers may also be included. The drivers may function to rotate a shaft portion of the surgical device relative to, and about the longitudinal axis of, a handle; move a jaw portion relative to the shaft portion; move a first jaw relative to a second jaw; and/or move a surgical member within the second jaw.

12 Claims, 39 Drawing Sheets

Related U.S. Application Data continuation of application No. 14/694,204, filed on Apr. 23, 2015, now Pat. No. 9,282,961, which is a division of application No. 12/235,362, filed on Sep. 22, 2008, now Pat. No. 7,963,433.

(60) Provisional application No. 60/974,267, filed on Sep. 21, 2007.

(51) Int. Cl.
*A61B 90/98* (2016.01)
*A61B 17/00* (2006.01)
*A61B 17/29* (2006.01)

(52) U.S. Cl.
CPC .... *A61B 90/98* (2016.02); *A61B 2017/00398* (2013.01); *A61B 2017/00464* (2013.01); *A61B 2017/00734* (2013.01); *A61B 2017/07214* (2013.01); *A61B 2017/2923* (2013.01); *A61B 2017/2926* (2013.01); *A61B 2017/2943* (2013.01)

(58) Field of Classification Search
CPC ........... A61B 2017/00734; A61B 2017/07214; A61B 2017/2923; A61B 2017/2926; A61B 2017/2943
USPC ............................................ 227/175.1–182.1
See application file for complete search history.

(56) References Cited

U.S. PATENT DOCUMENTS

| | | |
|---|---|---|
| 1,881,250 A | 10/1932 | Tomlinson |
| 2,031,682 A | 2/1936 | Wappler et al. |
| 2,226,789 A | 11/1938 | Tupy |
| 2,229,800 A | 3/1939 | Dean |
| 2,174,219 A | 9/1939 | Balma |
| 2,246,647 A | 6/1941 | Vancura |
| 2,355,086 A | 10/1943 | Lang |
| 2,419,045 A | 4/1947 | Whittaker |
| 2,725,628 A | 12/1955 | O'Neilly et al. |
| 3,017,637 A | 1/1962 | Sampson |
| 3,079,606 A | 3/1963 | Bobrov et al. |
| 3,120,845 A | 2/1964 | Horner |
| 3,193,165 A | 7/1965 | Akhalaya et al. |
| 3,252,643 A | 5/1966 | Strekopov et al. |
| 3,252,880 A | 5/1966 | Magat |
| 3,253,643 A | 5/1966 | Gudheim |
| 3,256,875 A | 6/1966 | Tsepelev et al. |
| 3,269,631 A | 8/1966 | Takaro |
| 3,275,211 A | 9/1966 | Hirsch et al. |
| 3,315,863 A | 4/1967 | O'Dea |
| 3,317,105 A | 5/1967 | Astafjev et al. |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green et al. |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles |
| 3,858,577 A | 1/1975 | Bass et al. |
| 3,859,986 A | 1/1975 | Okada et al. |
| 3,879,104 A | 4/1975 | Shugarman et al. |
| 3,882,854 A | 5/1975 | Hulka et al. |
| 3,892,228 A | 7/1975 | Mitsui |
| 3,902,614 A | 9/1975 | Roberts et al. |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 3,985,050 A | 10/1976 | Lurie |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,261,244 A | 4/1981 | Becht et al. |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,354,628 A | 10/1982 | Green |
| 4,360,110 A | 11/1982 | Sigman et al. |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,484,775 A | 11/1984 | Norkus |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,534,420 A | 8/1985 | Goldelius |

(56) References Cited

U.S. PATENT DOCUMENTS

| | | |
|---|---|---|
| 4,535,773 A | 8/1985 | Yoon |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,573,727 A | 3/1986 | Iikura |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,600,357 A | 7/1986 | Coules |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| D286,567 S | 11/1986 | Lichtman et al. |
| 4,623,183 A | 11/1986 | Aomori |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,676,542 A | 6/1987 | Besold |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |
| 4,728,020 A | 3/1988 | Green et al. |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,784,422 A | 11/1988 | Jones et al. |
| 4,789,090 A | 12/1988 | Blake, III |
| 4,790,225 A | 12/1988 | Moody et al. |
| 4,796,793 A | 1/1989 | Smith et al. |
| 4,805,823 A | 2/1989 | Rothfuss |
| 4,815,469 A | 3/1989 | Cohen et al. |
| 4,817,847 A | 4/1989 | Redtenbacher et al. |
| 4,819,632 A | 4/1989 | Davies |
| 4,819,853 A | 4/1989 | Green |
| 4,841,888 A | 6/1989 | Mills et al. |
| 4,848,637 A | 7/1989 | Pruitt |
| 4,858,608 A | 8/1989 | McQuilkin |
| 4,863,088 A | 9/1989 | Redmond et al. |
| 4,867,158 A | 9/1989 | Sugg |
| 4,869,415 A | 9/1989 | Fox |
| 4,873,977 A | 10/1989 | Avant et al. |
| 4,887,599 A | 12/1989 | Muller |
| 4,887,612 A | 12/1989 | Esser et al. |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,907,973 A | 3/1990 | Hon |
| 4,917,114 A | 4/1990 | Green et al. |
| 4,919,152 A | 4/1990 | Ger |
| 4,928,699 A | 5/1990 | Sasai |
| 4,930,494 A | 6/1990 | Takehana et al. |
| 4,932,960 A | 6/1990 | Green et al. |
| 4,936,845 A | 6/1990 | Stevens |
| 4,941,454 A | 7/1990 | Wood et al. |
| 4,941,623 A | 7/1990 | Pruitt |
| 4,944,093 A | 7/1990 | Falk |
| 4,944,443 A | 7/1990 | Oddsen et al. |
| 4,955,882 A | 9/1990 | Hakky |
| 4,955,959 A | 9/1990 | Tompkins et al. |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,977,900 A | 12/1990 | Fehling et al. |
| 4,978,049 A | 12/1990 | Green |
| 4,982,726 A | 1/1991 | Taira |
| 4,991,764 A | 2/1991 | Mericle |
| 4,994,060 A | 2/1991 | Rink et al. |
| 4,995,877 A | 2/1991 | Ams et al. |
| 5,005,749 A | 4/1991 | Aranyi |
| 5,018,657 A | 5/1991 | Pedlick et al. |
| 5,031,814 A | 7/1991 | Tompkins et al. |
| 5,040,715 A | 8/1991 | Green et al. |
| 5,059,203 A | 10/1991 | Husted |
| 5,065,929 A | 11/1991 | Schulze et al. |
| D322,143 S | 12/1991 | Spreckelmeier |
| 5,071,430 A | 12/1991 | de Salis et al. |
| 5,077,506 A | 12/1991 | Krause |
| 5,100,041 A | 3/1992 | Storace |
| 5,104,025 A | 4/1992 | Main et al. |
| 5,108,391 A | 4/1992 | Flachenecker et al. |
| 5,114,065 A | 5/1992 | Storace |
| 5,119,983 A | 6/1992 | Green et al. |
| 5,129,570 A | 7/1992 | Schulze et al. |
| 5,133,359 A | 7/1992 | Kedem |
| 5,133,713 A | 7/1992 | Huang et al. |
| 5,133,729 A | 7/1992 | Sjostrom |
| 5,139,513 A | 8/1992 | Segato |
| 5,156,315 A | 10/1992 | Green et al. |
| 5,157,837 A | 10/1992 | Rose |
| 5,158,222 A | 10/1992 | Green et al. |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,192,292 A | 3/1993 | Cezana et al. |
| 5,197,649 A | 3/1993 | Bessler et al. |
| 5,201,325 A | 4/1993 | McEwen et al. |
| 5,201,501 A | 4/1993 | Fassler |
| 5,201,750 A | 4/1993 | Hocherl et al. |
| 5,205,459 A | 4/1993 | Brinkerhoff et al. |
| 5,207,691 A | 5/1993 | Nardella |
| 5,207,697 A | 5/1993 | Carusillo et al. |
| 5,217,003 A | 6/1993 | Wilk |
| 5,217,460 A | 6/1993 | Knoepfler |
| 5,221,279 A | 6/1993 | Cook et al. |
| 5,224,951 A | 7/1993 | Freitas |
| 5,226,426 A | 7/1993 | Yoon |
| 5,237,884 A | 8/1993 | Seto |
| 5,243,967 A | 9/1993 | Hibino |
| 5,249,583 A | 10/1993 | Mallaby |
| 5,253,793 A | 10/1993 | Green et al. |
| 5,254,117 A | 10/1993 | Rigby et al. |
| 5,258,004 A | 11/1993 | Bales et al. |
| 5,258,007 A | 11/1993 | Spetzler et al. |
| 5,258,008 A | 11/1993 | Wilk |
| 5,261,877 A | 11/1993 | Fine et al. |

(56) References Cited

U.S. PATENT DOCUMENTS

| | | |
|---|---|---|
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,609 A | 1/1994 | Pingleton et al. |
| 5,279,565 A | 1/1994 | Klein et al. |
| 5,285,945 A | 2/1994 | Brinkerhoff et al. |
| 5,289,963 A | 3/1994 | McGarry et al. |
| 5,290,299 A | 3/1994 | Fain et al. |
| 5,290,303 A | 3/1994 | Pingleton et al. |
| 5,292,053 A | 3/1994 | Bilotti et al. |
| 5,295,990 A | 3/1994 | Levin |
| 5,300,087 A | 4/1994 | Knoepfler |
| 5,307,976 A | 5/1994 | Olson et al. |
| 5,312,023 A | 5/1994 | Green et al. |
| 5,312,434 A | 5/1994 | Crainich |
| 5,318,221 A | 6/1994 | Green et al. |
| 5,320,627 A | 6/1994 | Sorensen et al. |
| 5,322,055 A | 6/1994 | Davison et al. |
| 5,324,288 A | 6/1994 | Billings et al. |
| 5,324,300 A | 6/1994 | Elias et al. |
| 5,326,013 A | 7/1994 | Green et al. |
| 5,330,471 A | 7/1994 | Eggers |
| 5,330,486 A | 7/1994 | Wilk |
| 5,333,772 A | 8/1994 | Rothfuss et al. |
| 5,333,773 A | 8/1994 | Main et al. |
| 5,336,229 A | 8/1994 | Noda |
| 5,342,299 A | 8/1994 | Snoke et al. |
| 5,342,381 A | 8/1994 | Tidemand |
| 5,342,382 A | 8/1994 | Brinkerhoff et al. |
| 5,344,420 A | 9/1994 | Hilal et al. |
| 5,350,104 A | 9/1994 | Main et al. |
| 5,352,222 A | 10/1994 | Rydell |
| 5,352,223 A | 10/1994 | McBrayer et al. |
| 5,352,235 A | 10/1994 | Koros et al. |
| 5,354,266 A | 10/1994 | Snoke |
| 5,356,408 A | 10/1994 | Rydell |
| 5,358,506 A | 10/1994 | Green et al. |
| 5,364,001 A | 11/1994 | Bryan |
| 5,364,409 A | 11/1994 | Kuwabara et al. |
| 5,366,133 A | 11/1994 | Geiste |
| 5,366,476 A | 11/1994 | Noda |
| 5,368,015 A | 11/1994 | Wilk |
| 5,368,607 A | 11/1994 | Freitas |
| 5,370,294 A | 12/1994 | Bauer |
| 5,380,321 A | 1/1995 | Yoon |
| 5,383,880 A | 1/1995 | Hooven |
| 5,389,098 A | 2/1995 | Tsuruta et al. |
| 5,391,156 A | 2/1995 | Hildwein et al. |
| 5,392,789 A | 2/1995 | Slater et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| 5,400,267 A | 3/1995 | Denen et al. |
| D357,535 S | 4/1995 | Grant et al. |
| 5,403,312 A | 4/1995 | Fates et al. |
| 5,403,326 A | 4/1995 | Harrison et al. |
| 5,403,327 A | 4/1995 | Thornton et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,425,705 A | 6/1995 | Evard et al. |
| 5,425,738 A | 6/1995 | Gustafson et al. |
| 5,425,745 A | 6/1995 | Green et al. |
| 5,431,322 A | 7/1995 | Green et al. |
| 5,431,645 A | 7/1995 | Smith et al. |
| 5,433,721 A | 7/1995 | Hooven et al. |
| 5,437,636 A | 8/1995 | Snoke et al. |
| 5,441,507 A | 8/1995 | Wilk |
| 5,443,198 A | 8/1995 | Viola et al. |
| 5,447,265 A | 9/1995 | Vidal et al. |
| 5,454,825 A | 10/1995 | Van Leeuwen et al. |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,465,895 A | 11/1995 | Knodel et al. |
| 5,467,911 A | 11/1995 | Tsuruta et al. |
| 5,472,132 A | 12/1995 | Savage et al. |
| 5,474,223 A | 12/1995 | Viola et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,487,499 A | 1/1996 | Sorrentino et al. |
| 5,487,500 A | 1/1996 | Knodel et al. |
| 5,496,269 A | 3/1996 | Snoke |
| 5,496,317 A | 3/1996 | Goble et al. |
| 5,496,333 A | 3/1996 | Sackier et al. |
| 5,514,134 A | 5/1996 | Rydell et al. |
| 5,518,163 A | 5/1996 | Hooven |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,529,235 A | 6/1996 | Boiarski et al. |
| 5,531,687 A | 7/1996 | Snoke et al. |
| 5,533,661 A | 7/1996 | Main et al. |
| 5,535,935 A | 7/1996 | Vidal et al. |
| 5,535,937 A | 7/1996 | Boiarski et al. |
| 5,549,565 A | 8/1996 | Ryan et al. |
| 5,553,765 A | 9/1996 | Knodel et al. |
| 5,554,169 A | 9/1996 | Green et al. |
| 5,562,677 A | 10/1996 | Hildwein et al. |
| 5,562,702 A | 10/1996 | Huitema et al. |
| 5,569,274 A | 10/1996 | Rapacki et al. |
| 5,571,116 A | 11/1996 | Bolanos et al. |
| 5,573,543 A | 11/1996 | Akopov et al. |
| 5,575,799 A | 11/1996 | Bolanos et al. |
| 5,578,052 A | 11/1996 | Koros et al. |
| 5,580,067 A | 12/1996 | Hamblin et al. |
| 5,582,611 A | 12/1996 | Tsuruta et al. |
| 5,584,425 A | 12/1996 | Savage et al. |
| 5,588,579 A | 12/1996 | Schnut et al. |
| 5,591,186 A | 1/1997 | Wurster et al. |
| 5,597,107 A | 1/1997 | Knodel et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,609,381 A | 3/1997 | Thom et al. |
| 5,609,560 A | 3/1997 | Ichikawa et al. |
| 5,618,303 A | 4/1997 | Marlow et al. |
| 5,618,307 A | 4/1997 | Donlon et al. |
| 5,626,607 A | 5/1997 | Malecki et al. |
| 5,628,446 A | 5/1997 | Geiste et al. |
| 5,639,008 A | 6/1997 | Gallagher et al. |
| 5,651,780 A | 7/1997 | Jackson et al. |
| 5,653,374 A | 8/1997 | Young et al. |
| 5,665,100 A | 9/1997 | Yoon |
| 5,667,473 A | 9/1997 | Finn et al. |
| 5,667,478 A | 9/1997 | McFarlin et al. |
| 5,667,517 A | 9/1997 | Hooven |
| 5,667,526 A | 9/1997 | Levin |
| 5,676,674 A | 10/1997 | Bolanos et al. |
| 5,688,269 A | 11/1997 | Newton et al. |
| 5,692,668 A | 12/1997 | Schulze et al. |
| 5,693,031 A | 12/1997 | Ryan et al. |
| 5,697,542 A | 12/1997 | Knodel et al. |
| 5,709,335 A | 1/1998 | Heck |
| 5,732,871 A | 3/1998 | Clark et al. |
| 5,732,872 A | 3/1998 | Bolduc et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,893 A | 5/1998 | Vidal et al. |
| 5,752,644 A | 5/1998 | Bolanos et al. |

(56) References Cited

U.S. PATENT DOCUMENTS

| | | |
|---|---|---|
| 5,758,814 A | 6/1998 | Gallagher et al. |
| 5,762,458 A | 6/1998 | Wang et al. |
| 5,776,147 A | 7/1998 | Dolendo |
| 5,779,130 A | 7/1998 | Alesi et al. |
| 5,779,132 A | 7/1998 | Knodel et al. |
| 5,782,396 A | 7/1998 | Mastri et al. |
| 5,782,397 A | 7/1998 | Koukline |
| 5,792,135 A | 8/1998 | Madhani et al. |
| 5,797,835 A | 8/1998 | Green |
| 5,797,900 A | 8/1998 | Madhani et al. |
| 5,797,944 A | 8/1998 | Nobles et al. |
| 5,807,377 A | 9/1998 | Madhani et al. |
| 5,807,402 A | 9/1998 | Yoon |
| 5,814,044 A | 9/1998 | Hooven |
| 5,815,640 A | 9/1998 | Wang et al. |
| 5,817,113 A | 10/1998 | Gifford, III et al. |
| 5,820,009 A | 10/1998 | Melling et al. |
| 5,823,956 A | 10/1998 | Roth et al. |
| 5,826,776 A | 10/1998 | Schulze et al. |
| 5,829,662 A | 11/1998 | Allen et al. |
| 5,836,503 A | 11/1998 | Ehrenfels et al. |
| 5,846,221 A | 12/1998 | Snoke et al. |
| 5,855,583 A | 1/1999 | Wang et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,871,471 A | 2/1999 | Ryan et al. |
| 5,878,193 A | 3/1999 | Wang et al. |
| 5,881,943 A | 3/1999 | Heck et al. |
| 5,893,553 A | 4/1999 | Pinkous |
| 5,893,875 A | 4/1999 | O'Connor et al. |
| 5,895,084 A | 4/1999 | Mauro |
| 5,897,562 A | 4/1999 | Bolanos et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A | 9/1999 | Viola et al. |
| 5,954,731 A | 9/1999 | Yoon |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,989,274 A | 11/1999 | Davison et al. |
| 5,993,378 A | 11/1999 | Lemelson |
| 5,993,454 A | 11/1999 | Longo |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,162,220 A | 12/2000 | Nezhat |
| 6,165,191 A | 12/2000 | Shibata et al. |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,244,809 B1 | 6/2001 | Wang et al. |
| 6,246,200 B1 | 6/2001 | Blumenkranz et al. |
| D444,555 S | 7/2001 | Cooper et al. |
| 6,264,087 B1 | 7/2001 | Whitman |
| 6,302,311 B1 | 10/2001 | Adams et al. |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 6,716,233 B1 | 4/2004 | Whitman |
| 6,790,217 B2 | 9/2004 | Schulze et al. |
| 6,793,652 B1 | 9/2004 | Whitman et al. |
| 6,981,941 B2 | 1/2006 | Whitman et al. |
| 7,032,798 B2 | 4/2006 | Whitman et al. |
| 7,114,642 B2 | 10/2006 | Whitman |
| 7,464,849 B2 | 12/2008 | Shelton, IV et al. |
| 7,568,603 B2 | 8/2009 | Shelton, IV et al. |
| 7,708,182 B2 | 5/2010 | Viola |
| 7,963,433 B2 | 6/2011 | Whitman et al. |
| 8,623,276 B2 | 1/2014 | Schmaltz et al. |
| 8,968,276 B2 | 3/2015 | Zemlok et al. |
| 9,282,961 B2 | 3/2016 | Whitman et al. |
| 2001/0016750 A1 | 8/2001 | Malecki et al. |
| 2001/0031975 A1 | 10/2001 | Whitman et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0072736 A1 | 6/2002 | Tierney et al. |
| 2002/0165444 A1 | 11/2002 | Whitman |
| 2002/0198554 A1 | 12/2002 | Whitman et al. |
| 2003/0077769 A1 | 4/2003 | Smallridge et al. |
| 2003/0105478 A1 | 6/2003 | Whitman et al. |
| 2003/0130677 A1 | 7/2003 | Whitman et al. |
| 2004/0094597 A1 | 5/2004 | Whitman et al. |
| 2005/0283140 A1* | 12/2005 | Jensen ............... B25J 15/04<br>606/1 |
| 2007/0023477 A1 | 2/2007 | Whitman et al. |
| 2009/0236399 A1* | 9/2009 | Bilotti .............. A61B 17/072<br>227/180.1 |
| 2011/0174099 A1 | 7/2011 | Ross et al. |

FOREIGN PATENT DOCUMENTS

| | | |
|---|---|---|
| CN | 102459038 A | 5/2012 |
| DE | 2330182 A1 | 1/1975 |
| DE | 2903159 A1 | 7/1980 |
| DE | 3114135 A1 | 10/1982 |
| DE | 3300768 A1 | 7/1984 |
| DE | 4213426 A1 | 10/1992 |
| DE | 4312147 A1 | 10/1993 |

(56) References Cited

FOREIGN PATENT DOCUMENTS

| | | |
|---|---|---|
| EP | 0041022 A1 | 12/1981 |
| EP | 0116220 A1 | 8/1984 |
| EP | 0121474 A2 | 10/1984 |
| EP | 0142225 A1 | 5/1985 |
| EP | 0156774 A2 | 10/1985 |
| EP | 0203375 A2 | 12/1986 |
| EP | 0216532 A1 | 4/1987 |
| EP | 0293123 A2 | 11/1988 |
| EP | 0324166 A2 | 7/1989 |
| EP | 0324637 A1 | 7/1989 |
| EP | 0365153 A1 | 4/1990 |
| EP | 0369324 A1 | 5/1990 |
| EP | 0373762 A1 | 6/1990 |
| EP | 0399701 A1 | 11/1990 |
| EP | 0484677 A1 | 5/1992 |
| EP | 0514139 A2 | 11/1992 |
| EP | 0536903 A2 | 4/1993 |
| EP | 0539762 A1 | 5/1993 |
| EP | 0552050 A2 | 7/1993 |
| EP | 0552423 A2 | 7/1993 |
| EP | 0581400 A1 | 2/1994 |
| EP | 0593920 A1 | 4/1994 |
| EP | 0598579 A1 | 5/1994 |
| EP | 0621006 A1 | 10/1994 |
| EP | 0630612 A1 | 12/1994 |
| EP | 0634144 A1 | 1/1995 |
| EP | 0639349 A2 | 2/1995 |
| EP | 0653922 A1 | 5/1995 |
| EP | 0679367 A2 | 11/1995 |
| EP | 0705571 A1 | 4/1996 |
| EP | 0878169 A1 | 11/1998 |
| EP | 0947167 A1 | 10/1999 |
| EP | 1872727 A1 | 1/2008 |
| EP | 2027819 A1 | 2/2009 |
| FR | 2660851 A1 | 10/1991 |
| GB | 1082821 A | 9/1967 |
| GB | 1352554 A | 5/1974 |
| GB | 1452185 A | 10/1976 |
| GB | 2044108 A | 10/1980 |
| GB | 2048685 A | 12/1980 |
| GB | 2165559 A | 4/1986 |
| GB | 2180455 A | 4/1987 |
| JP | 2003500153 A | 1/2003 |
| JP | 2008114339 A | 5/2008 |
| JP | 2010518985 A | 6/2010 |
| NL | 7711347 A | 4/1979 |
| RU | 659146 | 4/1979 |
| WO | 8203545 A1 | 10/1982 |
| WO | 8300992 A1 | 3/1983 |
| WO | 9005489 A1 | 5/1990 |
| WO | 9005491 A2 | 5/1990 |
| WO | 9006085 A1 | 6/1990 |
| WO | 9107136 A1 | 5/1991 |
| WO | 9216141 A1 | 10/1992 |
| WO | 9308754 A1 | 5/1993 |
| WO | 9314706 A1 | 8/1993 |
| WO | 9518572 A1 | 7/1995 |
| WO | 9535065 A1 | 12/1995 |
| WO | 9712555 A2 | 4/1997 |
| WO | 9814129 A1 | 4/1998 |
| WO | 9920328 A2 | 4/1999 |
| WO | 9958076 A1 | 11/1999 |
| WO | 0072765 A1 | 12/2000 |
| WO | 0103587 A1 | 1/2001 |
| WO | 0108572 A1 | 2/2001 |
| WO | 0117448 | 3/2001 |
| WO | 0135813 A1 | 5/2001 |
| WO | 0162163 A1 | 8/2001 |
| WO | 02058539 A2 | 8/2002 |
| WO | 03077769 A1 | 9/2003 |
| WO | 2007016290 A2 | 2/2007 |
| WO | 2008103797 A2 | 8/2008 |

OTHER PUBLICATIONS

International Search Report corresponding to PCT Application No. PCT/US2006/029287, completed Jun. 25, 2007 and dated Aug. 27, 2007; 1 page.
European Communication under Rule 71(3) EPC dated Mar. 24, 2015 for European Patent Appln. No. EP 10 010 188.0.
Canadian Office Action for CA 2,698,571 dated May 4, 2015.
Japanese Office Action dated Jun. 19, 2015 for Japanese Appln. No. JP 2014-132135.
Canadian Office Action and Summary for Candian Appln. No. 2,698,571 dated Oct. 16, 2015.
Japanese Notice of Allowance for JP 2014-132135 dated Jul. 12, 2016.
European Search Report EP 16 18 4170 dated Dec. 1, 2016.
Canadian Office Action dated Mar. 16, 2017 issued in corresponding Canadian Application No. 2,473,512.
European Search Report dated Apr. 6, 2017 issued in corresponding European Application No. 12197970.2.
Notice of Allowance dated Oct. 16, 2017 issued in corresponding Japanese Application No. 2013-112661 (JPO Communication Summary Form attached).
Japanese Notice of Allowance dated Nov. 13, 2017 issued in corresponding JP Application No. 2015-166403.
Japanese Notice of Allowance dated Nov. 13, 2017 issued in corresponding JP Application No. 2015-166403 (Summary only).
Japanese Office Action dated Jan. 25, 2017 issued in corresponding Japanese Patent Application No. 2015-166403.
Japanese Office Action dated Jun. 23, 2017 issued in corresponding Japanese Application No. 2015-166403.

\* cited by examiner

SURGICAL DEVICE HAVING MULTIPLE DRIVERS

CROSS-REFERENCE TO RELATED APPLICATIONS

The present application is a continuation of U.S. patent application Ser. No. 15/053,335, filed Feb. 25, 2016, which is a continuation of U.S. patent application Ser. No. 14/694,204, filed Apr. 23, 2015, now U.S. Pat. No. 9,282,961, which is a divisional of U.S. patent application Ser. No. 12/235,362, filed Sep. 22, 2008, now U.S. Pat. No. 7,963,433, which claims benefit and priority to U.S. Provisional Patent Application No. 60/974,267, filed on Sep. 21, 2007. The entire contents of all of the foregoing applications are expressly incorporated by reference herein.

INCORPORATION BY REFERENCE

The present application expressly incorporates herein by reference each of the following in its entirety: U.S. patent application Ser. No. 11/191,851, filed on Jul. 27, 2005, and Issued as U.S. Pat. No. 8,241,322 on Aug. 14, 2012; U.S. patent application Ser. No. 10/460,291, filed on Jun. 11, 2003, and Issued as U.S. Pat. No. 7,743,960 on Jun. 29, 2010; U.S. patent application Ser. No. 10/099,634, filed on Mar. 15, 2002, and Issued as U.S. Pat. No. 7,951,071 on May 31, 2011; U.S. patent application Ser. No. 09/999,546, filed on Nov. 30, 2001, and Issued as U.S. Pat. No. 7,695,485 on Apr. 13, 2010; U.S. patent application Ser. No. 09/887,789, filed on Jun. 22, 2001, and Issued as U.S. Pat. No. 7,032,798 on Apr. 25, 2006; U.S. patent application Ser. No. 09/836,781, filed on Apr. 17, 2001, and Issued as U.S. Pat. No. 6,981,941 on Jan. 3, 2006; U.S. patent application Ser. No. 09/723,715, filed on Nov. 28, 2000, and Issued as U.S. Pat. No. 6,793,652 on Sep. 21, 2004; U.S. patent application Ser. No. 09/324,451, filed on Jun. 2, 1999, and Issued as U.S. Pat. No. 6,315,184 on Nov. 13, 2001; U.S. patent application Ser. No. 09/324,452, filed on Jun. 2, 1999, and Issued as U.S. Pat. No. 6,443,973 on Sep. 3, 2002; U.S. patent application Ser. No. 09/351,534, filed on Jul. 12, 1999 and Issued as U.S. Pat. No. 6,264,087 on Jul. 24, 2001; U.S. patent application Ser. No. 09/510,923, filed on Feb. 22, 2000 and Issued as U.S. Pat. No. 6,517,565 on Feb. 11, 2003; and U.S. patent application Ser. No. 09/510,927, filed on Feb. 22, 2000 and Issued as U.S. Pat. No. 6,716,233 on Apr. 6, 2004.

FIELD OF THE INVENTION

The present invention relates to a surgical device. More specifically, the present invention relates to a powered, rotating and/or articulating device for clamping, cutting and stapling tissue.

BACKGROUND INFORMATION

One type of surgical device is a linear clamping, cutting and stapling device. Such a device may be employed in a surgical procedure to resect a cancerous or anomalous tissue from a gastro-intestinal tract. One conventional linear clamping, cutting and stapling instrument is shown in FIG. 1. The device includes a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

One problem with the foregoing surgical devices, and in particular with the foregoing linear clamping, cutting and stapling devices such as that illustrated in FIG. 1, is that the opposing jaws may be difficult to maneuver within a patient. It may be necessary for a surgeon to move the opposing jaws between various angles in order to position the desired tissue between the opposing jaws. However, it is also generally desirable to make an incision in a patient that is as small as possible, and the small size of an incision limits the degree to which the opposing jaws may be maneuvered.

Another problem with the foregoing surgical devices, and in particular with the foregoing linear clamping, cutting and stapling devices such as that illustrated in FIG. 1, is that the opposing jaws may not be sufficiently hemostatic. Specifically, the opposing jaws of the foregoing surgical devices are not clamped together with sufficient force, thereby reducing the effectiveness of the surgical device. Still another problem with the foregoing surgical devices, and in particular with the foregoing linear clamping, cutting and stapling devices such as that illustrated in FIG. 1, is that the cutting and/or stapling members are not driven with sufficient torque, thereby reducing the effectiveness of the surgical device.

Thus, there is believed to be a need for an improvement in the maneuverability of clamping, cutting and stapling devices. In addition, there is believed to be a need for a clamping, cutting and stapling device that provides additional clamping, cutting and stapling forces.

SUMMARY

In accordance with an example embodiment of the present invention, a surgical device is provided, the surgical device including a first driver for performing a first movement function; a second driver for performing a second movement function; a first rotatable drive shaft configured, upon actuation, to cause selective engagement of one of the first and second drivers with a second rotatable drive shaft, wherein the second rotatable drive shaft is configured to drive the selectively engaged one of the first and second drivers.

In an embodiment, the surgical device also includes a third driver for performing a third movement function, wherein the first rotatable drive shaft is configured, upon actuation, to cause selective engagement of one of the first, second and third drivers with a second rotatable drive shaft, and wherein the second rotatable drive shaft is configured to drive the selectively engaged one of the first, second and third drivers. Also, the surgical device may include a fourth driver for performing a third movement function, wherein the first rotatable drive shaft is configured, upon actuation, to cause selective engagement of one of the first, second, third and fourth drivers with a second rotatable drive shaft, and wherein the second rotatable drive shaft is configured to drive the selectively engaged one of the first, second, third and fourth drivers.

Various movement functions may be performed by the surgical device. For example, the surgical device may include a shaft portion coupled to a handle, the handle defining a longitudinal axis. At least one of the first and second movement functions may include rotating, upon actuation of the second rotatable drive shaft, a shaft portion of the surgical device relative to, and about a longitudinal axis of, a handle of the surgical device. Actuation of the second rotatable drive shaft in a first rotational direction may cause pivotal movement of the shaft portion in a first rotational direction relative to, and about the longitudinal axis of, the handle, and actuation of the second rotatable drive shaft in a second rotational direction may cause pivotal movement of the shaft portion in a second rotational direction that is opposite the first rotational direction relative to, and about the longitudinal axis of, the handle. The first or second driver may include at least one gear that is selectively engaged by the second rotatable drive shaft upon the first rotatable drive shaft moving a functional component into a position corresponding to the at least one of the first and second movement functions.

In another movement function that may be performed by the surgical device, the surgical device may include a jaw portion coupled to a shaft portion, and the first or second movement function may include moving, upon actuation of the second rotatable drive shaft, a jaw portion of the surgical device relative to a shaft portion of the surgical device. Actuation of the second rotatable drive shaft in a first rotational direction may cause pivotal movement of the jaw portion in a first rotational direction relative to the shaft portion, and actuation of the second rotatable drive shaft in a second rotational direction may cause pivotal movement of the jaw portion in a second rotational direction that is opposite the first rotational direction relative to the shaft portion. The jaw portion and the shaft portion may define respective longitudinal axes, and the jaw portion may pivot relative to a shaft portion about a longitudinal axis that is perpendicular to the longitudinal axes of the jaw portion and the shaft portion. The first or second driver may include at least one gear that is selectively engaged by the second rotatable drive shaft upon the first rotatable drive shaft moving a functional component into a position corresponding to the at least one of the first and second movement functions.

In another movement function that may be performed by the surgical device, the surgical device may include a jaw portion that includes a first jaw and a second jaw in opposed correspondence with each other, and the first or second movement function may include moving, upon actuation of the second rotatable drive shaft, the first jaw relative to the second jaw. Actuation of the second rotatable drive shaft in a first rotational direction may cause movement of the first jaw in a first rotational direction relative to the second jaw, and actuation of the second rotatable drive shaft in a second rotational direction may cause pivotal movement of the first jaw in a second rotational direction that is opposite the first rotational direction relative to the second jaw. The first or second jaws may define respective longitudinal axes, and the first jaw may pivot relative to the second jaw about a longitudinal axis that is perpendicular to the longitudinal axes of the first and second jaws. The first or second driver may include at least one gear that is selectively engaged by the second rotatable drive shaft upon the first rotatable drive shaft moving a functional component into a position corresponding to the at least one of the first and second movement functions.

In another movement function that may be performed by the surgical device, the surgical device may include a first jaw and a second jaw in opposed correspondence with the first jaw, the second jaw including a surgical member. At least one of the first and second movement functions may include driving, upon actuation of the second rotatable drive shaft, the surgical member within the second jaw. Actuation of the second rotatable drive shaft in a first rotational direction may cause movement of the surgical member in a first direction within the second jaw, and actuation of the second rotatable drive shaft in a second rotational direction may cause movement of the surgical member in a second direction that is opposite the first direction within the second jaw. The surgical member may include at least one of a cutting element and a stapling element. The first or second drivers may include at least one gear that is selectively engaged by the second rotatable drive shaft upon the first rotatable drive shaft moving a functional component into a position corresponding to the at least one of the first and second movement functions.

In an embodiment, the first and second rotatable drive shafts are coupleable to respective drive couplings of an electro-mechanical driver. Alternatively, the surgical device may also include at least one motor, the at least one motor configured to rotate the first and second rotatable drive shafts.

In another embodiment, there is provided a surgical system that includes an electro-mechanical driver unit including at least one motor unit, and a surgical attachment that includes: a first driver for performing a first movement function; a second driver for performing a second movement function; a first rotatable drive shaft coupleable to the at least one motor unit and configured, upon actuation by the at least one motor unit, to cause selective engagement of one of the first and second drivers with a second rotatable drive shaft, wherein the second rotatable drive shaft is coupleable to the at least one motor unit and is configured to drive the selectively engaged one of the first and second drivers via the at least one motor unit.

Also, the surgical attachment of the surgical system may further include a third driver for performing a third movement function, wherein the first rotatable drive shaft is configured, upon actuation, to cause selective engagement of one of the first, second and third drivers with the second rotatable drive shaft, and wherein the second rotatable drive shaft is configured to drive the selectively engaged one of the first, second and third drivers. In addition, the surgical attachment may also include a fourth driver for performing a third movement function, wherein the first rotatable drive shaft is configured, upon actuation, to cause selective engagement of one of the first, second, third and fourth drivers with the second rotatable drive shaft, and wherein the second rotatable drive shaft is configured to drive the selectively engaged one of the first, second, third and fourth drivers.

In an embodiment, the surgical attachment of the surgical system includes a shaft portion coupled to a handle, the handle defining a longitudinal axis, wherein at least one of the first and second movement functions includes rotating, upon actuation of the second rotatable drive shaft, a shaft portion of the surgical device relative to, and about a longitudinal axis of, a handle of the surgical device. Actuation via the at least one motor unit of the second rotatable drive shaft in a first rotational direction may cause pivotal movement of the shaft portion in a first rotational direction relative to, and about the longitudinal axis of, the handle, and actuation via the at least one motor unit of the second rotatable drive shaft in a second rotational direction may cause pivotal movement of the shaft portion in a second rotational direction that is opposite the first rotational direction relative to, and about the longitudinal axis of, the handle. The first or second driver may include at least one gear that is selectively engaged by the second rotatable drive shaft upon the first rotatable drive shaft moving a functional component into a position corresponding to the at least one of the first and second movement functions.

In an embodiment, the surgical attachment of the surgical system includes a jaw portion coupled to a shaft portion, wherein at least one of the first and second movement functions includes moving, upon actuation via the at least one motor unit of the second rotatable drive shaft, a jaw portion of the surgical device relative to a shaft portion of the surgical device. Actuation via the at least one motor unit of the second rotatable drive shaft in a first rotational direction may cause pivotal movement of the jaw portion in a first rotational direction relative to the shaft portion, and actuation via the at least one motor unit of the second rotatable drive shaft in a second rotational direction may cause pivotal movement of the jaw portion in a second rotational direction that is opposite the first rotational direction relative to the shaft portion. The jaw portion and the shaft portion may define respective longitudinal axes, and the jaw portion may pivot relative to a shaft portion about a longitudinal axis that is perpendicular to the longitudinal axes of the jaw portion and the shaft portion. The first or second driver may include at least one gear that is selectively engaged by the second rotatable drive shaft upon the first rotatable drive shaft moving a functional component into a position corresponding to the at least one of the first and second movement functions.

In an embodiment, the surgical attachment of the surgical system may include a jaw portion that includes a first jaw and a second jaw in opposed correspondence with each other, and the first or second movement function may include moving, upon actuation via the at least one motor unit of the second rotatable drive shaft, the first jaw relative to the second jaw. Actuation via the at least one motor unit of the second rotatable drive shaft in a first rotational direction may cause movement of the first jaw in a first rotational direction relative to the second jaw, and actuation via the at least one motor unit of the second rotatable drive shaft in a second rotational direction may cause pivotal movement of the first jaw in a second rotational direction that is opposite the first rotational direction relative to the second jaw. The first and second jaws define respective longitudinal axes, and the first jaw may pivot relative to the second jaw about a longitudinal axis that is perpendicular to the longitudinal axes of the first and second jaws. The first or second driver may include at least one gear that is selectively engaged by the second rotatable drive shaft upon the first rotatable drive shaft moving a functional component into a position corresponding to the at least one of the first and second movement functions.

In an embodiment, the surgical attachment of the surgical system includes a first jaw and a second jaw in opposed correspondence with the first jaw, the second jaw including a surgical member, wherein at least one of the first and second movement functions includes driving, upon actuation via the at least one motor unit of the second rotatable drive shaft, the surgical member within the second jaw. Actuation via the at least one motor unit of the second rotatable drive shaft in a first rotational direction may cause movement of the surgical member in a first direction within the second jaw, and actuation via the at least one motor unit of the second rotatable drive shaft in a second rotational direction may cause movement of the surgical member in a second direction that is opposite the first direction within the second jaw. The surgical member may include at least one of a cutting element and a stapling element. The first or second driver may include at least one gear that is selectively engaged by the second rotatable drive shaft upon the first rotatable drive shaft moving a functional component into a position corresponding to the at least one of the first and second movement functions.

In an embodiment, the surgical system of the surgical system may also include a control system configured to control the motor unit. The control system may be disposed within a housing. Also, the control system may include at least one control device mounted on the surgical attachment, and the control device may include a wireless remote control unit. The surgical attachment may include a position sensor corresponding to a function component that is moveable by the first rotatable drive shaft, the sensor outputting a signal corresponding to a position of the function component. The second rotatable drive shaft may be configured to be selectively engaged with the first and/or second driver based on the position of the function component.

In another embodiment, a surgical device is provided which includes a jaw portion, having a first jaw in opposed correspondence with a second jaw, the second jaw including a surgical member, a shaft portion coupled to a proximal end of the jaw portion and a handle defining a longitudinal axis. The surgical device may also include a first driver for rotating the shaft portion of the surgical device relative to, and about the longitudinal axis of, the handle; a second driver for moving the jaw portion relative to the shaft portion; a third driver for moving the first jaw relative to the second jaw; and a fourth driver for moving the surgical member within the second jaw. In addition, the surgical device may also include a first rotatable drive shaft configured, upon actuation, to cause selective engagement of at least one of the first, second, third and fourth drivers with a second rotatable drive shaft, wherein the second rotatable drive shaft is configured to drive the selectively engaged one of the first, second, third and fourth drivers.

In such an embodiment, the surgical device may be arranged such that, upon the first rotatable drive shaft causing engagement of the first driver with the second rotatable drive shaft, actuation of the second rotatable drive shaft in a first rotational direction causes pivotal movement of the shaft portion in a first rotational direction relative to, and about the longitudinal axis of, the handle, and actuation of the second rotatable drive shaft in a second rotational direction causes pivotal movement of the shaft portion in a second rotational direction that is opposite the first rotational direction relative to, and about the longitudinal axis of, the handle. Also, the surgical device may be arranged such that, upon the first rotatable drive shaft causing engagement of the second driver with the second rotatable drive shaft, actuation of the second rotatable drive shaft in a first rotational direction causes pivotal movement of the jaw portion in a first rotational direction relative to the shaft portion, and actuation of the second rotatable drive shaft in a second rotational direction causes pivotal movement of the jaw portion in a second rotational direction that is opposite the first rotational direction relative to the shaft portion. Further, the surgical device may be arranged such that the jaw portion and the shaft portion define respective longitudinal axes, and wherein the jaw portion pivots relative to a shaft portion about a longitudinal axis that is perpendicular to the longitudinal axes of the jaw portion and the shaft portion.

The surgical device may also be arranged such that, upon the first rotatable drive shaft causing engagement of the third driver with the second rotatable drive shaft, actuation of the second rotatable drive shaft in a first rotational direction causes movement of the first jaw in a first rotational direction relative to the second jaw, and actuation of the second rotatable drive shaft in a second rotational direction causes pivotal movement of the first jaw in a second rotational direction that is opposite the first rotational direction relative to the second jaw. In such an arrangement, the first and second jaws may define respective longitudinal axes, and the first jaw may pivot relative to the second jaw about a longitudinal axis that is perpendicular to the longitudinal axes of the first and second jaws.

Also, the surgical device may be arranged such that, upon the first rotatable drive shaft causing engagement of the third driver with the second rotatable drive shaft, actuation of the second rotatable drive shaft in a first rotational direction causes movement of the surgical member in a first direction within the second jaw, and actuation of the second rotatable drive shaft in a second rotational direction causes movement of the surgical member in a second direction that is opposite the first direction within the second jaw.

In an embodiment, the first and second rotatable drive shafts may be coupleable to respective drive couplings of an electro-mechanical driver. Alternatively, the surgical device may include at least one motor, the at least one motor configured to rotate the first and second rotatable drive shafts.

DETAILED DESCRIPTION

Figure 2A:
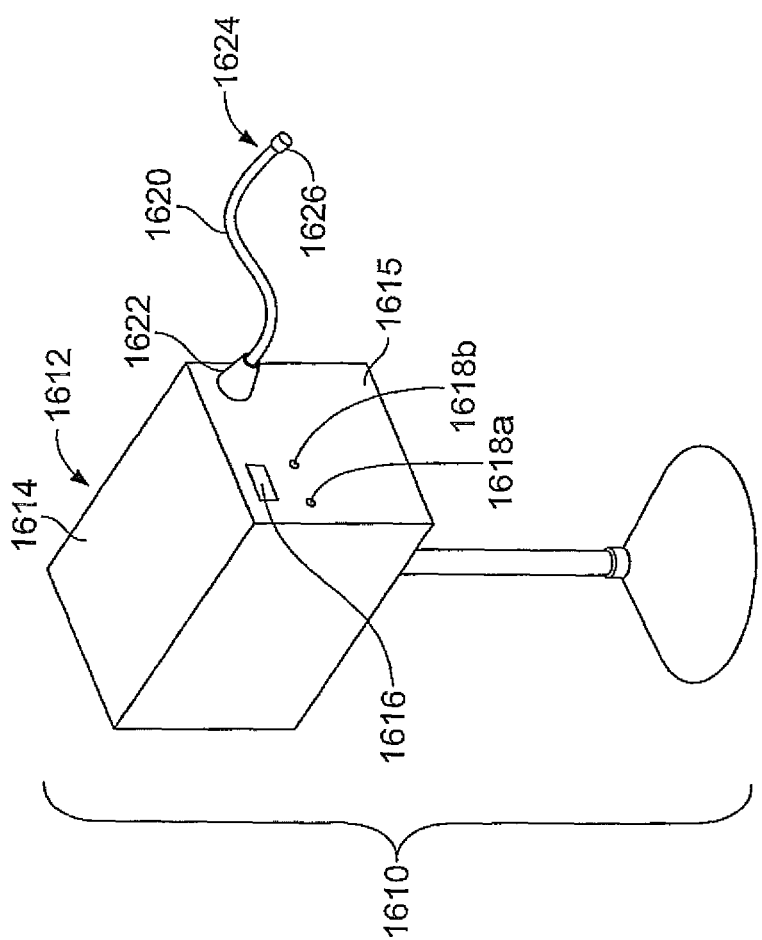
FIG. 2(a) is a perspective view of an example embodiment of an electro-mechanical driver component, according to the present invention.
Figure 2B:
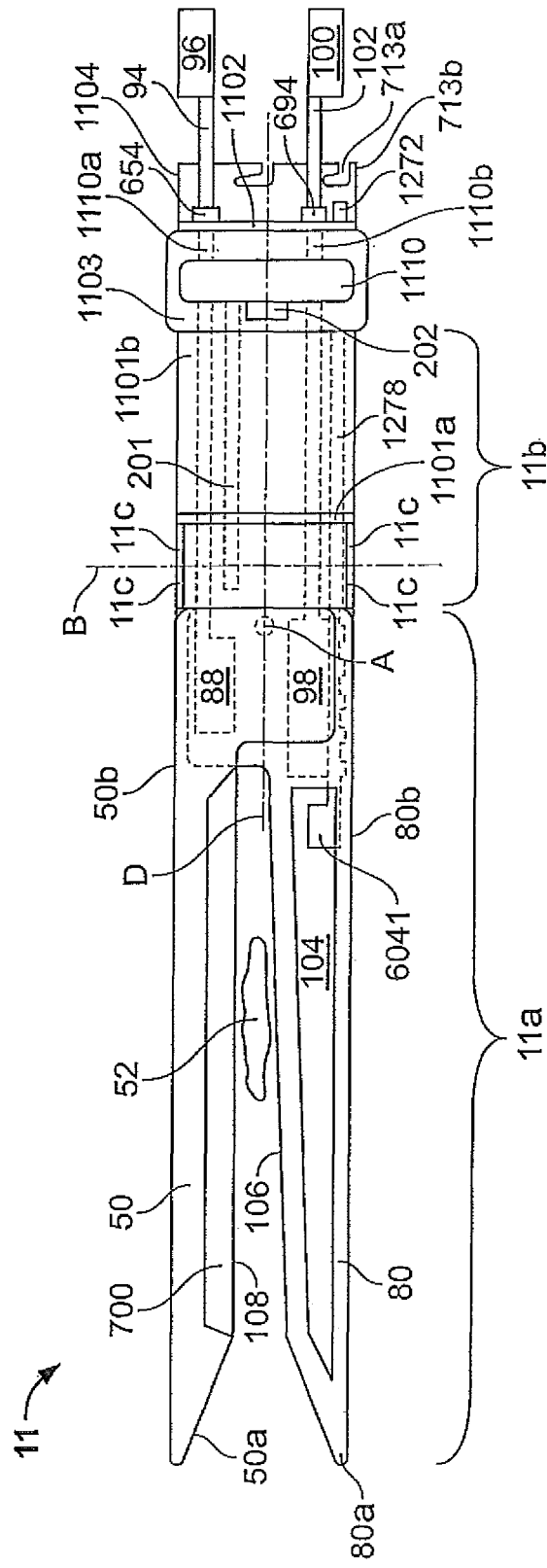
FIG. 2(b) is a schematic diagram that illustrates some of the components of a surgical device, according to an example embodiment of the present invention.

FIG. 2(b) is a schematic diagram that illustrates some of the components of a surgical device 11, according to an example embodiment of the present invention. The surgical device 11 is configured so as to be particularly well-suited for insertion into the body of a patient, e.g., via a cannula (not shown). In the embodiment shown, the surgical device 11 is a clamping, cutting and stapling device. The surgical device 11 includes a jaw portion 11a that is pivotably coupled to a shaft portion 11b by a hinge portion 11c. The jaw portion 11a includes a first jaw 50 having a distal end 50a and a proximal end 50b, and a second jaw 80 having a distal end 80a and a proximal end 80b. The first jaw 50 and the second jaw 80 are pivotably coupled relative to each other at or near their respective proximal ends 50b, 80b. As shown, the first jaw 50 and the second jaw 80 are pivotable relative to each other about pivot axis A. In the example embodiment shown, pivot axis A is oriented perpendicular to the page. In this arrangement, the jaws are configured such that, upon opening and closing of the first jaw 50 relative to the second jaw 80 and at point in the movement of the first jaw 50 relative to the second jaw 80, both the first jaw 50 and the second jaw 80, e.g., their longitudinal axes, remain within a plane defined by the page. It should be understood, however, that the surgical device 11 may instead be configured such that the first jaw 50 and the second jaw 80 are pivotable relative to each other about a pivot axis that is not oriented perpendicular to the page, in which case the first jaw 50 and the second jaw 80 may move within a plane or planes defined by other than the page.

As mentioned above, the jaw portion 11a is pivotably coupled to the shaft portion 11b by the hinge portion 11c. Specifically, the jaw portion 11a is pivotable relative to the shaft portion 11b about a pivot axis B, which may be positioned at any location on or between the jaw portion 11a and the shaft portion 11b, and at any circumferential location relative to the jaw portion 11a and the shaft portion 11b. In the example embodiment shown, the pivot axis B is oriented vertically, and within the page, in the view shown. In this arrangement, the jaw portion 11a and the shaft portion 11b are configured such that, upon articulation of the jaw portion 11a relative to the shaft portion 11b and at any point in the movement of the jaw portion 11a relative to the shaft portion 11b, the jaw portion 11a and the shaft portion 11b remain within a plane that is perpendicular to the pivot axis B. It should be recognized that, in other example embodiments, the pivot axis B may have a different orientation, so as to enable the jaw portion 11a to pivot within a different plane. The jaw portion 11a may be pivotable to and between any angles relative to the shaft portion 11b, such that the jaw portion 11a can be selectively positioned as desired during use.

Furthermore, the surgical device 11 may provide rotation of various components about a longitudinal axis of the surgical device 11. For example, in various embodiments, the jaw and/or shaft portions 11a, 11b may be rotatable relative to a handle 1103 (described in additional detail below), that is attached to a proximal end of the shaft portion 11b, about a longitudinal axis D of the handle 1103, e.g., the longitudinal axis D of the handle 1103 at the point where the handle 1103 meets the shaft portion 11b.

The shaft portion 11b may include a distal portion 1101a, to which the jaw portion 11a is connected, and a proximal portion 1101b, which may be connected to the handle 1103. For the purposes of clarity, the handle 1103 is shown in FIG. 2(b) schematically; further details of the handle 1103, according to various embodiments of the present invention, are set forth in connection with, e.g., FIGS. 5(a) through 5(d). Generally, the handle 1103 provides a device with which a user may grasp and operate the surgical device 11. The handle 1103 has a proximal portion 1102. At the proximal portion 1102, the handle 1103 may include a connection element 1104, e.g., a quick-connect coupling, for connecting to a flexible shaft (described in further detail below).

The second jaw 80 includes a clamping surface 106. The second jaw 80 also includes a cutting and stapling element 104, which may form at least part of the clamping surface 106 of the second jaw 80. The first jaw 50 includes an anvil member 700 in opposed correspondence with the second jaw 80. The anvil member 700 includes the clamping surface 108, which, along with the clamping surface 106 of the second jaw 80, clamps a section of tissue to be cut and stapled. As explained in greater detail below, the cutting and stapling element 104 is configured to cut and staple a section of tissue when the first jaw 50 and the second jaw 80 are in a closed, e.g., fully closed, position. Additional features of the cutting and stapling element 104, according to an embodiment, are illustrated and described, for instance, in connection with FIGS. 3(*f*) and 3(*g*) below, and further in U.S. patent application Ser. No. 09/999,546, filed Nov. 30, 2001 (now U.S. Pat. No. 7,695,485), and U.S. patent application Ser. No. 10/460,291, filed Jun. 11, 2003 (now U.S. Pat. No. 7,743,960), each of which, as set forth above, are hereby expressly incorporated herein by reference in their entirety.

Various drivers may be employed to drive the movements of the surgical device 11, e.g., pivoting the first jaw 50 relative to the second jaw 80, firing of a staple cartridge, pivoting the jaw portion 11*a* relative to the shaft portion 11*b*, rotating the jaw and shaft portions 11*a*, 11*b* or some part thereof around the longitudinal axis of the shaft portion 11*b*, etc. According to an embodiment of the present invention, these functions are performed by connection of the surgical device 11 to a flexible shaft having two rotatable drive shafts, although is should be recognized that in other embodiments, different types and/or a different number of drive components may be employed.

FIG. 2(*b*) illustrates schematically that the handle 1103 includes a function selector module 1110. Additional details of the function selector module 1110 are set forth below. Generally, the function selector module 1110 is actuatable by a first rotatable drive shaft 1110*a* so as to move between a plurality of different functional positions. In the embodiment shown, the function selector module 1110 is actuatable by the first rotatable drive shaft 1110*a* between four different functional positions, each of which is set forth more fully below. The function selector module 1110 is configured such that, in each one of the different functional positions, the function selector module 1110 causes engagement of a second rotatable drive shaft 1110*b* with a selected one of various drivers 88, 98, 201, 202 of the surgical device 11. Each one of the drivers 88, 98, 201, 202 is configured to perform, upon engagement with and operation of the second rotatable drive shaft 1110*b*, a particular function of the surgical device 11, as set forth below.

As set forth above, in the embodiment shown in FIG. 2(*b*), the handle 1103 includes a connection element 1104, which enables the first rotatable drive shaft 1110*a* to be coupled to the third rotatable drive shaft 94 via the first drive socket 654. The third rotatable drive shaft 94 is in turn coupled to, or coupleable to, a first motor 96. In this manner, operation of the first motor 96 to rotate the third rotatable drive shaft 94, the first drive socket 654 and first rotatable drive shaft 1110*a* may actuate the function selection module 1110.

Also, in the embodiment shown in FIG. 2(*b*), the connection element 1104 of the handle 1103 may enable the second rotatable drive shaft 1110*b* to be coupled to a fourth rotatable drive shaft 102 via a second drive socket 694. The fourth rotatable drive shaft 102 is in turn coupled to, or coupleable to, a second motor 100. In this manner, operation of the second motor 100 to rotate the fourth rotatable drive shaft 102, the second drive socket 694 and second rotatable drive shaft 1110*b* may drive the particular driver mechanism that has previously been selected by the operation of the function selection module 1110.

In an embodiment, a first function that may be performed by the surgical device 11 is to rotate the shaft portion 11*b* about longitudinal axis D relative to the handle 1103, e.g., to operate a rotation gear within the handle 1103 so as to rotate the shaft portion 11*b* about longitudinal axis D relative to the handle 1103. To perform this function, the function selection module 1110 may initially be positioned in a first selection position by the actuation of the first rotatable drive shaft 1110*a* by the first motor 96 (and by the rotation of third rotatable drive shaft 94 and the first drive socket 654 engaged therebetween). Once the function selection module 1110 is positioned in the first selection position, the function selection module 1110 causes the rotation driver 202 to be engaged with the second motor 100 (via the fourth rotatable drive shaft 102 and the second drive socket 694 engaged therebetween), such that operation of the second motor 100 actuates the rotation driver 202. In the embodiment described herein, the rotation driver 202, when actuated by the second motor 100 (via the fourth rotatable drive shaft 102 and the second drive socket 694 engaged therebetween), may operate to rotate the shaft portion 11*b* about longitudinal axis D relative to the handle 1103, e.g., to operate a rotation gear within the handle 1103 so as to rotate the shaft portion 11*b* about longitudinal axis D relative to the handle 1103, in addition to performing other operations of the surgical device 11. The rotation driver 202 may include any type of drive mechanism capable of rotating the shaft portion 11*b* about longitudinal axis D relative to the handle 1103, e.g., of operating a rotation gear within the handle 1103 so as to rotate the shaft portion 11*b* about longitudinal axis D relative to the handle 1103. The rotation driver 202 may be situated in the distal portion of the handle 1103 and may engage the shaft portion 11*b* for the purposes of moving the shaft portion 11*b* relative to the handle 1103. Additional details of the rotation driver 202, in accordance with an example embodiment of the present invention, are set forth in greater detail below.

In an embodiment, a second function that may be performed by the surgical device 11 is to move the jaw portion 11*a* relative to the shaft portion 11*b*, e.g., to pivot the jaw portion 11*a* about axis B relative to the shaft portion 11*b*. To perform this function, the function selection module 1110 may initially be positioned in a second selection position by the actuation of the first rotatable drive shaft 1110*a* by the first motor 96 (and by the rotation of third rotatable drive shaft 94 and the first drive socket 654 engaged therebetween). Once the function selection module 1110 is positioned in the second selection position, the function selection module 1110 causes the articulation driver 201 to be engaged with the second motor 100 (via the fourth rotatable drive shaft 102 and the second drive socket 694 engaged therebetween), such that operation of the second motor 100 actuates the articulation driver 201. In the embodiment described herein, the articulation driver 201, when actuated by the second motor 100 (via the fourth rotatable drive shaft 102 and the second drive socket 694 engaged therebetween), may operate to move the jaw portion 11*a* relative to the shaft portion 11*b*, e.g., to pivot the jaw portion 11*a* about axis B relative to the shaft portion 11*b*, in addition to performing other operations of the surgical device 11. The articulation driver 201 may include any type of drive mechanism capable of the jaw portion 11*a* relative to the shaft portion 11*b*, e.g., to pivot the jaw portion 11*a* about axis B relative to the shaft portion 11*b*. The articulation driver 201 may be situated in the distal portion 1101*a* of the shaft portion 11*b* and may engage the jaw portion 11*a* for the purposes of moving the jaw portion 11*a* relative to the shaft portion 11*b*. Additional details of the articulation driver 201, in accordance with an example embodiment of the present invention, are set forth in greater detail below.

In an embodiment, a third function that may be performed by the surgical device 11 is to move, e.g., open and close by pivoting or any other conceivable relative movement, the first jaw 50 relative to the second jaw 80. To perform this function, the function selection module 1110 may initially be positioned in a third selection position by the actuation of the first rotatable drive shaft 1110*a* by the first motor 96 (and by the rotation of third rotatable drive shaft 94 and the first drive socket 654 engaged therebetween). Once the function selection module 1110 is positioned in the third selection position, the function selection module 1110 causes the clamping driver 88 to be engaged with the second motor 100 (via the fourth rotatable drive shaft 102 and the second drive socket 694 engaged therebetween), such that operation of the second motor 100 actuates the clamping driver 88. In the embodiment described herein, the clamping driver 88, when actuated by the second motor 100 (via the fourth rotatable drive shaft 102 and the second drive socket 694 engaged therebetween), may operate to move, e.g., open and close, the first jaw 50 relative to the second jaw 80, in addition to performing other operations of the surgical device 11. The clamping driver 88 may include any type of drive mechanism capable of moving the first jaw 50 and the second jaw 80 relative to each other. The clamping driver 88 may be situated at least partially in the proximal end 80*b* of the second jaw 80 and may be connected to the proximal end 50*b* of the first jaw 50 so as to engage the proximal end 50*b* of the first jaw 50 for opening and closing the first jaw 50 relative to the second jaw 80. Additional details of the clamping driver 88, in accordance with an example embodiment of the present invention, are set forth in greater detail below.

In an embodiment, a fourth function that may be performed by the surgical device 11 is to move a cutting and/or stapling element, e.g., to drive a staple pushing element and/or cutting blade through a section of tissue such as by turning a threaded drive shaft of the cutting and stapling element 104. To perform this function, the function selection module 1110 may initially be positioned in a fourth selection position by the actuation of the first rotatable drive shaft 1110*a* by the first motor 96 (and by the rotation of third rotatable drive shaft 94 and the first drive socket 654 engaged therebetween). Once the function selection module 1110 is positioned in the fourth selection position, the function selection module 1110 causes the firing driver 98 to be engaged with the second motor 100 (via the fourth rotatable drive shaft 102 and the second drive socket 694 engaged therebetween), such that operation of the second motor 100 actuates the second driver 88. In the embodiment described herein, the second driver 88, when actuated by the second motor 100 (via the fourth rotatable drive shaft 102 and the second drive socket 694 engaged therebetween), may operate to move a cutting and/or stapling element, e.g., to drive a staple pushing element and/or cutting blade through a section of tissue, in addition to performing other operations of the surgical device 11. The firing driver 98 may include any type of drive mechanism capable of moving a cutting and/or stapling element, e.g., driving a staple pushing element and/or cutting blade through a section of tissue. The firing driver 88 may be situated between the proximal end 80*b* and the distal end 80*a* of the second jaw 80 so as to cut and/or staple a section of tissue disposed between the first jaw 50 and the second jaw 80. Additional details of the firing driver 98, in accordance with an example embodiment of the present invention, are set forth in greater detail below.

It should be recognized that, while two drive sockets, e.g., the first drive socket 654 and the second drive socket 694, and two corresponding drive shafts, e.g., the first drive shaft 94 and the second drive shaft 102, are illustrated as being part of the surgical device 11 and as being for the purposes of, e.g., moving and positioning certain components of the surgical device 11 relative to other components and/or clamping, cutting and stapling a section of tissue, it is possible to provide any suitable number of drive sockets and drive shafts. For example, a single drive shaft, or more than two drive shafts, may be provided to perform the above-described functions of the surgical device 11.

The drive shafts, e.g., the first and second rotatable drive shafts 94 and 102 and any other drive shafts, may be housed within a flexible drive shaft, such as the flexible drive shaft 1620 illustrated in FIG. 2(*a*). Other types of flexible drive shafts may also be employed. For instance, the drive shafts may be housed within a flexible drive shaft of the type described and illustrated in U.S. Provisional Patent Application No. 60/703,227, filed Jul. 27, 2006 and entitled "Flexible Shaft for an Electro-Mechanical Surgical Device," which is expressly incorporated by reference herein in its entirety.

Referring to FIG. 2(*b*), the surgical device 11 may also include a memory module 6041. In an embodiment, the memory module 6041 is connected to or integral with the cutting and stapling element 104. The memory module 6041 is connected to a data connector 1272 by a data transfer cable 1278. Additional features of these components are set forth in connection with, e.g., FIGS. 3(*f*) and 7.

Furthermore, FIG. 2(*b*) also illustrates a connection element 1104. The connection element 1104 may include a quick connect sleeve 713 that has quick connect slots 713*a* that engage complementary quick connect elements 1664 of a flexible drive shaft 1620, which is described in further detail below. In order to retain the quick connect elements 1664 of the flexible drive shaft 1620 in the quick connect slots 713*a* of the quick connect sleeve 713, the connection element 1104 may also include a spring.

Also, it should be recognized that the motors employed to drive the first and second rotatable drive shafts 1110*a* and 1110*b* may be integral with the surgical device 11. For example, FIG. 2(*c*) is a schematic diagram that illustrates an alternative arrangement of the surgical device 11, according to another example embodiment of the present invention. In this embodiment, first motor 961 and second motor 1001 are arranged within the handle 1103, such that the first and second rotatable drive shafts 1110*a* and 1110*b* are connected to the first and second motors 961, 1001, respectively.

According to an example embodiment of the present invention, the surgical device 11 may be configured as an attachment to, or may be integral with, an electro-mechanical surgical system, such as the electro-mechanical driver component 1610 having a motor system illustrated in FIG. 2(*a*). It should be appreciated that, in this example embodiment, any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors. In another example embodiment, the surgical device may be an attachment to, or may integral with, a mechanical driver system.

FIG. 3(*a*) is a perspective view of a surgical device 11, according to an embodiment of the present invention. As set forth above, FIGS. 3(*a*) to 3(*e*) illustrate an embodiment of the present invention in which two drive shafts are configured to be employed to rotate the shaft portion 11*b* relative to, and about the longitudinal axis of, the handle 1103; to move, e.g., articulate, the jaw portion 11*a* relative to the shaft portion 11*b*; to move, e.g., open or close, the first jaw 50 relative to the second jaw 80; and to fire a stapling and cutting cartridge. In the position shown in FIG. 3(*a*), the jaw portion 11*a* is positioned at an angle of approximately 60 degrees relative to the shaft portion 11*b*. The jaw portion 11*a* may be appropriately positioned according to the incision made in the patient and to the position of the tissue desired to be clamped, cut and/or stapled.

As set forth above, FIG. 3(*b*) is a side view, partially in section, that illustrates the handle 1103 of the surgical device, according to an embodiment of the present invention. FIG. 3(*c*) is a side perspective view, partially in section, that illustrates additional features of the handle of the surgical device, according to the embodiment illustrated in FIG. 3(*b*). FIGS. 3(*d*) and 3(*e*) are side perspective views, partially in section, that illustrates still further features of the handle of the surgical device, according to an embodiment of the present invention.

Referring now to FIG. 3(*b*), it is illustrated that the handle 1103 includes the first rotatable drive shaft 1110*a* which extends from a proximal end of the handle 1103 inwardly. The first rotatable drive shaft 1110*a* has a longitudinally-arranged bore in which a proximal end of a selector shaft 601 is arranged. Advantageously, the longitudinally-arranged bore of the first rotatable drive shaft 1110*a* and the proximal end of a selector shaft 601 are correspondingly sized and shaped such that, when engaged, rotation of the first rotatable drive shaft 1110*a* causes rotation of the selector shaft 601. In addition, the proximal end of the selector shaft 601 is inserted through a spring 603, and is maintained in position between a longitudinal stop of the selector shaft 601 and the first rotatable drive shaft 1110*a*. The spring 603 functions to bias the first rotatable drive shaft 1110*a* is a proximal direction.

A distal-most end of the selector shaft 601 is rotatably mounted within an orifice of a fixed interior wall 605 of the handle, the fixed interior wall 605 of the handle 1103 being perpendicular to the longitudinal axis of the selector shaft 601. The selector shaft 601 also includes, along a length that is adjacent to the distal-most end thereof, a threaded portion 607. A function selector block 609 has a threaded bore that extends longitudinally therethrough. The threaded portion 607 of the selector shaft 601 extends through the threaded bore of the function selector block 609 such that the function selector block 609 is mounted thereon. The function selector block 609 is keyed to an interior surface of the handle such that, upon rotation of the selector shaft 601, the threaded engagement of the threaded portion 607 of the selector shaft 601 within the threaded bore of the function selector block 609 causes the function selector block 609 to move distally and proximally along the selector shaft 601.

FIG. 3(*b*) also illustrates that the handle 1103 includes the second rotatable drive shaft 1110*b* which extends from a proximal end of the handle 1103 inwardly. The second rotatable drive shaft 1110*b* has a longitudinally-arranged bore into which a proximal end of a function shaft 611 is arranged. Advantageously, the longitudinally-arranged bore of the second rotatable drive shaft 1110*b* and the proximal end of the function shaft 611 are correspondingly sized and shaped such that, when engaged, rotation of the second rotatable drive shaft 1110*b* causes rotation of the function shaft 611. In addition, the proximal end of the function shaft 611 is inserted through a spring 613, and is maintained in position between a longitudinal stop of the function shaft 611 and the second rotatable drive shaft 1110*b*. The spring 613 functions to bias the second rotatable drive shaft 1110*b* in a proximal direction.

A distal-most end of the function shaft 611 is rotatably mounted within an orifice of a fixed interior wall 615 of the handle, the fixed interior wall 615 of the handle 1103 being perpendicular to the longitudinal axis of the function shaft 611. The function shaft 611 also includes, along a length that is adjacent to the distal-most end thereof, a fire spur gear 617. Located along the function shaft 611 in a position that is proximal relative to the fire spur gear 617 is an input spur gear 619. The fire spur gear 617 and the input spur gear 619 each have respective outer circumferential gear teeth 6171, 6191. Also rotatably mounted within an orifice of a fixed interior wall 615 of the handle is a secondary fire spur gear 618. The secondary fire spur gear 618 has outer circumferential gear teeth 6181 that are meshingly engaged with the outer circumferential gear teeth 6191 of the fire spur gear 619.

Extending distally from the function selector block 609 is a gear shaft 621. Arranged at varying longitudinal positions along the gear shaft 621 are various gears. For example, at a longitudinal position along the gear shaft 621 that is most nearly adjacent to the function selector block 609 is a rotation spur gear 623. The rotation spur gear 623 includes outer circumferential gear teeth 6231. The outer circumferential gear teeth 6231 engage the outer circumferential gear teeth 6191 of the input spur gear 619. In an embodiment, the rotation spur gear 623 and the input spur gear 619 provides a 4:1 gear ratio relative to each other. Of course, it should be recognized that any suitable gear ratio may be employed. Also, at a longitudinal position along the gear shaft 621 that is distal relative to the rotation spur gear 623 is a fire spur gear 625. The fire spur gear 625 includes outer circumferential gear teeth 6251. The outer circumferential gear teeth 6251 of the fire spur gear 625 engage the outer circumferential gear teeth 6171 of the fire spur gear 617. In addition, at a longitudinal position along the gear shaft 621 that is distal relative to the fire spur gear 625 is a clamping spur gear 627. The clamping spur gear 627 includes outer circumferential gear teeth 6271. At a longitudinal position along the gear shaft 621 that is distal relative to the clamping spur gear 627 is an articulation spur gear 629. The articulation spur gear 629 includes outer circumferential gear teeth 6291. Still further, at a longitudinal position along the gear shaft 621 that is distal relative to the articulation spur gear 629 is a rotation spur gear 631. The rotation spur gear 631 includes outer circumferential gear teeth 6311.

The handle 1103 also includes a rotation gear shaft 633. A proximal end of the rotation gear shaft 633 is rotatably mounted within an orifice of a fixed interior wall 635 of the handle 1103, the fixed interior wall 635 of the handle 1103 being generally perpendicular to the longitudinal axis of the rotation gear shaft 633. A distal end of the rotation gear shaft 633 is rotatably mounted within an orifice of a fixed interior wall 637 of the handle 1103, the fixed interior wall 637 of the handle 1103 also being generally perpendicular to the longitudinal axis of the rotation gear shaft 633. The rotation gear shaft 633 includes, along a length that is adjacent to its proximal end, a rotation spur gear 639. The rotation spur gear 639 has outer circumferential gear teeth 6391. The rotation gear shaft 633 also includes, along a length that is adjacent to its distal end, a rotation worm gear 641. The rotation worm gear 641 has outer circumferential worm gear teeth 6411.

A rotation gear 643 is rotatably mounted to a fixed interior wall 645 of the handle 1103. Advantageously, the rotation gear 643 is rotatably mounted about a pivot axis that is perpendicular to a longitudinal axis of the rotation gear shaft 633. The rotation gear 643 has outer circumferential gear teeth 6431 that are meshingly engaged with the outer circumferential worm gear teeth 6411 of the rotation worm gear 641. In an embodiment, the rotation gear 643 and the rotation worm gear 641 provide a 45:1 gear ratio relative to each other. Of course, it should be recognized that any suitable gear ratio may be employed. Mounted to a surface of the rotation gear 643, and configured to rotate therewith, is a rotation miter gear 644. The rotation miter gear 644 has miter gear teeth 6441.

The handle 1103 also includes a second rotation gear shaft 665. The second rotation gear shaft 665 is maintained within the handle 1103 by a channel 667 in which the second rotation gear shaft 665 is longitudinally and rotatably maintained. A proximal end of the second rotation gear shaft 665 includes a rotation miter gear 669. The rotation miter gear 669 has miter gear teeth 6691. The miter gear teeth 6691 of the rotation miter gear 669 are meshingly engaged with the miter gear teeth 6441 of the miter gear 644.

A distal end of the second rotation gear shaft 665 is rotatably mounted within an orifice of a fixed interior wall 671 of the handle 1103, the fixed interior wall 671 of the handle 1103 being generally perpendicular to the longitudinal axis of the second clamping gear shaft 665. The second rotation gear shaft 665 also includes, along a length that is adjacent to its distal end, a rotation spur gear 673. The rotation spur gear 673 has outer circumferential gear teeth 6731.

Mounted within a mouth 675 at the distal-most end of the handle 1103 is a rotating tube 677. Longitudinal stops maintain the rotating tube 677 longitudinally within the mouth 675. The distal end of the rotating tube 677 extends to the tube housing 523. The proximal end of the rotating tube 677 includes a rotating tube spur gear 679. The rotating tube spur gear 679 has outer circumferential gear teeth 6791. The outer circumferential gear teeth 6791 of the rotating tube spur gear 679 are meshingly engaged with the outer circumferential gear teeth 6731 of the rotation spur gear 673. In an embodiment, the rotation spur gear 673 and the rotating tube spur gear 679 provides a 1.4:1 gear ratio relative to each other. Of course, it should be recognized that any suitable gear ratio may be employed.

FIG. 5(*b*) illustrates, partially in section, a side perspective view that is opposite from the side view provided in FIG. 3(*b*). FIG. 5(*b*) illustrates additional components of the handle 1103 that are hidden from view in FIG. 3(*b*). Referring now to FIG. 5(*b*), there is shown an articulation gear shaft 685. A proximal end of the articulation gear shaft 685 is rotatably mounted within an orifice of a fixed interior wall (shown in phantom) of the handle 1103, the fixed interior wall of the handle 1103 being generally perpendicular to the longitudinal axis of the articulation gear shaft 685. A distal end of the articulation gear shaft 685 is rotatably mounted within an orifice of another fixed interior wall (also shown in phantom) of the handle 1103, this fixed interior wall of the handle 1103 also being generally perpendicular to the longitudinal axis of the articulation gear shaft 685. The articulation gear shaft 685 includes, along a length that is adjacent to its proximal end, an articulation spur gear 687. The articulation spur gear 687 has outer circumferential gear teeth 6871. The outer circumferential gear teeth 6871 of the articulation spur gear 687 are meshingly engaged with the outer circumferential gear teeth 6291 of the articulation spur gear 629. The articulation gear shaft 685 also includes, along a length that is adjacent to its distal end, articulation worm gear 689. The articulation worm gear 689 has outer circumferential worm gear teeth 6891.

An articulation gear 691 is rotatably mounted to a fixed interior wall 693 of the handle 1103. Advantageously, the articulation gear 691 is rotatably mounted about a pivot axis that is perpendicular to a longitudinal axis of the articulation gear shaft 685. The articulation gear 691 has outer circumferential gear teeth 6911 that are meshingly engaged with the outer circumferential worm gear teeth 6891 of the articulation worm gear 689. In an embodiment, the articulation gear 691 and the articulation worm gear 689 provide a 11.25:1 gear ratio relative to each other. Of course, it should be recognized that any suitable gear ratio may be employed.

Referring back again to FIG. 3(*b*), there are shown additional features of the handle 1103 that contribute to the articulation function. For example, mounted to a surface of the articulation gear 691, and configured to rotate therewith, is a first articulation miter gear 692. The first articulation miter gear 692 has miter gear teeth 6921.

The handle 1103 also includes a second articulation gear shaft 693. The second articulation gear shaft 693 is rotatably maintained within the handle 1103 by a channel 694. A proximal end of the second articulation gear shaft 693 forms a threaded rod 695. Mounted on the threaded rod 695 is a second articulation miter gear 696, which is mounted within the handle 696 by an articulation miter gear support 697. The second articulation miter gear 696 has miter gear teeth 6961. The miter gear teeth 6961 of the second articulation miter gear 696 are meshingly engaged with the miter gear teeth 6921 of the first articulation miter gear 692. The articulation gear support 697 maintains the longitudinal and radial positions of the second articulation miter gear 696 within the handle 1103, while allowing the second articulation miter gear 696 to rotate about its longitudinal axis. The second articulation miter gear 696 defines a longitudinally-arranged threaded bore, the threaded rod 695 of the second articulation gear shaft 693 engaging the longitudinally-arranged threaded bore of the second articulation miter gear 696.

The distal end of the second articulation gear shaft 693 extends through a longitudinally-defined opening through the center region of the rotating tube spur gear 679 and passes through the rotating tube 677 at the mouth 675 of the handle 1103 so as to eventually form the articulation shaft 525 (as shown in FIG. 4(*a*)). By virtue of the threaded engagement between the threaded rod 695 of the second articulation gear shaft 693 and the longitudinally-arranged threaded bore of the second articulation miter gear 696, rotation of the second articulation miter gear 696 causes selective movement in either a distal or proximal direction of the second articulation gear shaft 693 relative to the handle 1103.

Referring to FIG. 3(*b*), the handle 1103 also includes a clamping gear shaft 651. A proximal end of the clamping gear shaft 651 is rotatably mounted within an orifice of a fixed interior wall 653 of the handle 1103, the fixed interior wall 653 of the handle 1103 being generally perpendicular to the longitudinal axis of the clamping gear shaft 651. The clamping gear shaft 651 includes, along a length that is adjacent to its distal end, a clamping spur gear 655. The clamping spur gear 655 has outer circumferential gear teeth 6551. The clamping gear shaft 651 also includes at its distal end a first clamping miter gear 657. The first clamping miter gear 657 has miter gear teeth 6571.

A second clamping miter gear 659 is rotatably mounted to a fixed interior wall 663 of the handle 1103. Advantageously, the second clamping miter gear 659 is rotatably mounted about a pivot axis that is perpendicular to a longitudinal axis of the clamping gear shaft 651. The second clamping miter gear 659 has miter gear teeth 6591 that are meshingly engaged with the miter gear teeth 6571 of the first clamping miter gear 657.

Also, the handle 1103 includes a second clamping gear shaft 681. A proximal end of the second clamping gear shaft 681 includes a third clamping miter gear 661. The third clamping miter gear 661 has miter gear teeth 6611 that are meshingly engaged with the miter gear teeth 6591 of the second clamping miter gear 659. The distal end of the second clamping gear shaft 681 extends through a longitudinally-defined opening through the center region of the rotating tube spur gear 679 and passes through the rotating tube 677 at the mouth 675 of the handle 1103 so as to eventually form the clamping shaft 527 (as shown in FIG. 4(*a*)).

Referring to FIG. 3(*b*), the handle 1103 also includes a firing gear shaft 604. Adjacent to its proximal end, the firing gear shaft 604 is rotatably mounted within an orifice of a fixed interior support 606 of the handle 1103, the fixed interior support 604 of the handle 1103 including as its distal surface the fixed interior wall 606 into which the distal end of function shaft 611 is rotatably mounted. The firing gear shaft 604 includes, at its proximal end, a firing spur gear 608. The firing spur gear 608 has outer circumferential gear teeth 6081. The outer circumferential gear teeth 6081 of the firing spur gear 608 are meshingly engaged with the outer circumferential gear teeth 6171 of the firing spur gear 617.

FIG. 5(*d*) illustrates, partially in section, a side perspective view that is opposite from the side view provided in FIG. 3(*b*). FIG. 5(*d*) illustrates additional components of the handle 1103 that are hidden from view in FIG. 3(*b*). Referring now to FIG. 5(*d*), the firing gear shaft 604 includes, at its distal end, a first firing miter gear 610. The first firing miter gear 610 has miter gear teeth 6101.

A second firing miter gear 612 is rotatably mounted to a fixed interior wall 616 of the handle 1103. Advantageously, the second firing miter gear 612 is rotatably mounted about a pivot axis that is perpendicular to a longitudinal axis of the firing gear shaft 604. The second firing miter gear 612 has miter gear teeth 6121 that are meshingly engaged with the miter gear teeth 6101 of the first firing miter gear 610.

Also, the handle 1103 includes a second firing gear shaft 618. A proximal end of the second firing gear shaft 618 includes a third firing miter gear 614. The third firing miter gear 614 has miter gear teeth 6141 that are meshingly engaged with the miter gear teeth 6121 of the second firing miter gear 612. The distal end of the second firing gear shaft 618 extends through a longitudinally-defined opening through the center region of the rotating tube spur gear 679 and passes through the rotating tube 677 at the mouth 675 of the handle 1103 so as to eventually form the firing shaft 529 (as shown in FIG. 4(*a*)).

FIG. 3(*b*) also illustrates that, in accordance with an embodiment of the present invention, the surgical device 11 may include optical function sensors 3001, 3002, 3003 and 3004. These optical sensors 3001, 3002, 3003 and 3004 may each include a diode, e.g., LEDs, that provides light out of a respective hole of wall 3005. Movement of the function selector block 609 via the threaded portion 607 of the selector shaft 601, selectively blocks the transmission of light from one of the diodes of the sensors 3001, 3002, 3003 and 3004. This blocking of the transmission of light enables the surgical device 11 to determine which one of the four above-described functional positions the function selector block 609 is in, and therefore to control the operation of the surgical device 11 accordingly. In other words, depending on the position of the function selector block 609, corresponding signals to and from various ones of the optical sensors 3001, 3002, 3003 and 3004 are blocked, thereby providing a suitable controller with an indication when the surgical device 11 is satisfactorily positioned in one of the four above-described functional positions, e.g., rotation, articulation, opening/closing of the jaws relative to each other, and firing the cutting and/or stapling mechanism.

FIG. 3(*b*) also illustrates that, in accordance with an embodiment of the present invention, the surgical device 11 may include a rotation/articulation control device 3006. In an embodiment, the rotation/articulation control device 3006 may be a joystick-type device that is suitably positioned, e.g., on a top surface of the handle 1103, and sized so as to be actuatable by an operator's thumb when the operator is holding the handle 1103. Also, FIG. 3(*b*) illustrates that, in accordance with an embodiment of the present invention, the surgical device 11 may include an open/close/fire control device 3007. In an embodiment, the open/close/fire control device 3007 may be a trigger-type device that is suitably positioned, e.g., on a bottom surface of the handle 1103, and sized so as to be actuatable by an operator's forefinger when the operator is holding the handle 1103. The operation of the rotation/articulation control device 3006 and the open/close/fire control device 3007 are described in addition detail below.

FIGS. 3(*f*), 4(*a*) through 4(*c*) and 4(*d*) collectively illustrate the components of the surgical device that are distal relative to the handle 1103. For example, FIG. 3(*f*) is a side perspective view of a distal assembly of the surgical device 11, as assembled, according to an embodiment of the present invention. FIG. 4(*a*) is an exploded perspective view that illustrates a proximal section of this distal assembly, according to the embodiment illustrated in FIG. 3(*f*).

For example, FIG. 4(*a*) illustrates a proximal pivot housing 503 having a pair of longitudinally arranged orifices, each one of which is configured to receive a respective one of a pair of threaded screws 501*a*, 501*b*. The proximal pivot housing 503 also houses a pair of input bevel gears 505*a*, 505*b*, each one of which is configured to be inserted into a respective one of a pair of ball bearings 507*a*, 507*b*. Proximally arranged relative to the proximal pivot housing 503 is a tube housing 523.

Each one of the pair of input bevel gears 505*a*, 505*b* includes a longitudinally arranged orifice at its proximal end. Arranged proximally relative to the first ball bearing 507*a* is a bevel thrust block 509. The bevel thrust block 509 has a longitudinally-arranged bore therethrough. A distal end of a clamp shaft 527 is configured to extend through a longitudinally-arranged opening of the tube housing 523, through the longitudinally-arranged bore of the bevel thrust block 509, through the longitudinally-arranged bore of the ball bearing 507*a*, and to engage the longitudinally-arranged orifice at the proximal end of the input bevel gear 505*a*. Advantageously, the distal end of a clamp shaft 527 and the longitudinally-arranged orifice at the proximal end of the input bevel gear 505*a* are correspondingly sized and shaped such that, when engaged, rotation of the clamp shaft 527 causes rotation of the input bevel gear 505*a*.

Also, proximally arranged relative to the second ball bearing 507*b* is a bevel thrust block 511. The outer circumferential surface of the bevel thrust block 511 includes a circular-shaped notch 5111 which is configured to have seated therein an articulation thrust pin 513. A proximal articulation gear 515 has a central orifice into which the articulation thrust pin 513 is configured to be inserted from below. The bevel thrust block 511 also has a longitudinally-arranged bore therethrough. A distal end of a firing shaft 529 is configured to extend through a longitudinally-arranged opening of the tube housing 523, through the longitudinally-arranged bore of the bevel thrust block 511, and to engage the longitudinally-arranged orifice at the proximal end of the input bevel gear 505b. Advantageously, the distal end of a firing shaft 529 and the longitudinally-arranged orifice at the proximal end of the input bevel gear 505b are correspondingly sized and shaped such that, when engaged, rotation of the firing shaft 529 causes rotation of the input bevel gear 505b.

The tube housing 503 has a pair of vertically-aligned bores 5031 at its distal end. In addition, the tube housing 503 has a suitably shaped slot at its distal end to receive a portion of the proximal articulation gear 515. In addition to the articulation thrust pin 513 which is configured to be inserted from below into the central orifice of the proximal articulation gear 515, the central orifice of the articulation gear 515 is also suitably sized and shaped so as to receive from above a rack gear 519. The teeth of the rack gear 519 are configured to engage a rack 517. The rack 517 extends through a corresponding shaped longitudinally-arranged opening in the tube housing 513. An orifice at the proximal end of the rack 517 is configured to receive a distal end of an articulation shaft 525, and is maintained in position relative thereto by a clip 521.

Figure 3A:
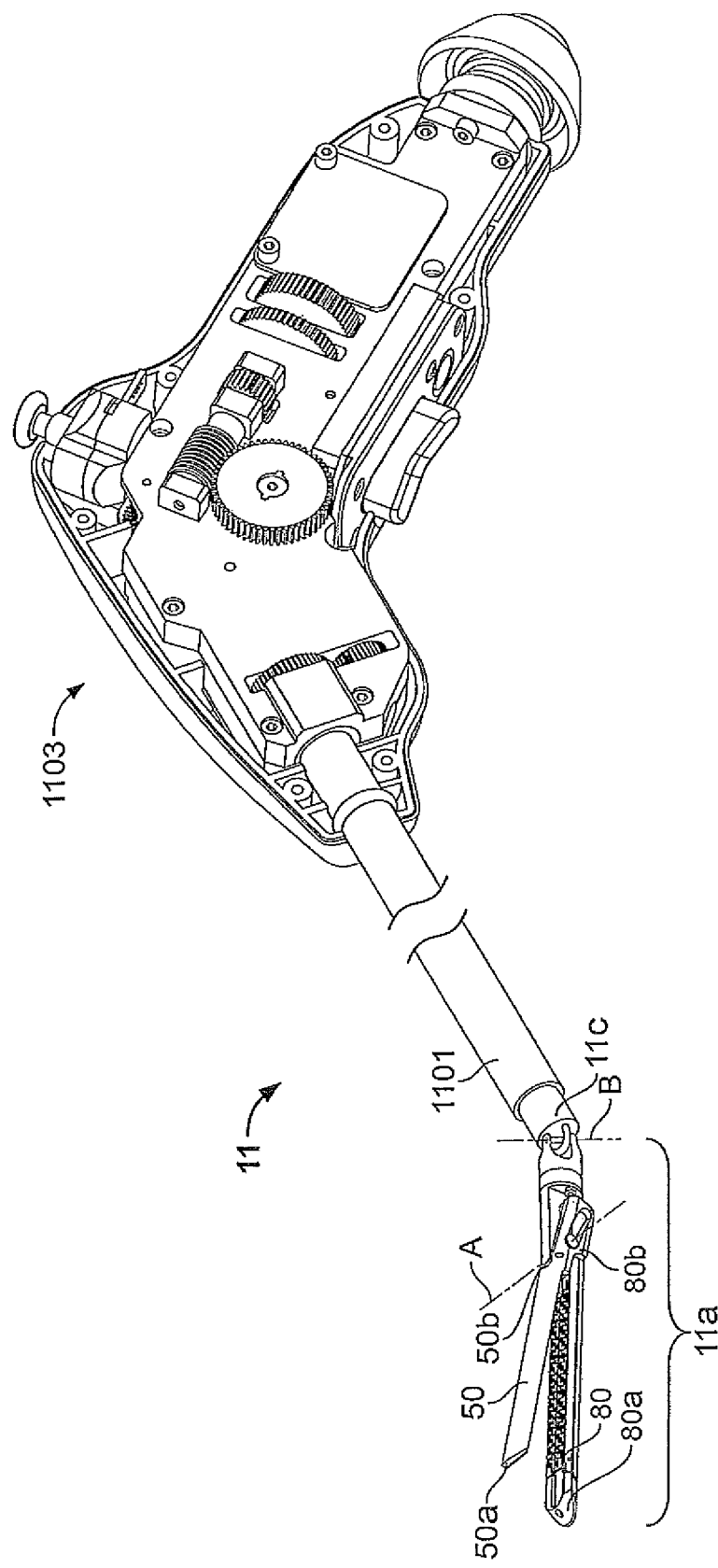
FIG. 3(a) is a perspective view of a surgical device, according to an example embodiment of the present invention.
Figure 3B:
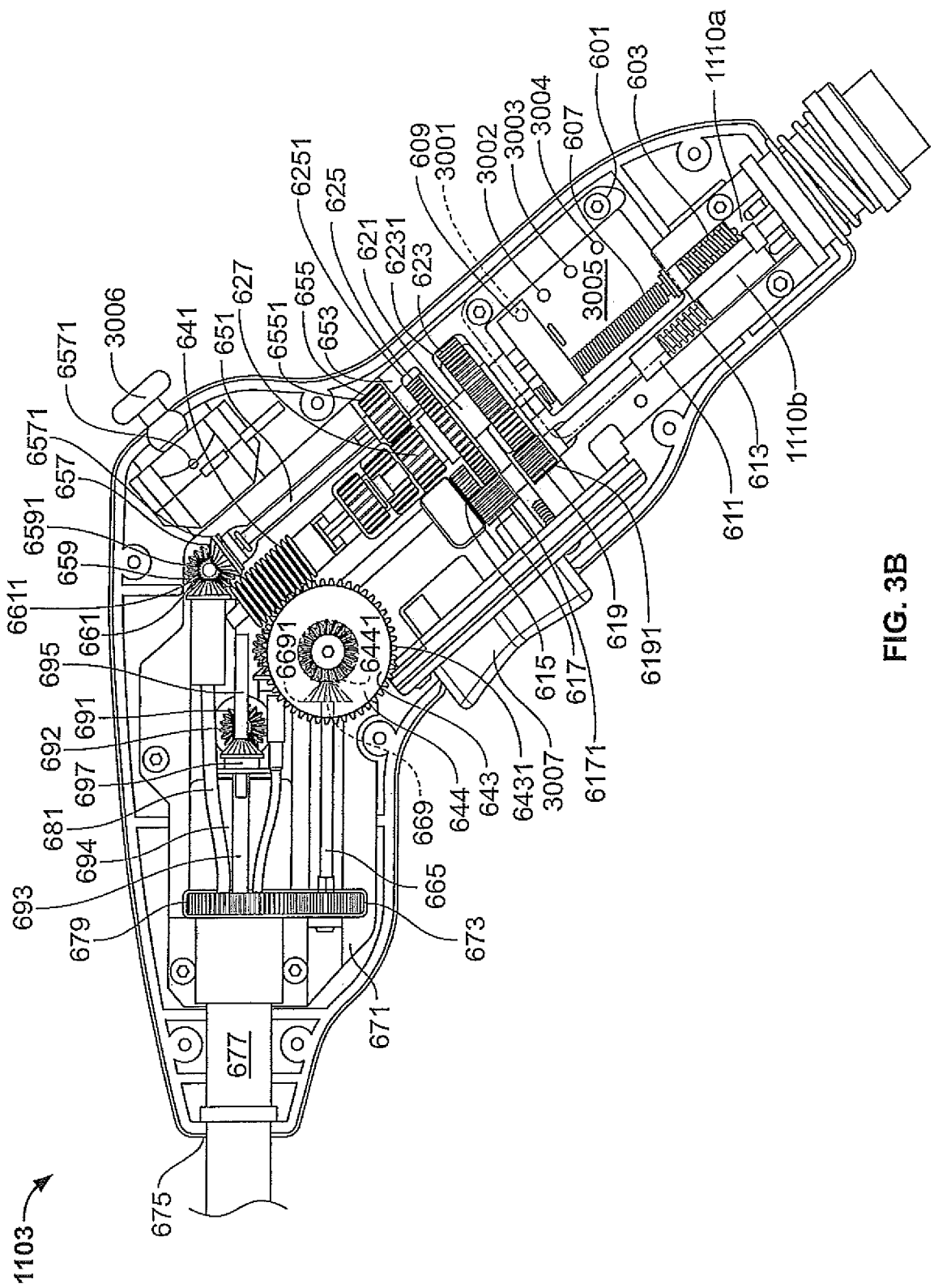
FIG. 3(b) is a side view, partially in section, that illustrates a handle of the surgical device, according to an embodiment of the present invention.
Figure 3C:
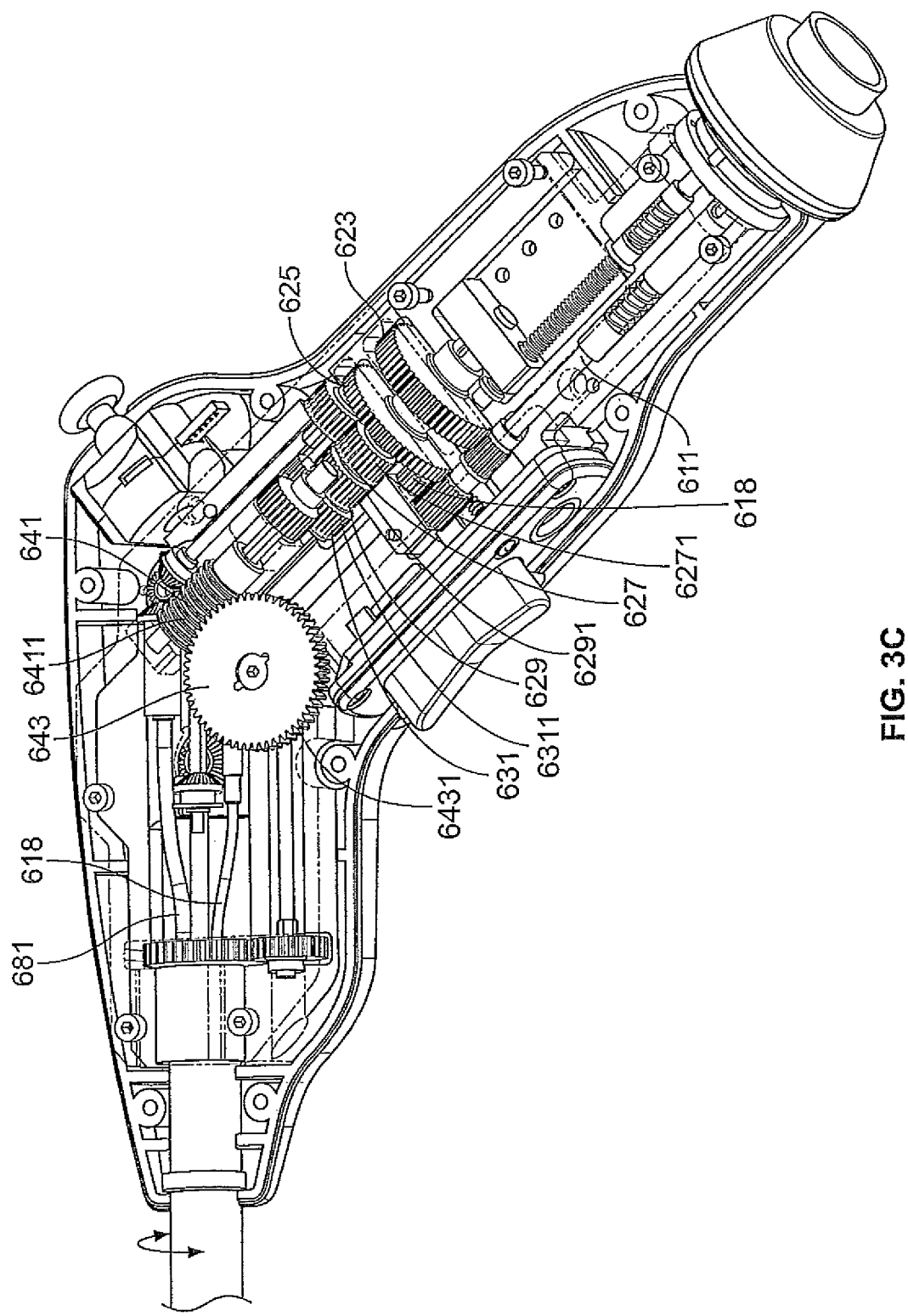
FIG. 3(c) is a side perspective view, partially in section, that illustrates additional features of the handle of the surgical device, according to the embodiment illustrated in FIG. 3(b)
Figures 3D, 3E:
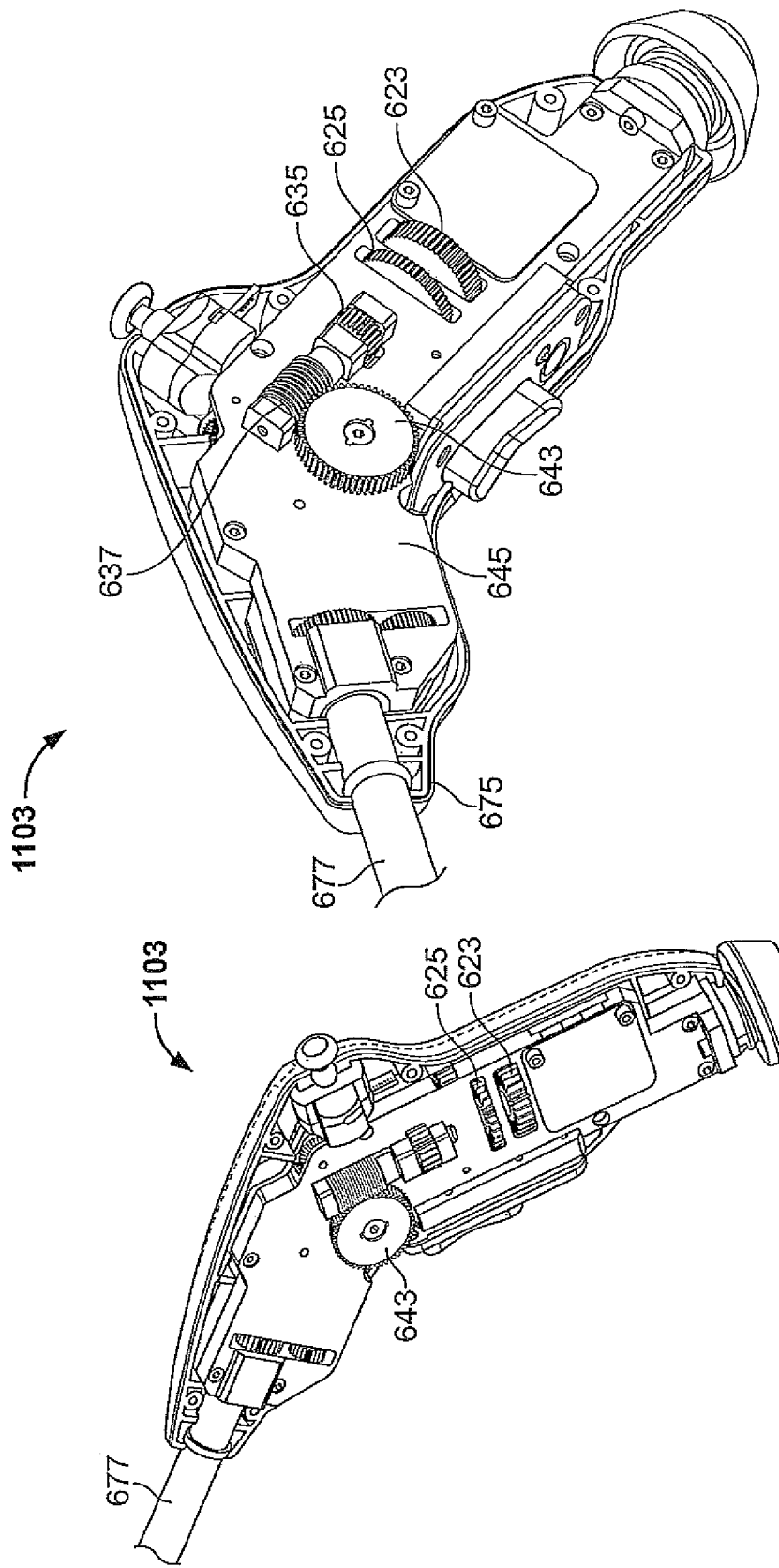
FIGS. 3(d) and 3(e) are side perspective views, partially in section, that illustrates still further features of the handle of the surgical device, according to an embodiment of the present invention.
Figure 3F:
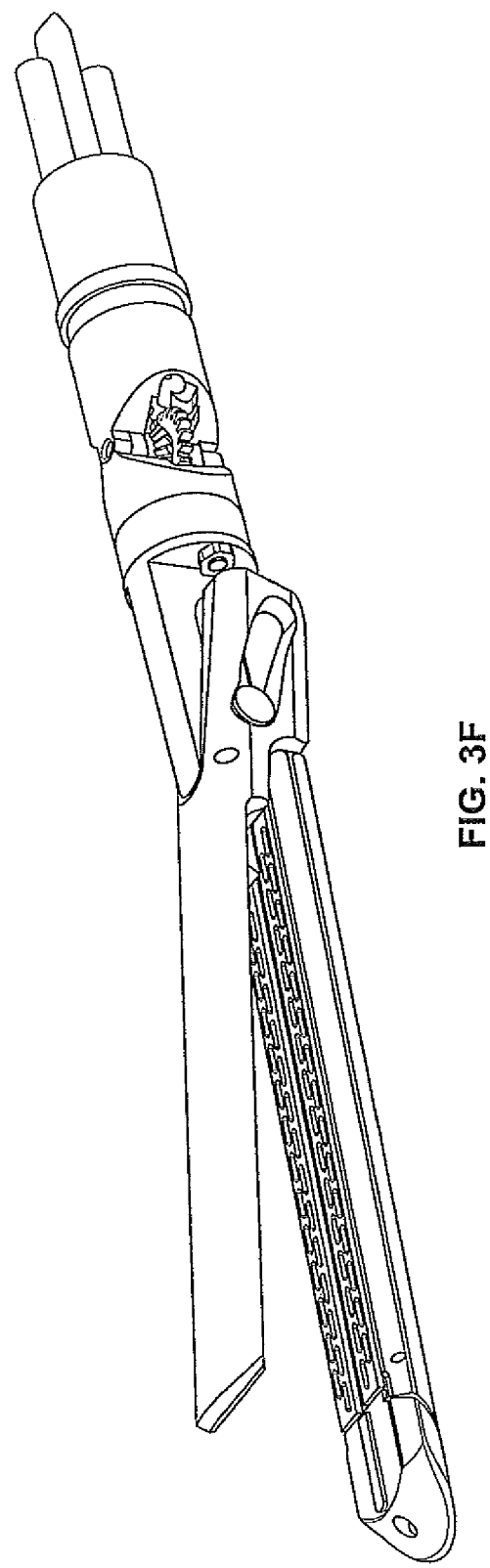
FIG. 3(f) is a side perspective view of a distal assembly of the surgical device, according to an embodiment of the present invention.
Figure 4A:
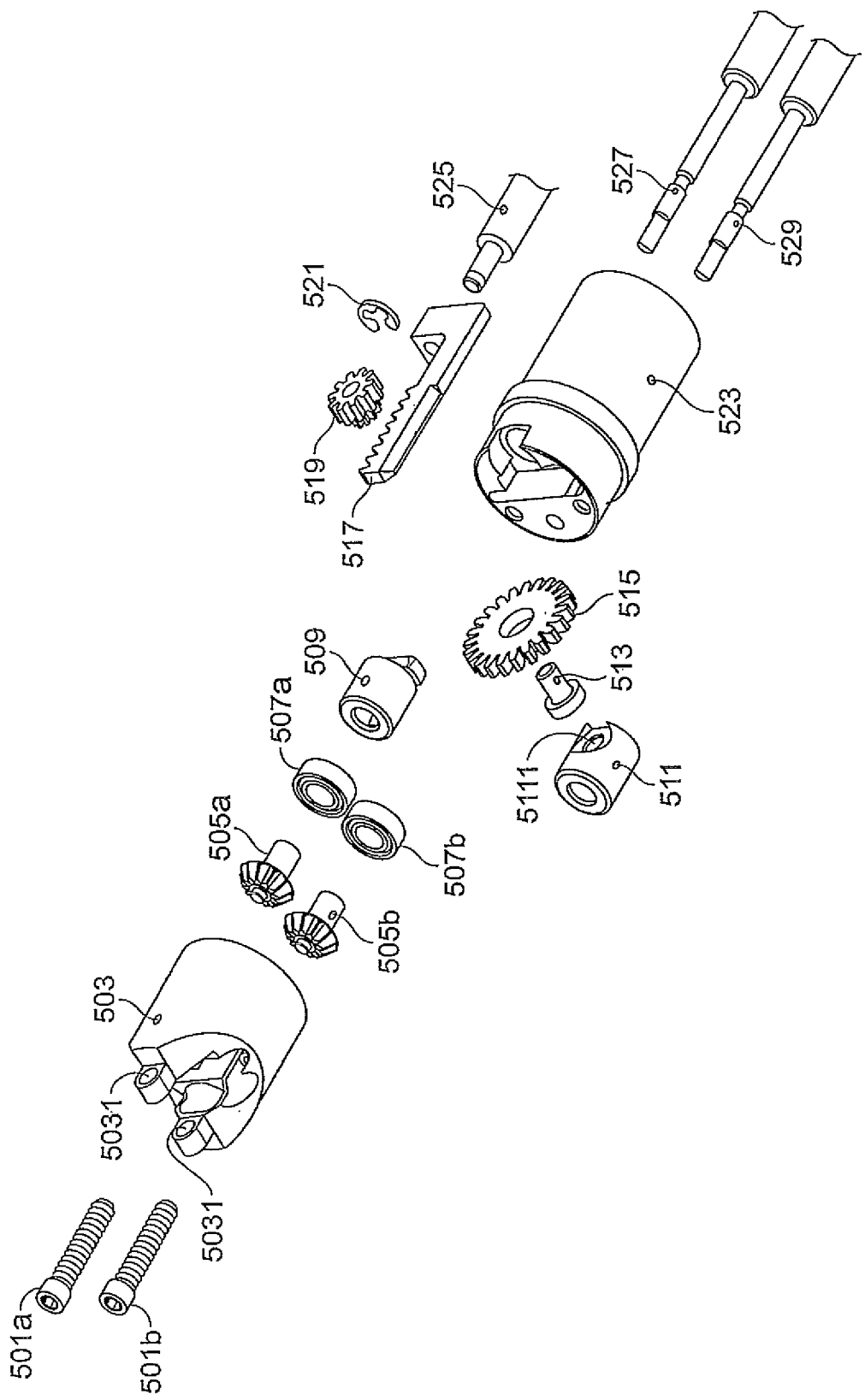
FIG. 4(a) is an exploded perspective view that illustrates a proximal section of the distal assembly, according to the embodiment illustrated in FIG. 3(f)
Figure 4B:
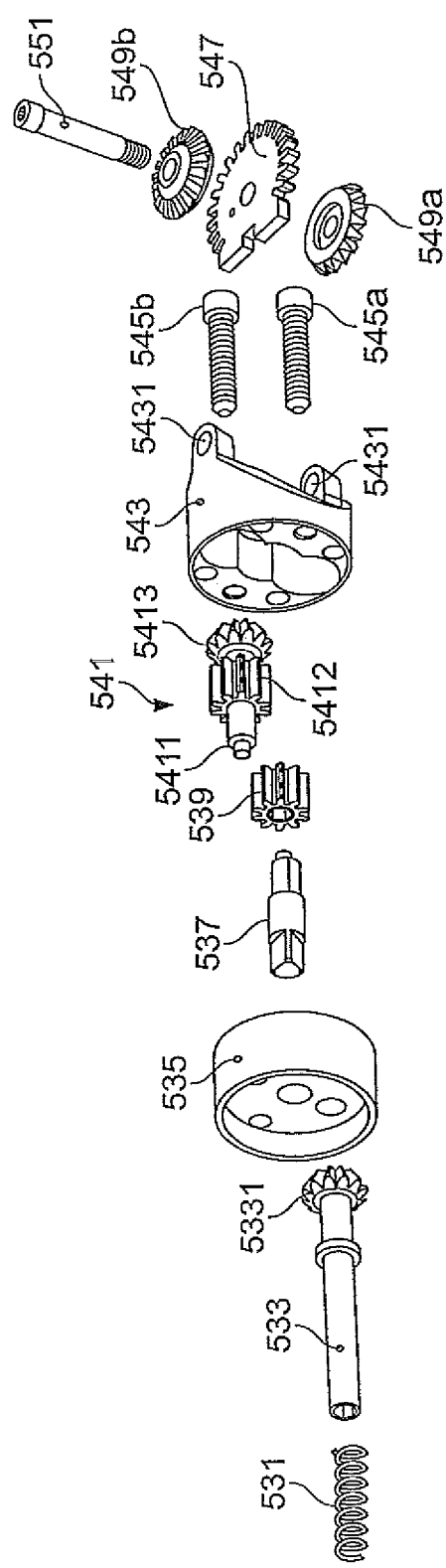
FIG. 4(b) is an exploded perspective view that illustrates an intermediate section of the distal assembly, according to the embodiment illustrated in FIG. 3(f)

As set forth above, FIG. 4(b) is an exploded perspective view that illustrates an articulation assembly section of the distal assembly, according to the embodiment illustrated in FIG. 3(f). FIG. 4(b) illustrates a firing spring 531 which is configured to engage a firing input bevel gear 533. The firing input bevel gear 533 is configured to extend through a longitudinally-arranged opening in a cartridge housing coupling 535 and has a bevel gear 5331 at its proximal end. In addition, a clamp screw shaft 537 also extends through a longitudinally-arranged opening in the cartridge housing coupling 535. Arranged proximally relative to the clamp screw shaft 537 is an outer idler gear 539. The outer idler gear 539 includes a longitudinally-arranged bore through which a proximal end of the clamp screw shaft 537 is configured to extend. The outer idler gear 539 also includes outer circumferential gear teeth.

FIG. 4(b) also illustrate a combination bevel/spur gear component 541. The combination bevel/spur gear component 541 is configured to be rotatably mounted at its distal end 5411 within a correspondingly-sized and shaped orifice in the cartridge housing coupling 535. In addition, the combination bevel/spur gear component 541 includes, along an intermediate region thereof, a spur gear 5412 having outer circumferential teeth. The outer circumferential teeth of the outer idler gear 539 are configured to meshingly engage with the outer circumferential teeth of the spur gear 5412 of the combination bevel/spur gear component 541. Also, the combination bevel/spur gear component 541 includes, at its proximal end, a bevel gear 5413.

FIG. 4(b) also illustrates a distal pivot housing 543. The distal pivot housing 543 has a pair of vertically-aligned bores 5431 at its proximal end. Also, the bevel gear 5413 at the distal end of the combination bevel/spur gear component 541, the outer idler gear 539, and the bevel gear 5331 at the distal end of the fire input bevel component 533 are each configured to reside within respective longitudinally-arranged orifices of the distal pivot housing 543. In addition, the distal pivot housing 543 includes a pair of longitudinally arranged orifices, each one of which is configured to receive a respective one of a pair of threaded screws 545a, 545b.

The distal pivot housing 543 has a suitably shaped slot at its distal end to receive a portion of distal articulation gear 547. The distal articulation gear 547 defines a central orifice and outer circumferential gear teeth that extend around at least a portion of the outer circumference of the distal articulation gear 547. A pair of idler bevel gears 549a, 549b are arranged on respective opposite upper and lower surfaces of the distal articulation gear. Each one of the pair of idler bevel gears 549a, 549b include a centrally-disposed orifice which is configured to be aligned with the centrally-disposed orifice of the distal articulation gear 547. A hinge pin 551 is configured to be received within the pair of vertically-aligned bores 5031 at the distal end of the proximal pivot housing 503, within the pair of vertically-aligned bores 5431 at the proximal end of the distal pivot housing 543, within the respective centrally-disposed orifices of each one of the pair of idler bevel gears 549a, 549b, and within the centrally-disposed orifice of the distal articulation gear 547.

Figure 4C:
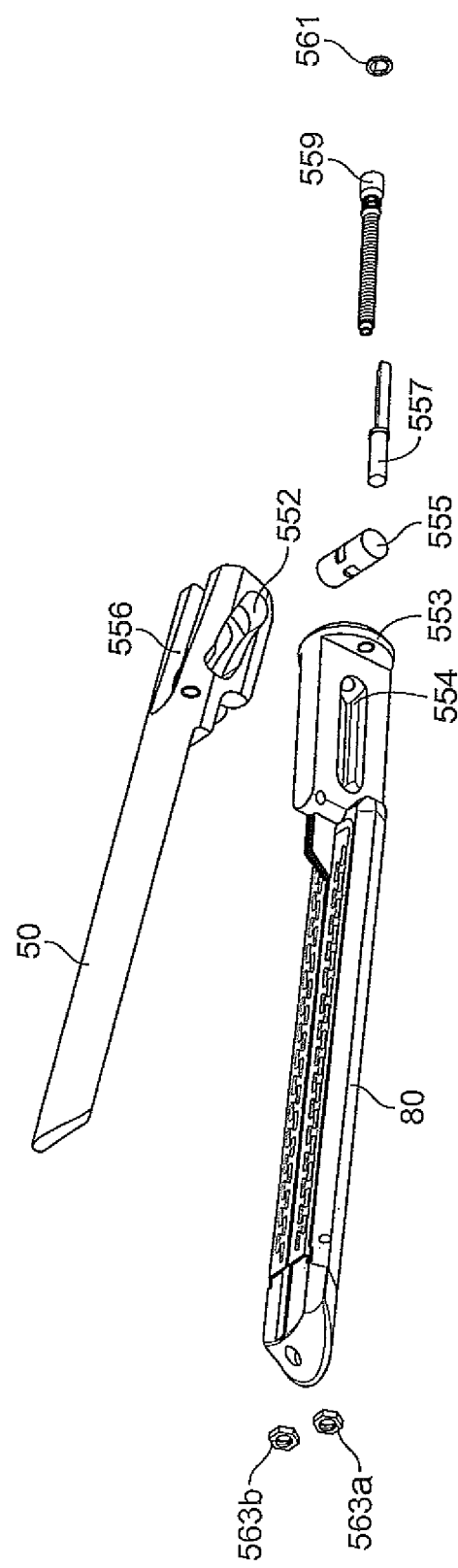
FIG. 4(c) is an exploded perspective view that illustrates a distal section of the distal assembly, according to the embodiment illustrated in FIG. 3(f)

As set forth above, FIG. 4(c) is an exploded perspective view that illustrates a distal section of the distal assembly, according to the embodiment illustrated in FIG. 3(f). FIG. 4(c) illustrates the first jaw 50 and a second jaw 80. A proximal portion of the first jaw 50 includes a first slot 552, which is extends along side surfaces of the proximal portion of the first jaw 50. Also, the proximal portion of the first jaw 50 includes a second slot 556, which extends along a top surface of the proximal portion of the first jaw 50. In addition, a proximal portion of the second jaw 80 is sized and shaped such that the proximal portion of the second jaw may fit within the second slot 556 of the first jaw 50, such that the proximal portion of the second jaw 80 resides within the proximal portion of the first jaw 50. In addition, the proximal portion of the second jaw includes a slot 554.

An inner shaft 555 is configured to fit within, and to be moveable in generally distal and proximal directions relative to, the first slot 552 of the first jaw 50 and the slot 554 of the second jaw 80. The inner shaft 555 includes a threaded bore that extends radially therethrough from a first circumferential surface to an opposite circumferential surface. A clamp screw 559 is configured to be received within a longitudinally-arranged orifice of the proximal end of the second jaw 80. The threaded bore of the inner shaft 555 is configured to receive a threaded distal end of the clamping screw 559. The clamping screw 559 also includes at its proximal end a longitudinally-arranged orifice, which is suitably sized and shaped so as to receive a correspondingly-sized and shaped distal end of the clamp screw shaft 537.

FIG. 4(c) also illustrates a firing shaft 557. A distal end of the firing shaft 557 includes a longitudinally-arranged orifice, which is suitably sized and shaped so as to receive a correspondingly-sized and shaped proximal end of, e.g., a threaded drive shaft (not shown) of the cutting and stapling element 104 that extends from a proximal end to a distal end of the second jaw 80. A proximal end of the firing shaft 557 has a smaller diameter than the distal end thereof, and is configured to be received longitudinally within the spring 531. Also, the proximal end of the firing shaft 557 has a cross-section size and shape that is suitable to be received within a correspondingly-sized and shaped, longitudinally-arranged bore at the distal end of the fire input bevel 533. A pair of nuts 563a, 563b are configured to engage respective ones of the threaded screws 545a, 545b, each of which extends through a respective one of the pair of longitudinally arranged orifices of the distal pivot housing 543 and through a respective one of a pair of longitudinally arranged orifices of the second jaw 80.

Figure 4D:
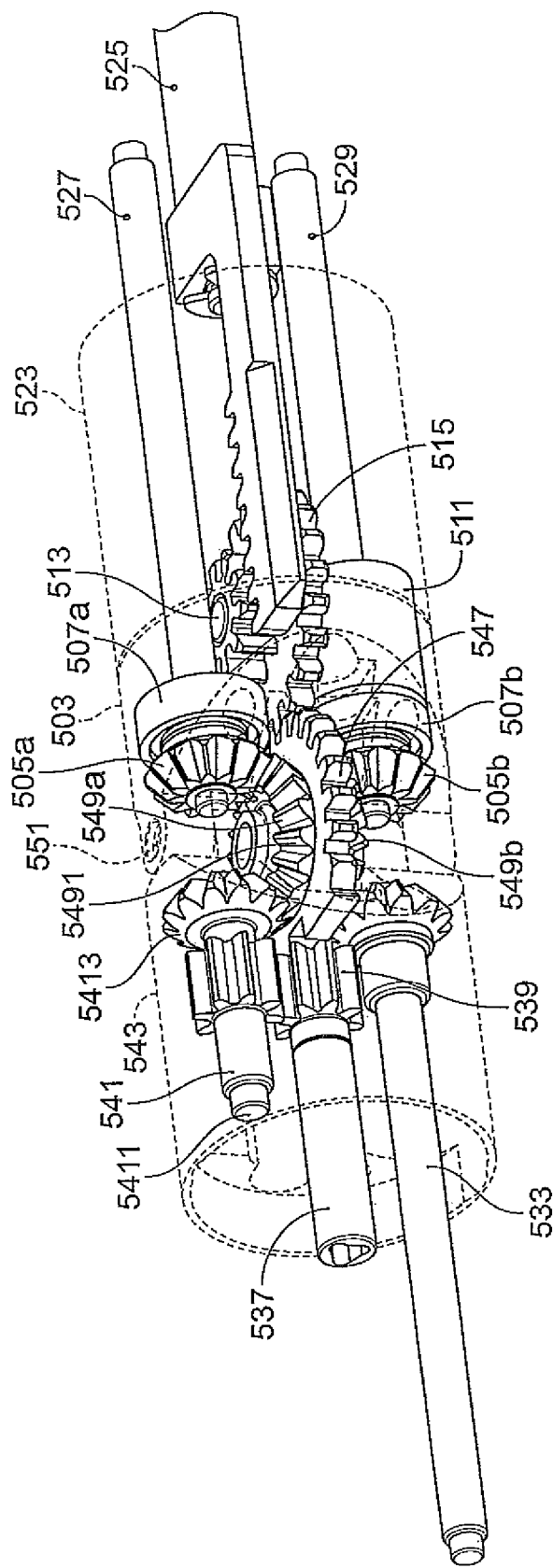
FIG. 4(d) is a side perspective view, partially in section, of the intermediate section of the distal assembly, according to the embodiment illustrated in FIG. 3(f)

FIG. 4(d) is a side perspective view, partially in section, of the distal assembly of the surgical device 11, as assembled, that shows additional details of the region at which the surgical device 11 is configured to articulate, according to the embodiment illustrated in FIG. 3(f). For example, FIG. 4(d) illustrates the proximal pivot housing 503 (in phantom) connected to the distal pivot housing 543 (also in phantom) by hinge pin 551 extending through the vertically-aligned orifices 5031 of the proximal pivot housing 503 and the vertically-aligned orifices 5431 of the distal pivot housing 543. The hinge pin 551 is also inserted through the central orifice of the distal articulation gear 547, and through the centrally-disposed orifices of the pair of idler bevel gears 549a, 549b that are arranged on respective opposite upper and lower surfaces of the distal articulation gear 547.

The clamp shaft 527 extends distally and extends through a longitudinally-arranged opening of the tube housing 523, through the longitudinally-arranged bores of the bevel thrust block 509 and ball bearing 507a, and engages the longitudinally-arranged orifice at the proximal end of the input bevel gear 505a. The gear teeth of the input bevel gear 505a are meshingly engaged with the gear teeth of the upper idler bevel gear 549a. Also meshingly engaged with the gear teeth of the upper idler bevel gear 549a are the gear teeth of the bevel gear 5413 of the combination bevel/spur gear component 541. The combination bevel/spur gear component 541 is rotatably mounted at its distal end 5411. In addition, the outer circumferential teeth of the spur gear 5412 of the combination bevel/spur gear component 541 are meshingly engaged with the outer circumferential teeth of the outer idler gear 539 which is mounted on the clamp screw shaft 537.

The fire shaft 529 extends distally and extends through a longitudinally-arranged opening of the tube housing 523, through the longitudinally-arranged bores of the bevel thrust block 511 and ball bearing 507b, and engages the longitudinally-arranged orifice at the proximal end of the input bevel gear 505b. The gear teeth of the input bevel gear 505b are meshingly engaged with the gear teeth of the lower idler bevel gear 549b. Also meshingly engaged with the gear teeth of the lower idler bevel gear 549b are the gear teeth of the bevel gear 5331 of the firing input bevel gear 533. The firing input bevel gear 533 extends distally to the firing shaft 557.

The articulation shaft 525 also extends distally and extends through a longitudinally-arranged opening of the tube housing 523. Mounted to the distal end of the articulation shaft 525 by clip 521 is rack 537, the teeth of which are engaged with the outer circumferential teeth of the rack gear 519. The rack gear 519 is positioned on an upper surface of the proximal articulation gear 515, and is rotatably mounted on the articulation thrust pin 513. The outer circumferential gear teeth of the proximal articulation gear 515 are meshingly engaged with the outer circumferential gear teeth of the distal articulation gear 547. The distal articulation gear 547 is rotationally fixed relative to the distal pivot housing 543.

Figure 4E:
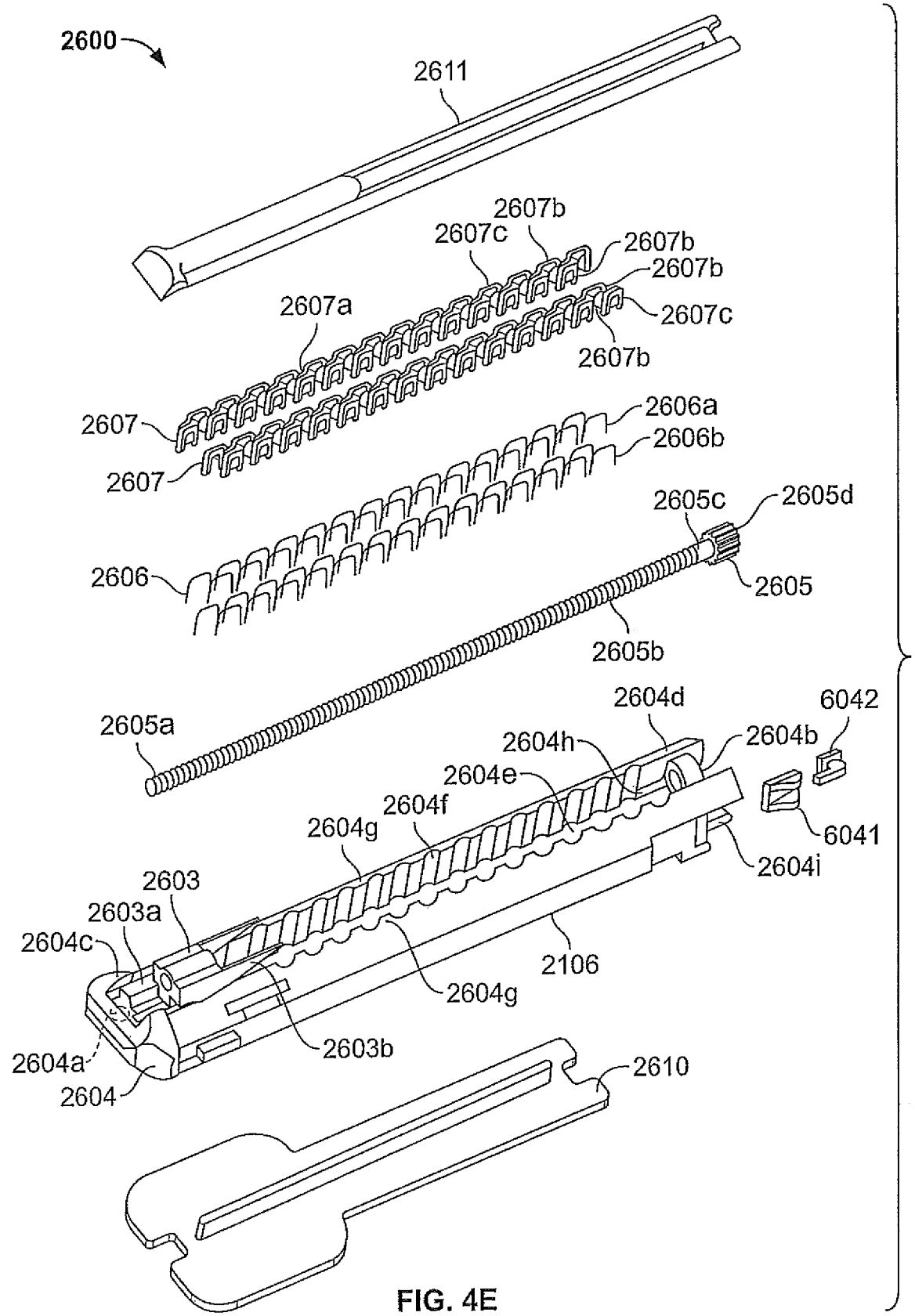
FIG. 4(e) is an exploded perspective view that illustrates a replaceable staple cartridge, according to an embodiment of the present invention.

As set forth above, the surgical device 11 may also include a cutting and stapling element 104. In an embodiment, the staple and cutting element 104 is a staple cartridge. FIG. 4(e) is an exploded view of a replaceable staple cartridge 2600. The replaceable staple cartridge 2600 is one type of stapling/cutting arrangement that may be employed as the cutting and stapling element 104 in the example embodiment of the present invention illustrated in, e.g., FIGS. 3(a) to 3(e). The replaceable staple cartridge 2600 includes a staple tray 2604. The staple tray 2604 has a slot 2604i at its proximal end 2604d in which the memory module 6041 is retained by a memory module retainer 6042. The memory module 6041 may store information as described, for example, in U.S. patent application Ser. No. 09/723,715, filed on Nov. 28, 2000, now issued as U.S. Pat. No. 6,793,652 on Sep. 21, 2004, U.S. patent application Ser. No. 09/836,781, filed on Apr. 17, 2001, U.S. patent application Ser. No. 09/887,789, filed on Jun. 22, 2001 and U.S. patent application Ser. No. 10/099,634, filed on Mar. 15, 2002, each of which is expressly incorporated herein by reference in its entirety. A wedge driver 2605 is configured to be rotatably disposed through a central channel 2604e of the staple tray 2604. Specifically, the wedge driver 2605 has a distal end 2605a that is configured to be rotatably mounted within a distal orifice 2604a of the staple tray 2604. The wedge driver 2605 also includes an externally threaded region 2605b, a non-threaded portion 2605c that rotatably extends through a proximal orifice 2604b in the proximal end 2604b of the staple tray 2604, and a proximally-facing opening 2605d at its proximal-most end for receiving the distal end of the clamp screw 559. The proximally-facing opening 2605d and the distal end of the clamp screw 559 are adapted for non-rotatable coupling relative to each other when the distal end of the clamp screw 559 is received, e.g., inserted, within the proximally-facing opening 2605d.

The replaceable staple cartridge 2600 also includes a wedge 2603 having an internally threaded bore 2603a. The externally threaded region 2605b of the wedge driver 2605 is configured to extend through the internally threaded bore 2603a of the wedge 2603. The threads of the internally threaded bore 2603a of the wedge 2603 match the threads of the externally threaded region 2605b of the wedge driver 2605. As is discussed further below, upon rotation of the wedge driver 2605, the wedge 2603 is moved between the distal end 2604c of the staple tray 2604 and the proximal end 2604d of the staple tray 2604 through a central channel 2604e.

The staple tray 2604 also includes a plurality of vertically-disposed slots 2604f in opposing walls 2604g of the central channel 2604e. On each side of the central channel 2604e, a staple pusher 2607 is configured to be slideably disposed within the slots 2604f. More specifically, each of the staple pushers 2607 has a top surface 2607a running longitudinally between two rows 2607b of staple pushing fingers 2607c. The staple pushing fingers 2607c are configured such that each staple pushing finger 2607c in the row 2607b that abuts the wall 2604g of the staple tray 2604 is retained within a corresponding slot 2604f of the wall 2604g so as to be vertically slideable therein. The staple pushing fingers 2607c are positioned over slots 2604h in the staple tray 2604. The slots 2604h in the staple tray 2604 house a plurality of fasteners, e.g., staples 2606. Each of the staples 2606 includes a butt 2606a and a pair of prongs 2606b.

The wedge 2603 also includes a pair of sloped edges 2603b that slideably engage respective top surfaces 2607a of the staple pushers 2607. When the wedge 2603 is moved from the distal end 2604c to the proximal end 2604d of the staple tray 2604 through the central channel 2604e, the pair of sloped edges 2603b of the wedge 2603 is configured to slideably engage the respective top surfaces 2607a of the staple pushers 2607 in order to successively push the staple pushing fingers 2607c of the staple pushers 2607 into, and thus the staples 2606 out of, the slots 2604h in the staple tray 2604. A cartridge top 2611 is configured to fit over the central channel 2604a of the staple tray 2604, while a staple retainer 2610 is configured to cover the clamping surface 106 of the staple tray 2604. Additional features, e.g., a blade 51, of the staple cartridge 2600 are described below in connection with FIG. 4(f), these features being described during operation of the surgical device 11.

Figure 4F:
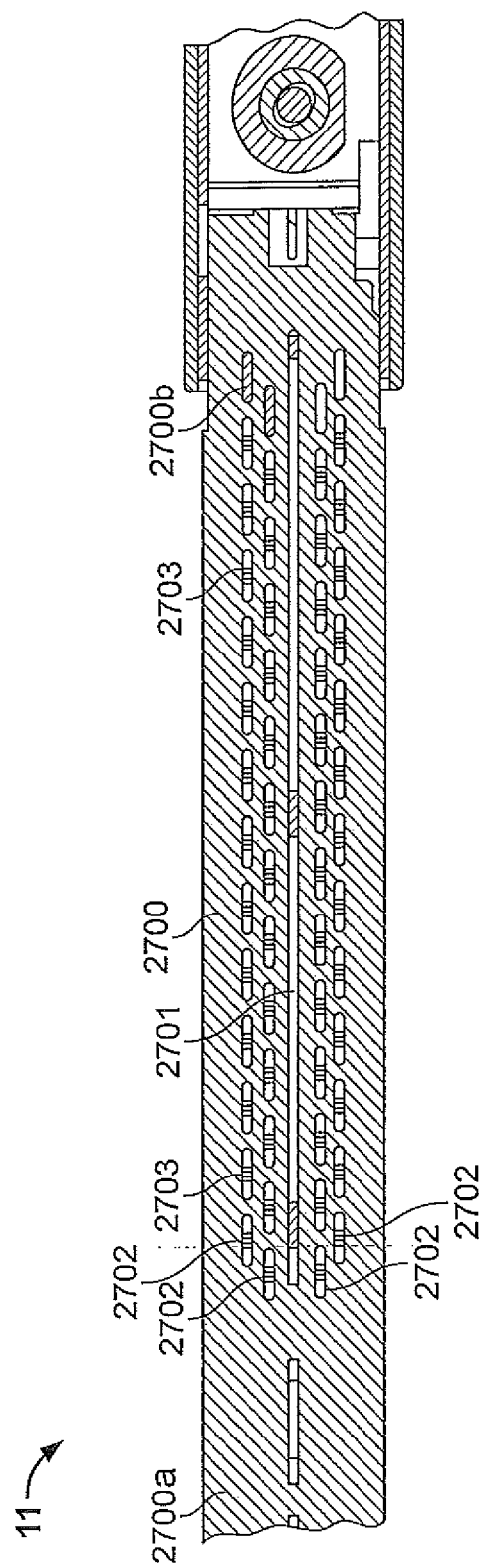
FIG. 4(f) is a bottom view of the anvil of a first jaw, according to an embodiment of the present invention.

FIG. 4(f) is a bottom view of the first jaw 50. The first jaw 50 includes an anvil member 2700 having a longitudinally-disposed slot 2701 that extends from a distal end to a proximal end of the anvil member 2700. The slot 2701 is aligned with the blade 51 of the second jaw 80 so that the blade 51 extends into and travels along the slot 2701 when the blade is moved from the distal end 80a to the proximal end 80b of the second jaw 80. The anvil member 2700 also includes a plurality of rows 2702 of staple guides 2703. The staple guides 2703 are configured to receive the prongs 2606b of the staples 2606 and to bend the prongs 2606b so as to close the staples 2606. When the surgical device 11 is in the closed position, the rows 2702 of the staple guides 2703 align with the slots 2604h of the staple tray 2604 in the second jaw 80.

As set forth above, the surgical device 11 of the present invention, in accordance with various embodiments thereof, may be configured to select and then perform various different functions during the course of a surgical procedure. Set forth below is an example procedure in which the surgical device 11 may be employed.

In operation, the jaw portion 11a is maintained in an initial position in which it is axially aligned with the shaft portion 11b, such as the position shown in FIG. 3(b). In this position, the surgical device 11 may be inserted, e.g., through a trocar, into a surgical site. Depending on the position of the incision and the tissue to be clamped, stapled and cut, the user may then operate the surgical device 11.

Once the surgical device 11 has been inserted within a patient, the shaft portion 11b may be rotated, e.g., the shaft portion 11b may be rotated relative to, and about the longitudinal axis D of, the handle 1103. Of course, it should be recognized that, in the example embodiment described herein, rotation of the shaft portion 11b relative to the handle 1103 also causes rotation of the jaw portion 11a disposed distally relative to the shaft portion 11b. In other embodiments, rotation may be achieved by the jaw portion 11a rotating relative to and about a longitudinal axis of the shaft portion 11b, or, in an embodiment in which the jaw portion 11a is coupled directly to the handle 1103, by the jaw portion 11a rotating relative to and about a longitudinal axis of the handle 1103. For the purposes of this application, the "shaft portion" is intended to refer to any portion of the component of the surgical device that is located distally relative to a handle.

Figure 5A:
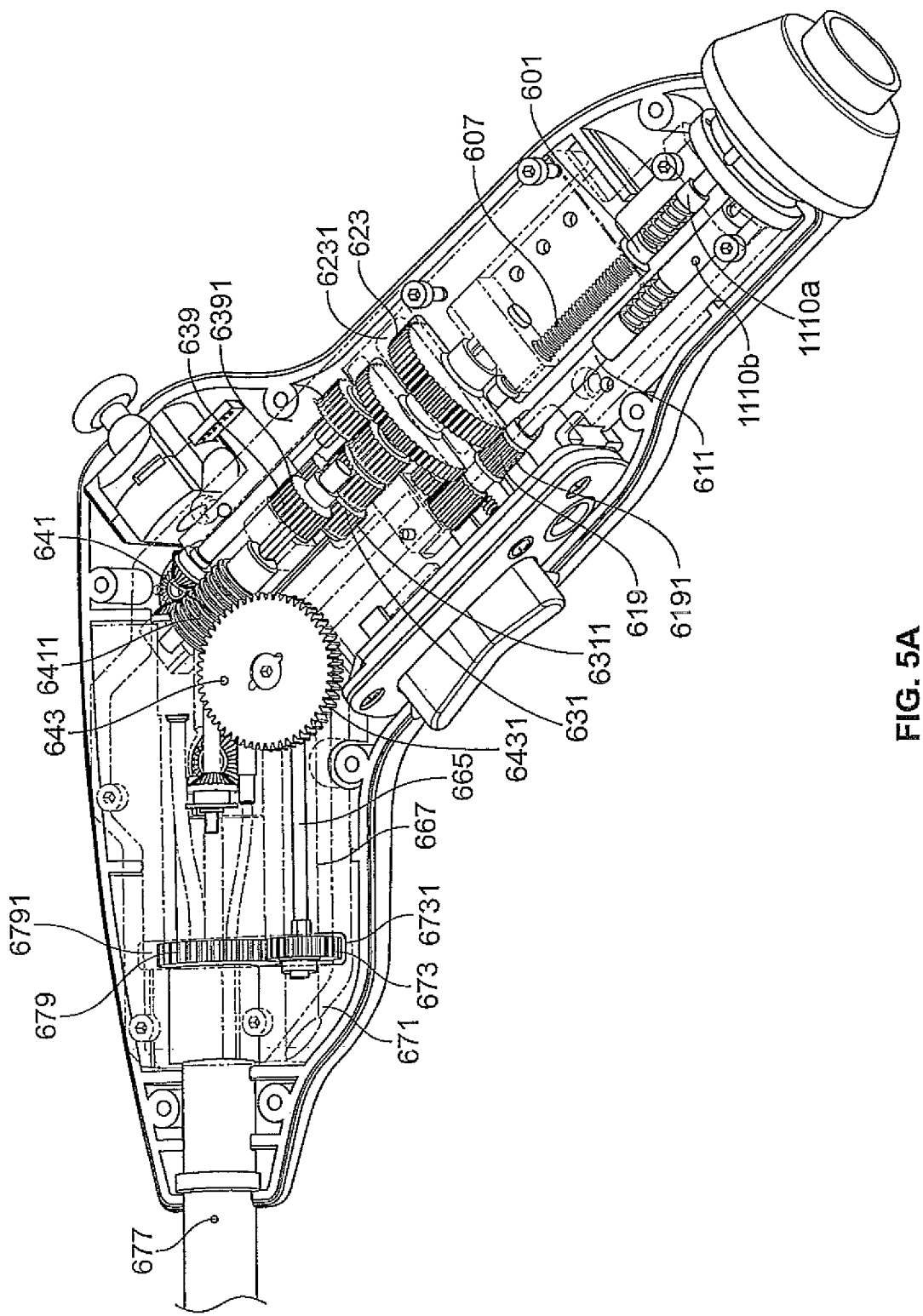
FIG. 5(a) is a side perspective view, partially in section, of the handle portion of the surgical device, and particularly the components of the handle portion that function to move, e.g., rotate, a shaft portion relative to, and about the longitudinal axis of, a handle, according to the embodiment illustrated in FIGS. 3(a) through 3(e)

In order to perform this first function, the surgical device 11 may be operated such that the function selector module 1110 is moved to a first functional position. As set forth above, in this first functional position, the function selector module 1110 causes engagement of the second rotatable drive shaft 1110b with a rotation driver 202. FIG. 5(a) is a side perspective view, partially in section, of the handle 1103 of the surgical device. In particular, FIG. 5(a) illustrates some of the components of the handle 1103 that form the rotation driver 202 and that function to rotate a shaft portion of the surgical device 11 relative to the handle 1103 about the longitudinal axis of the handle 1103, according to the embodiment illustrated in FIGS. 3(a) through 3(e). FIG. 5(a) illustrates some of these rotation driver 202 components in bold.

Referring now to FIG. 5(a), the first rotatable drive shaft 1110a is caused to rotate, e.g., such as by motor 96 (shown in FIG. 2(b)) in, e.g., a counter-clockwise direction (for the sake of simplicity, all references herein to a rotational direction, e.g., clockwise or counterclockwise, refer to a view from the proximal end of the surgical device towards the distal end of the surgical device 11, unless otherwise noted; furthermore, it should be recognized that, while the disclosure hereinbelow includes, for each of the components of the surgical device 11, various references to rotational directions in order to perform a specific function, these directions are merely exemplary because certain components may be differently configured, e.g., threaded portions may have a right-hand thread as opposed to a left-hand thread, etc., such that the rotational directions set forth herein may be reversed in order to perform the same below-described functions). Since the longitudinally-arranged bore of the first rotatable drive shaft 1110a and the proximal end of a selector shaft 601 are correspondingly sized and shaped, rotation of the first rotatable drive shaft 1110a in a counter-clockwise direction causes rotation of the selector shaft 601 in a counter-clockwise direction. By virtue of the threaded engagement of the threaded portion 607 of the selector shaft 601 within the threaded bore of the function selector block 609, rotation of the selector shaft 601 in a counter-clockwise direction causes the function selector block 609 to move to a distal-most, e.g., first, position, in which specific gears of the handle 1103 are engaged with each other. It should be recognized that, while the function selector block 609 may be moved to this distal-most, e.g., first, position by rotation of the selector shaft 601, in various other embodiments, the surgical device 11 may be configured such that the function selector block 609 is initially in this first position.

Once the function selector block 609 is moved to the first position, the second rotatable drive shaft 1110b may be caused to rotate, e.g., in a counter-clockwise direction, such as by motor 100 (shown in FIG. 2(b)). Since the longitudinally-arranged bore of the second rotatable drive shaft 1110b and the proximal end of the function shaft 611 are correspondingly sized and shaped, rotation of the second rotatable drive shaft 1110b in a counter-clockwise direction causes rotation of the function shaft 611 in a counter-clockwise direction. The input spur gear 619 of the second rotatable drive shaft 1110b also rotates. Due to the engagement of the outer circumferential gear teeth 6191 of the input spur gear 619 with the outer circumferential gear teeth 6231 of the rotation spur gear 623, rotation of the input spur gear 619 in a counter-clockwise direction causes rotation of the rotation spur gear 623 in a clockwise direction.

When the function selector block 609 is in the first position, the rotation spur gear 623 and the rotation spur gear 631 are engaged with the gear shaft 621 such that rotation of the rotation spur gear 623 in a clockwise direction causes rotation of the gear shaft 621 in a clockwise direction and also rotation of the rotation spur gear 631 in a clockwise direction. By virtue of the meshing engagement of the outer circumferential gear teeth 6311 of the rotation spur gear 631 with the outer circumferential gear teeth 6391 of the rotation spur gear 639, rotation of the rotation spur gear 631 in a clockwise direction causes rotation of the rotation spur gear 639 in a counter-clockwise direction.

Rotation of the rotation spur gear 639, which is mounted at an end of the rotation gear shaft 633, in a counter-clockwise direction causes rotation of the rotation gear shaft 633 in a counter-clockwise direction and rotation of the rotation worm gear 641, which is also mounted thereon, in a counter-clockwise direction. By virtue of the engagement of outer circumferential worm gear teeth 6411 of the rotation worm gear 641 with the outer circumferential gear teeth 6431 of the rotation gear 643, rotation of the rotation worm gear 641 in a counter-clockwise direction causes rotation of the rotation gear 643 in a clockwise direction (as viewed when looking into the page) about a pivot axis that is perpendicular to a longitudinal axis of the rotation gear shaft 633. Likewise, rotation of the rotation gear 643 in a clockwise direction causes rotation of the rotation miter gear 644, that is mounted thereon, in a clockwise direction. The miter gear teeth 6441 of the rotation miter gear 644 engage the miter gear teeth 6691 of the rotation miter gear 669, such that rotation of the rotation miter gear 644 in a clockwise direction causes rotation of the rotation miter gear 669 in a counter-clockwise direction.

The rotation miter gear 669 is mounted on the second rotation gear shaft 665, such that rotation of the rotation miter gear 669 in a counter-clockwise direction causes rotation of the second rotation gear shaft 665 in a counter-clockwise direction and of the rotation spur gear 673 in a counter-clockwise direction. By virtue of the meshing engagement of the outer circumferential gear teeth 6731 of the rotation spur gear 673 with the outer circumferential gear teeth 6791 of the rotating tube spur gear 679, rotation of the rotation spur gear 673 in a counter-clockwise direction causes rotation of the rotating tube spur gear 679 in a clockwise direction and also rotation of the rotating tube 677 mounted thereto in a clockwise direction. The rotation of the rotating tube 677 within a mouth 675 at the distal-most end of the handle 1103 provides the first above-described function of moving, e.g., rotating, the shaft portion 11b about a longitudinal axis of the handle 1103. Of course, the movement, e.g., rotation, in the opposite direction may also be accomplished by reversing the direction in which the above-described gears are caused to rotate.

Figure 6A:
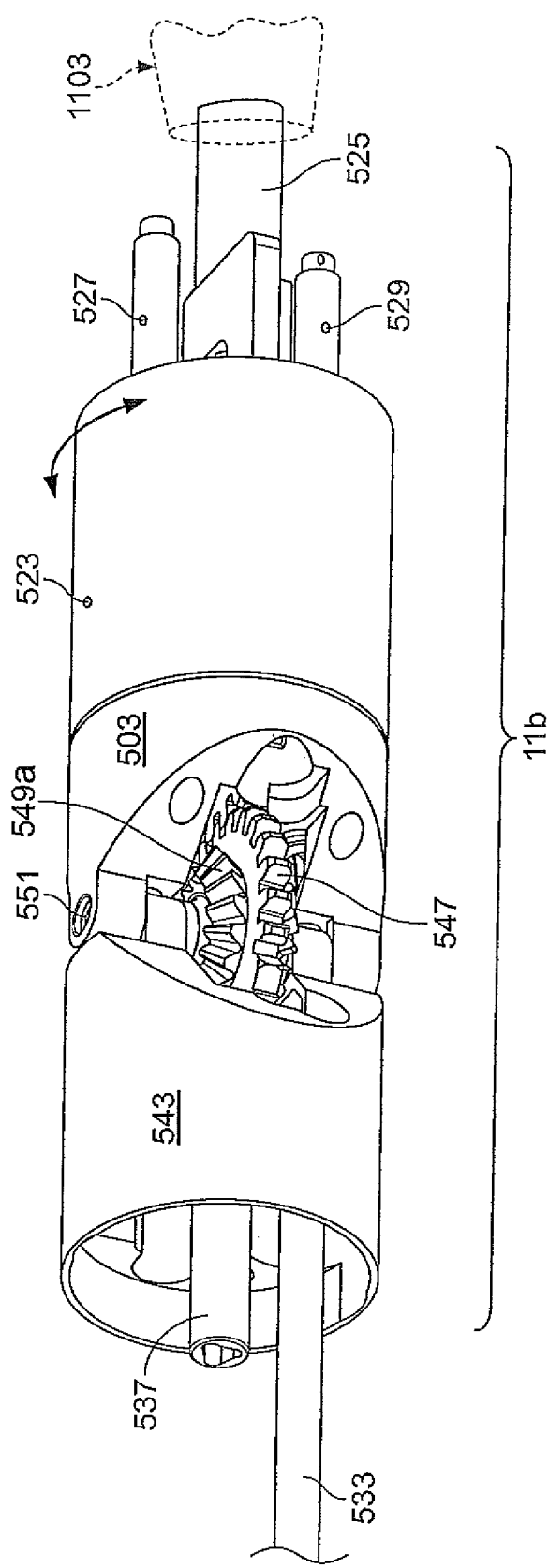
FIG. 6(a) is a side perspective view, partially in section, of the intermediate section of the distal portion of the surgical device, and particularly the components of the intermediate section that are moved, e.g., rotated, when a shaft portion is rotated relative to, and about a longitudinal axis of, the handle, according to the embodiment illustrated in FIGS. 3(f) and 4(d)

FIG. 6(a) is a side perspective view, partially in section, of another section of the distal portion of the surgical device 11. In particular, FIG. 6(a) illustrates the rotation of the shaft portion 11b of the surgical device 11 about the longitudinal axis of the handle 1103, according to an embodiment of the present invention.

Figure 5B:
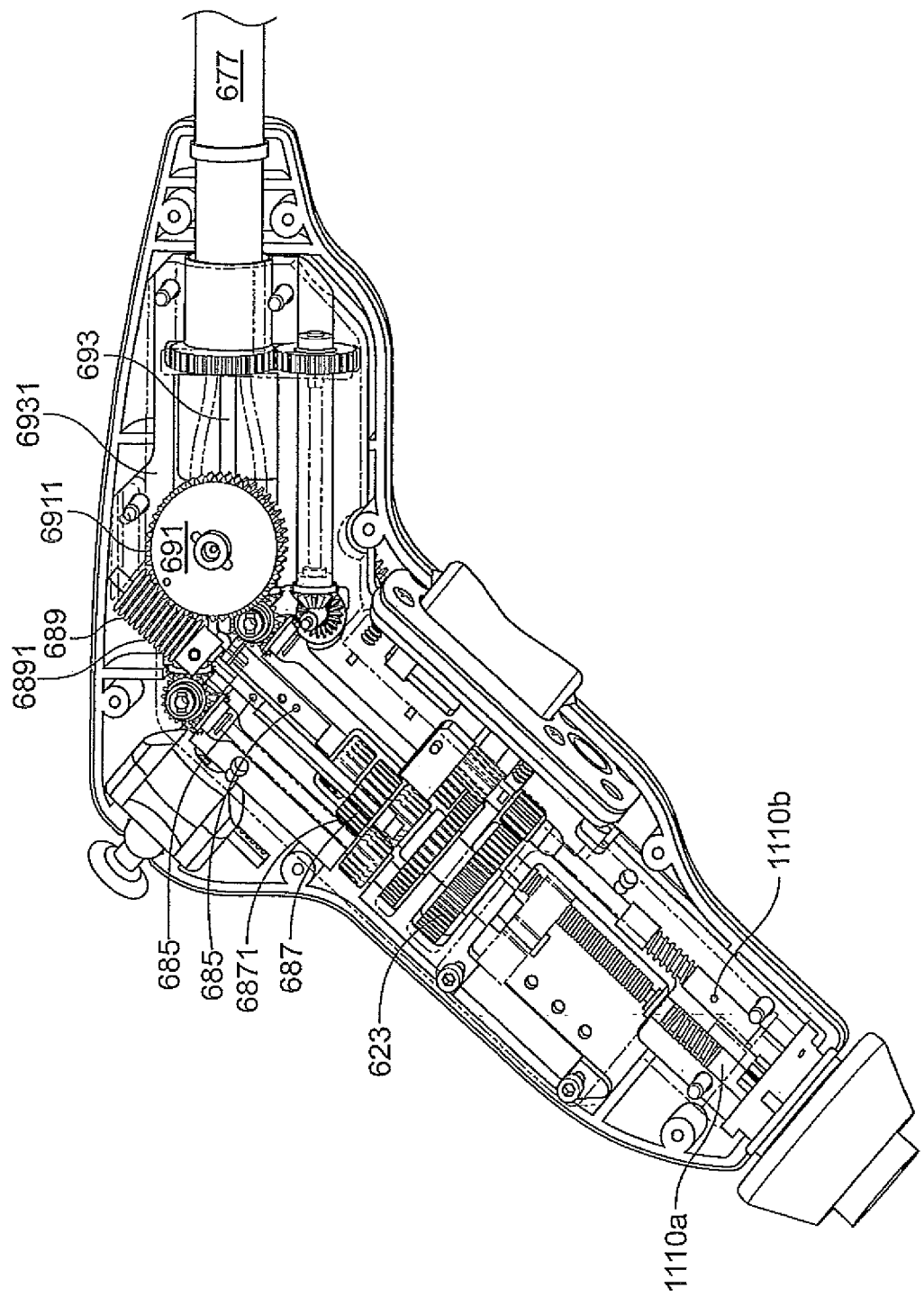
FIG. 5(b) is a side perspective view, partially in section, of the handle portion of the surgical device, and particularly the components of the handle portion that function to move, e.g., articulate, a jaw portion relative to a shaft portion, according to the embodiment illustrated in FIGS. 3(a) through 3(e)
Figure 5C:
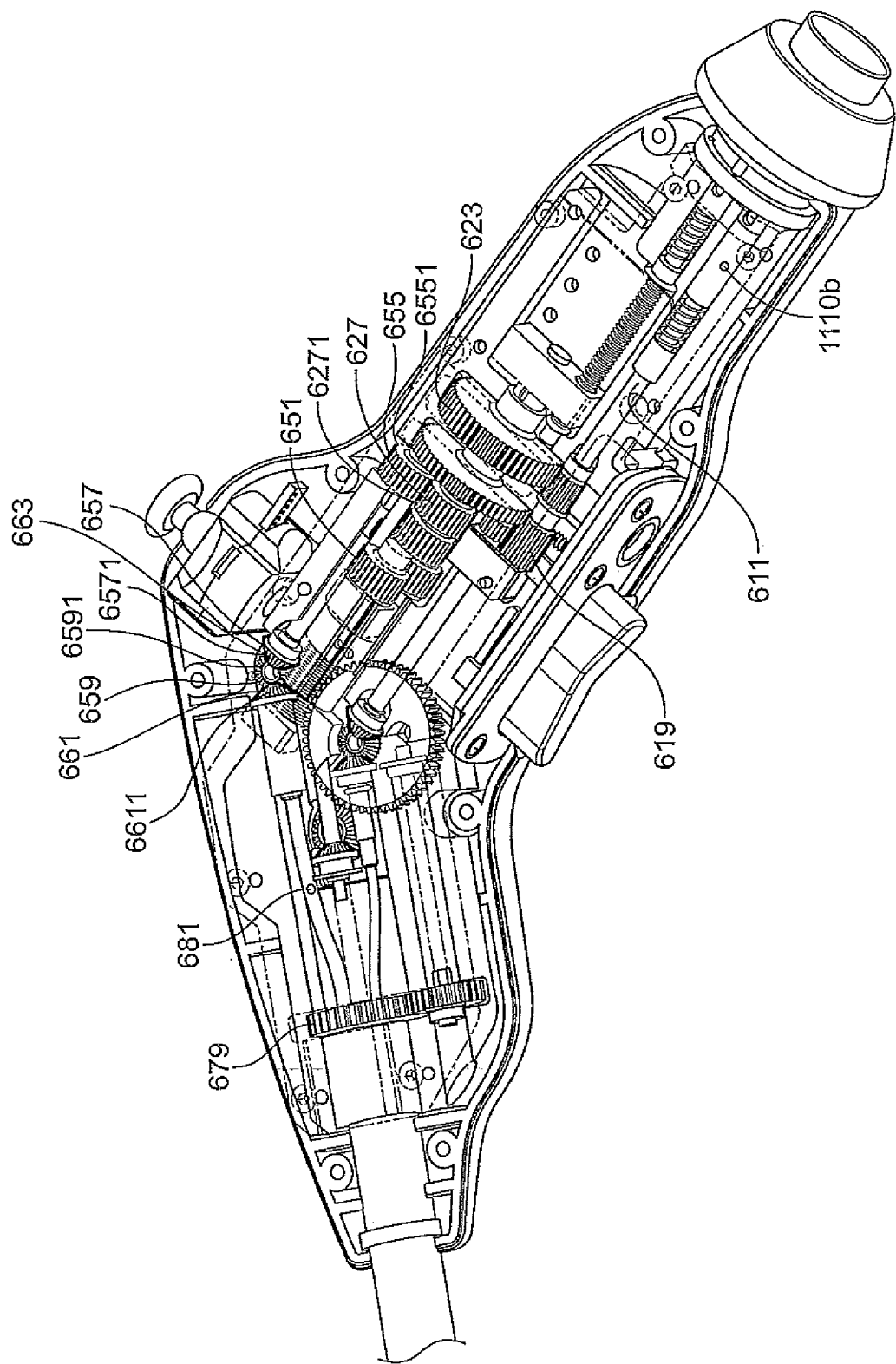
FIG. 5(c) is a side perspective view, partially in section, of the handle portion of the surgical device, and particularly the components of the handle portion that function to move, e.g., clamp by opening and closing, a first jaw relative to a second jaw, according to the embodiment illustrated in FIGS. 3(a) through 3(e)
Figure 5D:
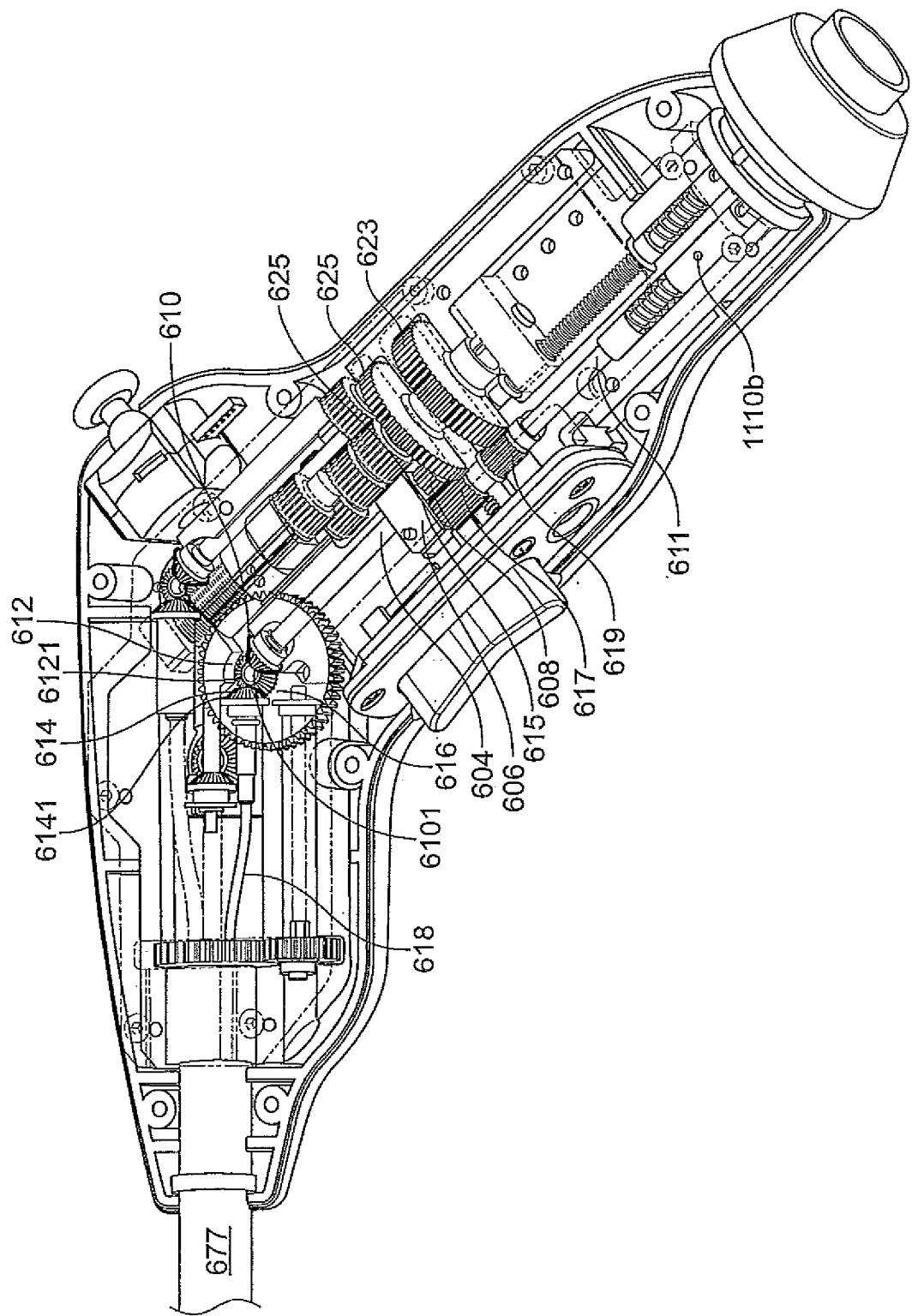
FIG. 5(d) is a side perspective view, partially in section, of the handle portion of the surgical device, and particularly the components of the handle portion that function to move a cutting and/or stapling element, e.g., to drive a staple pushing element and/or cutting blade through a section of tissue, according to the embodiment illustrated in FIGS. 3(a) through 3(e)

Once the shaft portion 11b has been rotated relative to the handle 1103, the surgical device 11 may be employed to move the jaw portion 11a relative to the shaft portion 11b, e.g., to pivot the jaw portion 11a about axis B relative to the shaft portion 11b. In order to perform this second function, the surgical device 11 may be operated such that the function selector module 1110 is moved to a second functional position. As set forth above, in this second functional position, the function selector module 1110 causes engagement of the second rotatable drive shaft 1110b with an articulation driver 201. FIG. 5(b) is a side perspective view, partially in section, of the handle 1103 of the surgical device. In particular, FIG. 5(b) illustrates some of the components of the handle 1103 that form the articulation driver 201 and that function to move, e.g., articulate, the jaw portion 11a relative to the shaft portion 11b, according to the embodiment illustrated in FIGS. 3(a) through 3(e). FIG. 5(b) illustrates some of these articulation driver 201 components in bold.

Referring to FIG. 5(b), the first rotatable drive shaft 1110a is again caused to rotate, e.g., in a clockwise direction, such as by motor 96 (shown in FIG. 2(b)). Since the longitudinally-arranged bore of the first rotatable drive shaft 1110a and the proximal end of a selector shaft 601 are correspondingly sized and shaped, rotation of the first rotatable drive shaft 1110a in a clockwise direction causes rotation of the selector shaft 601 in a clockwise direction. By virtue of the threaded engagement of the threaded portion 607 of the selector shaft 601 within the threaded bore of the function selector block 609, rotation of the selector shaft 601 causes the function selector block 609 to move proximally to, e.g., a second position, in which specific gears of the handle 1103 are engaged with each other.

Once the function selector block 609 is moved to the second position, the second rotatable drive shaft 1110b is caused to rotate, e.g., in a counter-clockwise direction, such as by motor 100 (shown in FIG. 2(b)). Since the longitudinally-arranged bore of the second rotatable drive shaft 1110b and the proximal end of the function shaft 611 are correspondingly sized and shaped, rotation of the second rotatable drive shaft 1110b in a counter-clockwise direction causes rotation of the function shaft 611 in a counter-clockwise direction. The fire spur gear 617 of the second rotatable drive shaft 1110b is also caused to rotate in a counter-clockwise direction. Due to the engagement of the outer circumferential gear teeth 6191 of the input spur gear 619 with the outer circumferential gear teeth 6231 of the articulation spur gear 623, rotation of the input spur gear 619 in a counter-clockwise direction causes rotation of the articulation spur gear 623 in a clockwise direction.

When the function selector block 609 is in the second position, the rotation spur gear 623 and the articulation spur gear 629 are engaged with the gear shaft 621 such that rotation of the rotation spur gear 623 in a clockwise direction causes rotation of the gear shaft 621 in a clockwise direction and also rotation of the articulation spur gear 629 in a clockwise direction. By virtue of the meshing engagement of the outer circumferential gear teeth 6291 of the articulation spur gear 629 with the outer circumferential gear teeth 6871 of the articulation spur gear 687, rotation of the articulation spur gear 629 in a clockwise direction causes rotation of the articulation spur gear 687 in a counter-clockwise direction.

Rotation of the articulation spur gear 687, which is mounted at an end of the articulation gear shaft 685, in a counter-clockwise direction causes rotation of the articulation gear shaft 685 in a counter-clockwise direction and of the articulation worm gear 689, which is also mounted thereon, in a counter-clockwise direction. By virtue of the engagement of outer circumferential worm gear teeth 6891 of the articulation worm gear 689 with the outer circumferential gear teeth 6911 of the articulation gear 691, rotation of the articulation worm gear 689 in a counter-clockwise direction causes rotation of the articulation gear 691 in a counter-clockwise direction (when viewed into the page) about a pivot axis that is perpendicular to a longitudinal axis of the articulation gear shaft 685. Likewise, rotation of the articulation gear 691 in a counter-clockwise direction causes rotation of the articulation miter gear 692, that is mounted thereon, in a counter-clockwise direction. The miter gear teeth 6921 of the articulation miter gear 692 engage the miter gear teeth 6961 of the articulation miter gear 696, such that rotation of the articulation miter gear 692 in a counter-clockwise direction causes rotation of the articulation miter gear 696 in a counter-clockwise direction.

The articulation miter gear 696 is mounted on the second articulation gear shaft 693. By virtue of the threaded engagement between the threaded rod portion 695 of the second articulation gear shaft 693 and the interior threaded bore of the articulation miter gear 696, rotation of the articulation miter gear 696 in a counter-clockwise direction causes the second articulation gear shaft 693 to move, e.g., distally (depending on the direction of threads on the second articulation gear shaft 693).

Figure 6B:
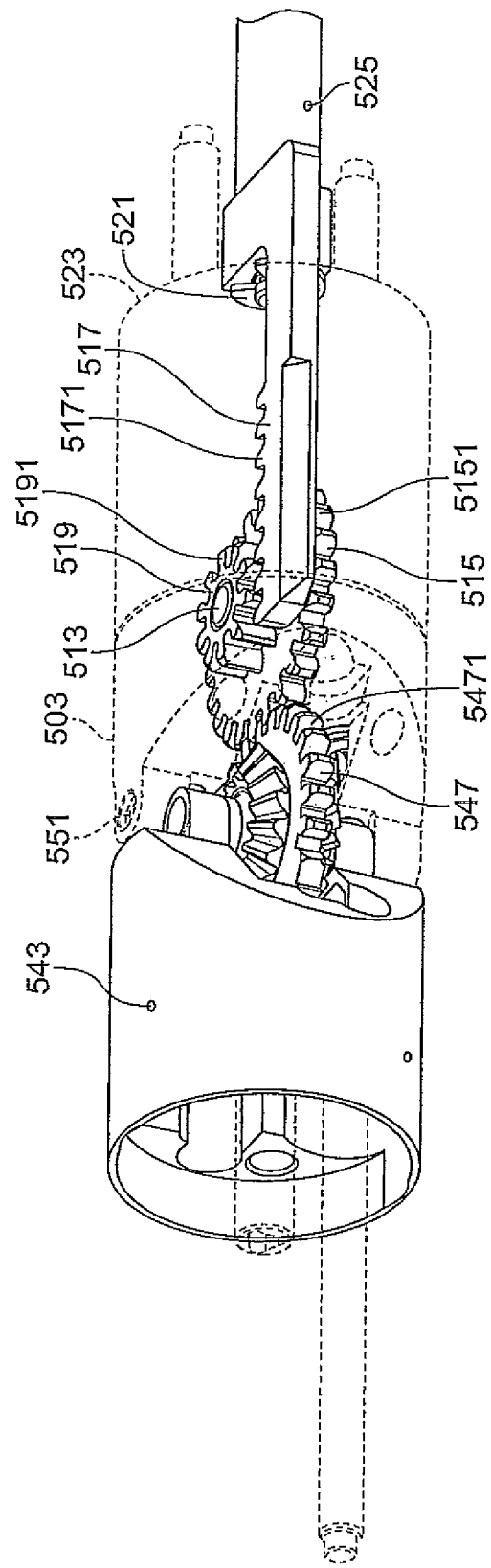
FIG. 6(b) is a side perspective view, partially in section, of the intermediate section of the distal portion of the surgical device, and particularly the components of the intermediate section that function to move, e.g., articulate, a jaw portion relative to a shaft portion, according to the embodiment illustrated in FIGS. 3(f) and 4(d)
Figure 6C:
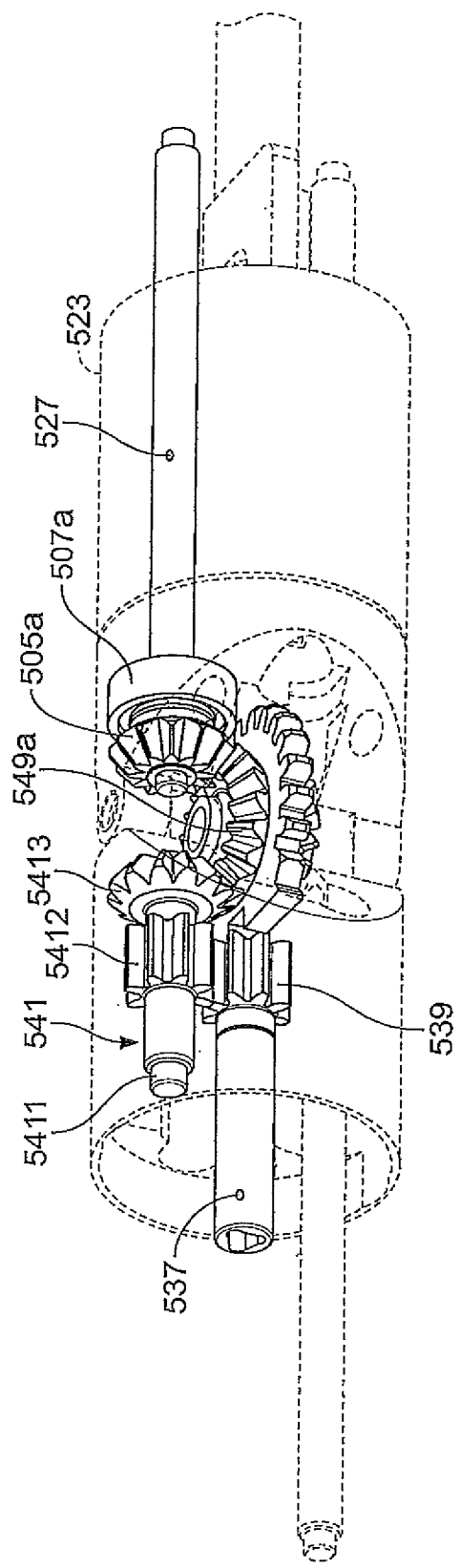
FIG. 6(c) is a side perspective view, partially in section, of the intermediate section of the distal portion of the surgical device, and particularly the components of the intermediate section that function to move, e.g., clamp by opening and closing, a first jaw relative to a second jaw, according to the embodiment illustrated in FIGS. 3(f) and 4(d)
Figure 6D:
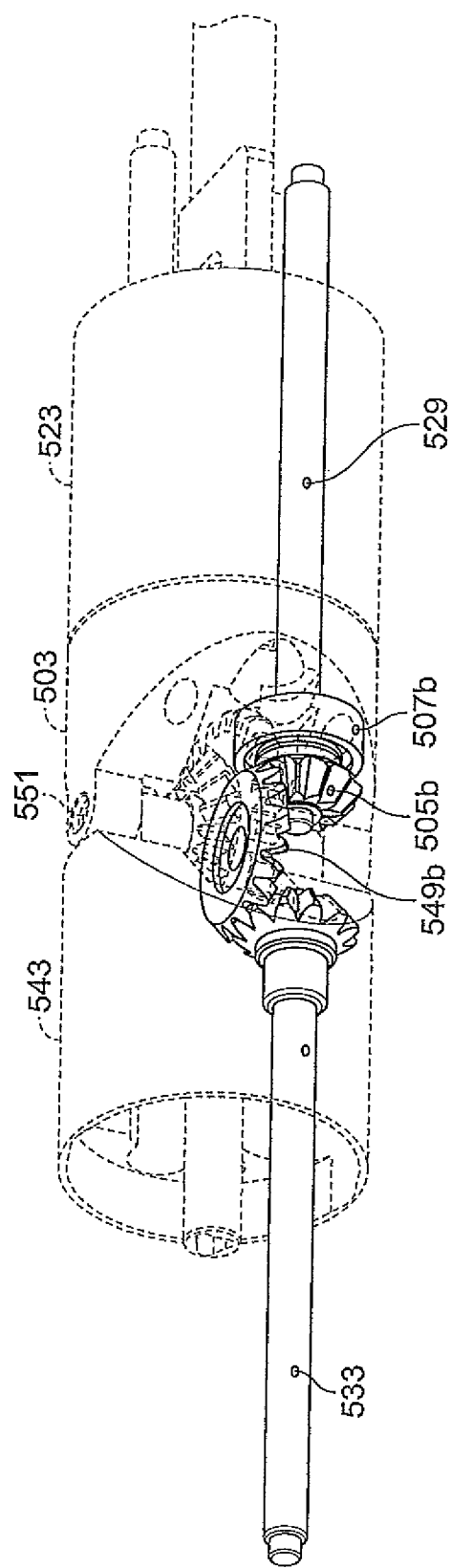
FIG. 6(d) is a side perspective view, partially in section, of the intermediate section of the distal portion of the surgical device, and particularly the components of the intermediate section that function to move a cutting and/or stapling element, e.g., to drive a staple pushing element and/or cutting blade through a section of tissue, according to the embodiment illustrated in FIGS. 3(f) and 4(d)

FIG. 6(b) is a side perspective view, partially in section, of another section of the distal portion of the surgical device 11. In particular, FIG. 6(b) illustrates additional components of the surgical device 11 that function to move, e.g., articulate, the jaw portion 11*a* relative to the shaft portion 11*b*, according to the embodiment illustrated in FIGS. 3(*f*) and 4(*d*). FIG. 6(*b*) illustrates some of these articulation driver 201 components in bold.

As shown in FIG. 6(*b*), movement of the articulation shaft 525 distally causes the rack 517 to also move distally. By virtue of the engagement of the teeth of the rack 517 with the teeth of the rack gear 519, distal movement of the rack 517 causes the rack gear 519, and the proximal articulation gear 515, to rotate in a clockwise direction (when viewed from above). Also, by virtue of the engagement of the outer circumferential teeth of the proximal articulation gear 515 with the outer circumferential teeth of the distal articulation gear 547, rotation of the proximal articulation gear 515 in a clockwise direction causes rotation of the distal articulation gear 547 in a counter-clockwise direction. Since the distal articulation gear 547 is rotationally fixed relative to the distal pivot housing 543, rotation of the distal articulation gear 547 in a counter-clockwise direction causes the jaw portion 11*a* to move, e.g., articulate, in a counter-clockwise direction (when viewed from above) relative to the shaft portion 11*b* about the hinge pin 551, which defines in this example embodiment the axis B shown in FIG. 2(*b*). Of course, the movement, e.g., articulation, in the opposite direction may also be accomplished by reversing the direction in which the above-described gears are caused to rotate.

Once the jaw portion 11*a* has been articulated about axis B relative to the shaft portion 11*b*, the jaws 50, 80 may be moved, e.g., opened, so as to enable a section of tissue to be disposed therebetween. In order to perform this third function, the surgical device 11 may be operated such that the function selector module 1110 is moved to a third functional position. As set forth above, in this third functional position, the function selector module 1110 causes engagement of the second rotatable drive shaft 1110*b* with a clamping driver 88. FIG. 5(*c*) is a side perspective view, partially in section, of the handle 1103 of the surgical device 11. In particular, FIG. 5(*c*) illustrates some of the components of the handle 1103 that form the clamping driver 88 and that function to move, e.g., to open, the first jaw 50 relative to the second jaw 80, according to the embodiment illustrated in FIGS. 3(*a*) through 3(*e*). FIG. 5(*c*) illustrates some of these clamping driver 88 components in bold.

Referring to FIG. 5(*c*), the first rotatable drive shaft 1110*a* is again caused to rotate, e.g., in a clockwise direction, such as by motor 96 (shown in FIG. 2(*b*)). Since the longitudinally-arranged bore of the first rotatable drive shaft 1110*a* and the proximal end of a selector shaft 601 are correspondingly sized and shaped, rotation of the first rotatable drive shaft 1110*a* in a clockwise direction causes rotation of the selector shaft 601 in a clockwise direction. By virtue of the threaded engagement of the threaded portion 607 of the selector shaft 601 within the threaded bore of the function selector block 609, rotation of the selector shaft 601 in a clockwise direction causes the function selector block 609 to move proximally to, e.g., a third position, in which specific gears of the handle 1103 are engaged with each other.

Once the function selector block 609 is moved to the third position, the second rotatable drive shaft 1110*b* is caused to rotate, e.g., in a counter-clockwise direction, such as by motor 100 (shown in FIG. 2(*b*)). Since the longitudinally-arranged bore of the second rotatable drive shaft 1110*b* and the proximal end of the function shaft 611 are correspondingly sized and shaped, rotation of the second rotatable drive shaft 1110*b* in a counter-clockwise direction causes rotation of the function shaft 611 in a counter-clockwise direction. The input spur gear 619 of the second rotatable drive shaft 1110*b* is also caused to rotate in a counter-clockwise direction. Due to the engagement of the outer circumferential gear teeth 6191 of the input spur gear 619 with the outer circumferential gear teeth 6231 of the rotation spur gear 623, rotation of the input spur gear 619 in a counter-clockwise direction causes rotation of the rotation spur gear 623 in a clockwise direction.

When the function selector block 609 is in the third position, the rotation spur gear 623 and the clamping spur gear 627 are engaged with the gear shaft 621 such that rotation of the rotation spur gear 623 in a clockwise direction causes rotation of the gear shaft 621 in a clockwise direction and also rotation of the clamping spur gear 627 in a clockwise direction. By virtue of the meshing engagement of the outer circumferential gear teeth 6271 of the clamping spur gear 627 with the outer circumferential gear teeth 6551 of the clamping spur gear 655, rotation of the clamping spur gear 627 in a clockwise direction causes rotation of the clamping spur gear 655 in a counter-clockwise direction. Clamping spur gear 655 is mounted at an end of the clamping gear shaft 651 that has the first clamping miter gear 657 mounted at its opposite end, such that rotation of the clamping spur gear 655 in a counter-clockwise direction also causes rotation of the clamping gear shaft 651 in a counter-clockwise direction and the first clamping miter gear 657 in a counter-clockwise direction.

The miter gear teeth 6571 of the first clamping miter gear 657 engage the miter gear teeth 6591 of the second clamping miter gear 659, such that rotation of the first clamping miter gear 657 in a counter-clockwise direction causes rotation of the second clamping miter gear 659 in a counter-clockwise direction (when viewed into the page) about an axis that is perpendicular to the longitudinal axis of the clamping gear shaft 651. Likewise, the miter gear teeth 6591 of the second clamping miter gear 659 engage the miter gear teeth 6611 of the third clamping miter gear 661, such that rotation of the second clamping miter gear 659 in a counter-clockwise direction causes rotation of the third clamping miter gear 661 in a clockwise direction. The third clamping miter gear 661 is mounted at the proximal end of the second clamping gear shaft 681 such that rotation of the third clamping miter gear 661 in a clockwise direction causes rotation of the second clamping gear shaft 681 in a clockwise direction.

FIG. 6(*c*) is a side perspective view, partially in section, of another section of the distal portion of the surgical device 11. In particular, FIG. 6(*c*) illustrates additional components of the surgical device 11 that function to move, e.g., open, the first jaw 50 relative to the second jaw 80, according to the embodiment illustrated in FIGS. 3(*f*) and 4(*d*). FIG. 6(*c*) illustrates some of these clamping driver 88 components in bold.

As set forth above, the second clamping gear shaft 681 extends distally through the rotating tube 677 to eventually form the clamp shaft 527. The rotation of the clamp shaft 527 in a clockwise direction causes rotation of the input bevel gear 505*a* in a clockwise direction. By virtue of the meshing engagement of the gear teeth of the input bevel gear 505*a* with the gear teeth of the upper idler bevel gear 549*a*, rotation of the input bevel gear 505*a* in a clockwise direction about the longitudinal axis of the clamping shaft 527 causes rotation of the upper idler bevel gear 549*a* in a clockwise direction (when viewed from above). Likewise, by virtue of the meshing engagement of the gear teeth of the upper idler bevel gear 549*a* with the gear teeth of the bevel gear 5413 of the combination bevel/spur gear component 541, rotation of the upper idler bevel gear 549*a* in a clockwise direction about the longitudinal axis of the hinge pin 551 causes rotation of the bevel gear 5413 of the combination bevel/spur gear component 541 in a counter-clockwise direction, along with rotation of the spur gear mounted on the combination bevel/spur gear component 541 in a counter-clockwise direction. Since the outer circumferential teeth of the spur gear of the combination bevel/spur gear component 541 are meshingly engaged with the outer circumferential teeth of the outer idler gear 539, rotation of the spur gear of the combination bevel/spur gear component 541 in a counter-clockwise direction causes rotation of the outer idler gear 539 in a clockwise direction and rotation of the clamp screw shaft 537, on which it is mounted, in a counter-clockwise direction.

Referring now to FIG. 4(*c*), the clamp screw 559, which is mounted on the distal end of the clamp screw shaft 537, is also caused to turn in a counter-clockwise direction. The inner shaft 555 is threadedly engaged with the outer threads of the clamp screw 559, such that rotation of the clamp screw 559 in a counter-clockwise direction causes the inner shaft 555 to move in a proximal direction within the slots 552 and 554 of the first and second jaws 50 and 80, respectively. This proximal movement of the inner shaft 555 allows the first and second jaws to move, e.g., open, relative to each other. Additional details of this clamping arrangement may be found, for example, in U.S. patent application Ser. No. 11/191,851, entitled "Surgical Device," filed Jul. 27, 2005, the disclosure of which is hereby incorporated by reference in its entirety.

Once the first and second jaws 50, 80 have been opened to a desired position relative to each other, and once a section of tissue desired to be operated on is satisfactorily positioned between the first and second jaws 50, 80 of the surgical device 11, the first and second jaws 50, 80 are closed so as to clamp the section of tissue therebetween.

In order to close the first and second jaws 50, 80 relative to each other, the function selector module 1110 may remain in the third functional position. As set forth above, in this third functional position, the function selector module 1110 causes engagement of the second rotatable drive shaft 1110*b* with the clamping driver 88.

Referring to FIG. 5(*c*), with the function selector block 609 in the third position, the second rotatable drive shaft 1110*b* is caused to rotate, e.g., in a clockwise direction, such as by motor 100 (shown in FIG. 2(*b*)). Since the longitudinally-arranged bore of the second rotatable drive shaft 1110*b* and the proximal end of the function shaft 611 are correspondingly sized and shaped, rotation of the second rotatable drive shaft 1110*b* in a clockwise direction causes rotation of the function shaft 611 in a clockwise direction. The input spur gear 619 of the second rotatable drive shaft 1110*b* is also caused to rotate in a clockwise direction. Due to the engagement of the outer circumferential gear teeth 6191 of the input spur gear 619 with the outer circumferential gear teeth 6231 of the rotation spur gear 623, rotation of the input spur gear 619 in a clockwise direction causes rotation of the rotation spur gear 623 in a counter-clockwise direction.

Again, when the function selector block 609 is in the third position, the rotation spur gear 623 and the clamping spur gear 627 are engaged with the gear shaft 621 such that rotation of the rotation spur gear 623 in a counter-clockwise direction causes rotation of the gear shaft 621 in a counter-clockwise direction and also rotation of the clamping spur gear 627 in a counter-clockwise direction. By virtue of the meshing engagement of the outer circumferential gear teeth 6271 of the clamping spur gear 627 with the outer circumferential gear teeth 6551 of the clamping spur gear 655, rotation of the clamping spur gear 627 in a counter-clockwise direction causes rotation of the clamping spur gear 655 in a clockwise direction. Clamping spur gear 655 is mounted at an end of the clamping gear shaft 651, that has the first clamping miter gear 657 mounted at its opposite end, such that rotation of the clamping spur gear 655 in a clockwise direction also causes rotation of the clamping gear shaft 651 in a clockwise direction and the first clamping miter gear 657 in a clockwise direction.

The miter gear teeth 6571 of the first clamping miter gear 657 engage the miter gear teeth 6591 of the second clamping miter gear 659, such that rotation of the first clamping miter gear 657 in a clockwise direction causes rotation of the second clamping miter gear 659 in a clockwise direction (when viewed into the page) about an axis that is perpendicular to the longitudinal axis of the clamping gear shaft 651. Likewise, the miter gear teeth 6591 of the second clamping miter gear 659 engage the miter gear teeth 6611 of the third clamping miter gear 661, such that rotation of the second clamping miter gear 659 in a clockwise direction causes rotation of the third clamping miter gear 661 in a counter-clockwise direction. The third clamping miter gear 661 is mounted at the proximal end of the second clamping gear shaft 681 such that rotation of the third clamping miter gear 661 in a counter-clockwise direction causes rotation of the second clamping gear shaft 681 in a counter-clockwise direction.

Referring next to FIG. 6(*c*), the rotation of the clamp shaft 527 in a counter-clockwise direction causes rotation of the input bevel gear 505*a* in a counter-clockwise direction. By virtue of the meshing engagement of the gear teeth of the input bevel gear 505*a* with the gear teeth of the upper idler bevel gear 549*a*, rotation of the input bevel gear 505*a* in a counter-clockwise direction about the longitudinal axis of the clamping shaft 527 causes rotation of the upper idler bevel gear 549*a* in a counter-clockwise direction (when viewed from above). Likewise, by virtue of the meshing engagement of the gear teeth of the upper idler bevel gear 549*a* with the gear teeth of the bevel gear 5413 of the combination bevel/spur gear component 541, rotation of the upper idler bevel gear 549*a* in a counter-clockwise direction about the longitudinal axis of the hinge pin 551 causes rotation of the bevel gear 5413 of the combination bevel/spur gear component 541 in a clockwise direction, along with rotation of the spur gear mounted on the combination bevel/spur gear component 541 in a clockwise direction. Since the outer circumferential teeth of the spur gear of the combination bevel/spur gear component 541 are meshingly engaged with the outer circumferential teeth of the outer idler gear 539, rotation of the spur gear of the combination bevel/spur gear component 541 in a clockwise direction causes rotation of the outer idler gear 539 in a counter-clockwise direction and of the clamp screw shaft 537, on which it is mounted, in a counter-clockwise direction.

Referring now to FIG. 4(*c*), the clamp screw 559, which is mounted on the distal end of the clamp screw shaft 537, is also caused to turn in a counter-clockwise direction. The inner shaft 555 is threadedly engaged with the outer threads of the clamp screw 559, such that rotation of the clamp screw 559 in a counter-clockwise direction causes the inner shaft 555 to move in a distal direction within the slots 552 and 554 of the first and second jaws 50 and 80, respectively. This distal movement of the inner shaft 555 allows the first and second jaws 50, 80 to move, e.g., close, relative to each other, thereby clamping the section of tissue between the first and second jaws 50, 80.

Once a section of tissue has been clamped between the first and second jaws 50, 80, the section of tissue may be cut and/or stapled. It should be recognized that, while the present invention is illustrated as using both cutting and stapling elements, the surgical device 11 may employ only one such element, or else may employ a different type of surgical instrument.

Before the surgical device 11 is inserted into a patient's body, a staple cartridge 578 is provided within the second jaw 80. In an embodiment, the surgical device 11 is a single-use device, in which the staple cartridge is integral to the second jaw 80. Alternatively, the surgical device 11 may have a replaceable staple cartridge, e.g., replaceable staple cartridge 600 as illustrated in FIG. 4(*e*), thereby permitting the surgical device 11 to be used numerous times with different staple cartridges. In this embodiment, if the surgical device 11 is being used for the first time, the staple cartridge 600 may be pre-installed during manufacture and assembly of the surgical device 11, or else may be installed by the user just prior to using the surgical device 11. If the surgical device 11 is being used for the second or more time, the staple cartridge 600 may be installed by the user just prior to using the surgical device 11. When the staple cartridge 600 is inserted into the second jaw 80, the distal end of the firing shaft 557 is received within the proximally-facing opening 605*d* of the wedge driver 605.

To illustrate the cutting/stapling operation of the surgical device 11, reference is first made to FIG. 5(*d*). With the staple cartridge 600 installed within the second jaw 80 of the surgical device 11, the surgical device 11 may be operated such that the function selector module 1110 is moved to a fourth functional position. As set forth above, in this fourth functional position, the function selector module 1110 causes engagement of the second rotatable drive shaft 1110*b* with the firing driver 98. FIG. 5(*d*) is a side perspective view, partially in section, of the handle 1103 of the surgical device 11. In particular, FIG. 5(*d*) illustrates some of the components of the handle 1103 that form the firing driver 98 and that function to move a cutting and/or stapling element, e.g., to drive a staple pushing element and/or cutting blade through a section of tissue, according to the embodiment illustrated in FIGS. 3(*a*) through 3(*e*). FIG. 5(*d*) illustrates some of these firing driver 98 components in bold.

Referring to FIG. 5(*d*), the first rotatable drive shaft 1110*a* is again caused to rotate, e.g., in a clockwise direction such as by motor 96 (shown in FIG. 2(*b*)). Since the longitudinally-arranged bore of the first rotatable drive shaft 1110*a* and the proximal end of a selector shaft 601 are correspondingly sized and shaped, rotation of the first rotatable drive shaft 1110*a* in a clockwise direction causes rotation of the selector shaft 601 in a clockwise direction. By virtue of the threaded engagement of the threaded portion 607 of the selector shaft 601 within the threaded bore of the function selector block 609, rotation of the selector shaft 601 in a clockwise direction causes the function selector block 609 to move proximally to, e.g., a fourth position, in which specific gears of the handle 1103 are engaged with each other.

Once the function selector block 609 is moved to the fourth position, the second rotatable drive shaft 1110*b* is caused to rotate, e.g., in a counter-clockwise direction, such as by motor 100 (shown in FIG. 2(*b*)). Since the longitudinally-arranged bore of the second rotatable drive shaft 1110*b* and the proximal end of the function shaft 611 are correspondingly sized and shaped, rotation of the second rotatable drive shaft 1110*b* in a counter-clockwise direction causes rotation of the function shaft 611 in a counter-clockwise direction. The input spur gear 619 and the firing spur gear 617 of the second rotatable drive shaft 1110*b* are also caused to rotate in a counter-clockwise direction. Due to the engagement of the outer circumferential gear teeth 6171 of the fire spur gear 617 with the outer circumferential gear teeth 6251 of the fire spur gear 625, rotation of the fire spur gear 617 in a counter-clockwise direction causes rotation of the fire spur gear 625 in a clockwise direction. Likewise, due to the engagement of the outer circumferential gear teeth 6191 of the input spur gear 619 with the outer circumferential gear teeth 6231 of the rotation spur gear 623, rotation of the input spur gear 619 in a counter-clockwise direction causes rotation of the rotation spur gear 623 in a clockwise direction. Still further, due to the engagement of the outer circumferential gear teeth 6171 of the fire spur gear 617 with the outer circumferential gear teeth 6081 of the firing spur gear 608, rotation of the fire spur gear 617 in a counter-clockwise direction causes rotation of the firing spur gear 608 in a clockwise direction.

Firing spur gear 608 is mounted at an end of the firing gear shaft 604, that has the first firing miter gear 610 mounted at its opposite end, such that rotation of the firing spur gear 608 in a clockwise direction also causes rotation of the firing gear shaft 604 and the first firing miter gear 610 in a clockwise direction.

The miter gear teeth 6101 of the first firing miter gear 610 engage the miter gear teeth 6121 of the second firing miter gear 612, such that rotation of the first firing miter gear 610 in a clockwise direction causes rotation of the second firing miter gear 612 in a clockwise direction (when viewed into the page) about an axis that is perpendicular to the longitudinal axis of the firing gear shaft 604. Likewise, the miter gear teeth 6121 of the second firing miter gear 612 engage the miter gear teeth 6141 of the third firing miter gear 614, such that rotation of the second firing miter gear 612 in a clockwise direction causes rotation of the third firing miter gear 614 in a counter-clockwise direction. The third firing miter gear 614 is mounted at the proximal end of the second firing gear shaft 618 such that rotation of the third firing miter gear 614 in a counter-clockwise direction causes rotation of the second firing gear shaft 618 in a counter-clockwise direction.

FIG. 6(*d*) is a side perspective view, partially in section, of another section of the distal portion of the surgical device 11. In particular, FIG. 6(*d*) illustrates additional components of the surgical device 11 that function to move a cutting and/or stapling element, e.g., to drive a staple pushing element and/or cutting blade through a section of tissue, according to the embodiment illustrated in FIGS. 3(*f*) and 4(*d*). FIG. 6(*d*) illustrates some of these firing driver 98 components in bold.

As set forth above, the second firing gear shaft 618 extends distally through the rotating tube 677 to eventually form the firing shaft 529. The rotation of the fire shaft 527 in a counter-clockwise direction causes rotation of the input bevel gear 505*b* in a counter-clockwise direction. By virtue of the meshing engagement of the gear teeth of the input bevel gear 505*b* with the gear teeth of the lower idler bevel gear 549*b*, rotation of the input bevel gear 505*b* in a counter-clockwise direction about the longitudinal axis of the firing shaft 529 causes rotation of the lower idler bevel gear 549*a* in a clockwise direction (when viewed from above) about the longitudinal axis of the hinge pin 551. Likewise, by virtue of the meshing engagement of the gear teeth of the lower idler bevel gear 549*b* with the gear teeth of the fire input bevel gear 533, rotation of the lower idler bevel gear 549*b* in a clockwise direction about the longitudinal axis of the hinge pin 551 causes rotation of the fire input bevel gear 533 in a clockwise direction. Since the distal end of the fire input bevel gear 533 is non-rotatably engaged relative to the proximal end of the firing shaft 557, rotation of the fire input bevel gear 533 in a clockwise direction causes rotation of the firing shaft 557 in a clockwise direction.

Figure 5E:
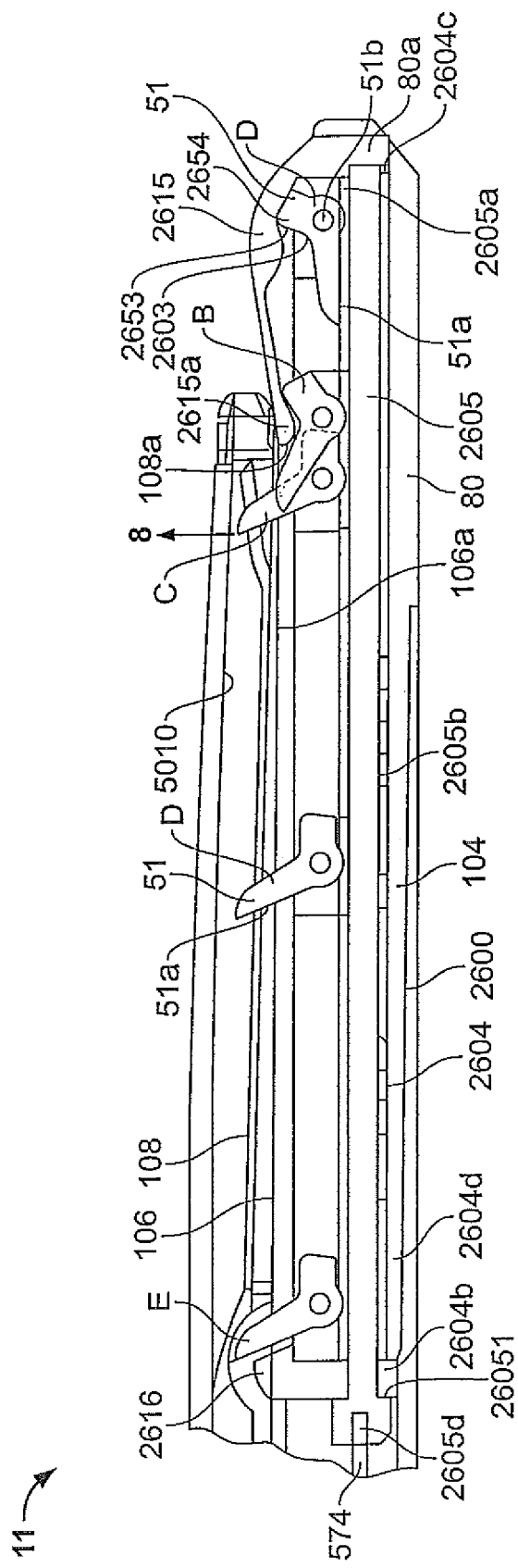
FIG. 5(e) is a cross-sectional view of a cutting and/or stapling element of the surgical device 11, according to an embodiment of the present invention.

To further illustrate the cutting/stapling operation of the surgical device 11, reference is next made to FIG. 5(e). FIG. 5(e) is a cross-sectional view of the jaw portion of the surgical device 11, according to an embodiment of the present invention, in a fully closed position. In FIG. 5(e), the surgical device 11 is illustrated absent a section of tissue between the clamping surfaces 106, 108 of the first and the second jaws 50, 80.

As illustrated in FIG. 5(e), the surgical device 11 is disposed within the second jaw 80, and the cutting and stapling element 104 includes the replaceable staple cartridge 2600 of FIG. 5(e) that is replaceably mountable within the second jaw 80. The replaceable staple cartridge 2600, which was shown in an exploded view in FIG. 4(e), is shown assembled and mounted within the second jaw 80 in FIG. 5(e).

As illustrated in FIG. 5(e), the wedge 2603 has disposed thereon a blade 51 having a cutting edge 51a. Alternatively, the cutting and stapling elements may be separately disposed. In the example embodiment illustrated in FIG. 5(e), the blade 51 has a tail region 2654 with a contact face 2653. The blade 51 is rotatably coupled to the wedge 2603 around pivot 51b to allow the blade 51 to rotate between a first and a second position. FIG. 5(e) illustrates the wedge 2603 and the blade 51 in several positions, labeled as positions A to E, as the wedge 2603 and the blade 51 travel from the distal end 2604c to the proximal end 2604d of the staple tray 2604.

In the position labeled A, the wedge 2603 and the blade 51 are positioned at the distal end 2604c of the staple tray 2604. In the position labeled A, the wedge 2603 and the blade 51 are housed within a housing 2615 and the blade 51 is rotated relative to the wedge 2603 so as to be in a retracted position, e.g., the cutting edge 51a facing upwards and is not exposed. The contact face 2653 initially faces the proximal end 2604d of the staple tray 2604.

In operation, rotation of the wedge driver 2605 in a clockwise direction (caused by its engagement with the distal end of the firing shaft 557, which is described above as also rotating in a clockwise direction) causes the wedge 2603 and the blade 51 to advance to the position labeled B. In the position labeled B, the wedge 2603 and the blade 51 are positioned proximally relative to the distal end 2604c of the staple tray 2604. Specifically, in the position labeled B, the wedge 2603 and the blade 51 are positioned such that the contact face 2653 of the blade 51 begins to contact an actuating lip 2615a of the housing 2615. As the contact face 2653 of the blade 51 begins to contact the actuating lip 2615a of the housing 2615, the blade 51 begins to rotate relative to the wedge 2603.

Further rotation of the wedge driver 2605 via the distal end of the firing shaft 557 causes the wedge 2603 and the blade 51 to advance to the position labeled C. In the position labeled C, the wedge 2603 and the blade 51 are positioned still further proximally relative to the distal end 2604c of the staple tray 2604. Specifically, in the position labeled C, the wedge 2603 and the blade 51 are positioned such that the contact face 2653 of the blade 51 has fully contacted the actuating lip 2615a of the housing 2615. When the contact face 2653 of the blade 51 has fully contacted the actuating lip 2615a of the housing 2615, the blade 51 is fully rotated relative to the wedge 2603 such that the cutting edge 51a of the blade 51 is in an extended position, e.g., the cutting edge 51a faces the proximal end 2604d of the staple tray 2604.

Further rotation of the wedge driver 2605 via the distal end of the firing shaft 557 causes the wedge 2603 and the blade 51 to advance to the position labeled D. In the position labeled D, the wedge 2603 and the blade 51 are positioned approximately at the midpoint between the distal end 2604c and the proximal end 2604d of the staple tray 2604. In the position labeled D, the blade 51 is maintained in the extended position having the cutting edge 51a facing the proximal end 2604d of the staple tray 2604 so as to cut a section of tissue (not shown) that is clamped between the first jaw 50 and the second jaw 80.

Further rotation of the wedge driver 2605 via the distal end of the firing shaft 557 causes the wedge 2603 and the blade 51 to advance to the position labeled E. In the position labeled E, the wedge 2603 and the blade 51 are positioned at the proximal end 2604d of the staple tray 2604. In the position labeled E, the blade 51 is still maintained in the extended position with the cutting edge 51a facing the proximal end 2604d of the staple tray 2604. Here, however, the blade 51 is enclosed within a housing 2616 so that the cutting edge 51a is not exposed.

The staples 2606 housed within the staple tray 2604 may simultaneously be fired with the movement of the blade 51 from the proximal end 80b to the distal end 80a of the second jaw 80. For instance, rotation of the wedge driver 2605 via the distal end of the firing shaft 557 causes the wedge 2603 to be moved through the central channel 2604e of the staple tray 2604. As the wedge 2603 is moved from the distal end 2604c to the proximal end 2604d of the staple tray 2604 through the central channel 2604e, the pair of sloped edges 2603b of the wedge 2603 slideably engage the respective top surfaces 2607a of the staple pushers 2607 and successively push the staple pushing fingers 2607c of the staple pushers 2607 into, and thus the staples 2606 out of, the slots 2604h in the staple tray 2604. When the surgical device 11 is in the closed position, the rows 2702 of the staple guides 2703 align with the slots 2604h of the staple tray 2604 in the second jaw 80 so that the staples 2606 maintained in the slots 2604h of the staple tray 2604 are pushed by the staple pushing fingers 2607c of the staple pushers 2607 into, and closed by, corresponding staple guides 2703 of the anvil member 2700. The staple guides 2703 receive the prongs 2606b of the staples 2606 when the surgical device 11 is fired and bend the prongs 2606b so as to close the staples 2606, thereby stapling the section of tissue.

It should be recognized that, according to various embodiments of the present invention, the blade 51 and the wedge 2603 may be moved in either a proximal or a distal direction in order to cut and/or staple a section of tissue disposed between the first jaw 50 and the second jaw 80. Furthermore, it should be recognized that, according to various embodiments of the present invention, any mechanical arrangement that is configured to move the blade 51 and the wedge 2603 in order to cut and/or staple a section of tissue disposed between the first jaw 50 and the second jaw 80 may be employed.

Once the section of tissue may be cut and/or stapled, the surgical device 11 may be employed to return the wedge 2603 and the blade 51 to their initial positions. This may be particularly desirable when the surgical device 11 employs replaceable staple cartridges, e.g., replaceable staple cartridge 600 as illustrated in FIG. 4(e), thereby permitting the surgical device 11 to be used numerous times with different staple cartridges. Once the wedge 2603 and the blade 51 have been moved to their initial positions, the surgical device 11 may be used for a second or more time. To do so, the user may remove the spent staple cartridge 600 and insert in the surgical device 11 a new staple cartridge 600, the distal end of the firing shaft 557 being received within the proximally-facing opening 2605*d* of the wedge driver 2605 of the new staple cartridge 2600. Of course, it should be recognized that this step of returning the wedge 2603 and the blade 51 to their initial positions may be performed either prior to, or subsequent to, removal of the surgical device 11 from the patient's body.

In order to return the wedge 2603 and the blade 51 to their initial positions, and as shown in FIG. 5(*d*), the function selector block 609 may remain in the fourth position, in which specific gears of the handle 1103 are engaged with each other. While the function selector block 609 is in the fourth position, the second rotatable drive shaft 1110*b* may be caused to rotate, e.g., in a clockwise direction, such as by motor 100 (shown in FIG. 2(*b*)). Rotation of the second rotatable drive shaft 1110*b* in a clockwise direction causes rotation of the function shaft 611 in a clockwise direction. The input spur gear 619 and the firing spur gear 617 of the second rotatable drive shaft 1110*b* are also caused to rotate in a clockwise direction. Due to the engagement of the outer circumferential gear teeth 6171 of the fire spur gear 617 with the outer circumferential gear teeth 6251 of the fire spur gear 625, rotation of the fire spur gear 617 in a clockwise direction causes rotation of the fire spur gear 625 in a counter-clockwise direction. Likewise, due to the engagement of the outer circumferential gear teeth 6191 of the input spur gear 619 with the outer circumferential gear teeth 6231 of the rotation spur gear 623, rotation of the input spur gear 619 in a clockwise direction causes rotation of the rotation spur gear 623 in a counter-clockwise direction. Still further, due to the engagement of the outer circumferential gear teeth 6171 of the fire spur gear 617 with the outer circumferential gear teeth 6081 of the firing spur gear 608, rotation of the fire spur gear 617 in a clockwise direction causes rotation of the firing spur gear 608 in a counter-clockwise direction.

Firing spur gear 608 is mounted at an end of the firing gear shaft 604, that has the first firing miter gear 610 mounted at its opposite end, such that rotation of the firing spur gear 608 in a counter-clockwise direction also causes rotation of each one of the firing gear shaft 604 and the first firing miter gear 610 in a counter-clockwise direction.

The miter gear teeth 6101 of the first firing miter gear 610 engage the miter gear teeth 6121 of the second firing miter gear 612, such that rotation of the first firing miter gear 610 in a counter-clockwise direction causes rotation of the second firing miter gear 612 in a counter-clockwise direction (when viewed into the page) about an axis that is perpendicular to the longitudinal axis of the firing gear shaft 604. Likewise, the miter gear teeth 6121 of the second firing miter gear 612 engage the miter gear teeth 6141 of the third firing miter gear 614, such that rotation of the second firing miter gear 612 in a counter-clockwise direction causes rotation of the third firing miter gear 614 in a clockwise direction. The third firing miter gear 614 is mounted at the proximal end of the second firing gear shaft 618 such that rotation of the third firing miter gear 614 in a clockwise direction causes rotation of the second firing gear shaft 618 in a clockwise direction.

Referring to FIG. 6(*d*), the second firing gear shaft 618 extends distally through the rotating tube 677 to eventually form the firing shaft 529. The rotation of the fire shaft 527 in a clockwise direction causes rotation of the input bevel gear 505*b* in a clockwise direction. By virtue of the meshing engagement of the gear teeth of the input bevel gear 505*b* with the gear teeth of the lower idler bevel gear 549*b*, rotation of the input bevel gear 505*b* in a clockwise direction about the longitudinal axis of the firing shaft 529 causes rotation of the lower idler bevel gear 549*a* in a counter-clockwise direction (when viewed from above) about the longitudinal axis of the hinge pin 551. Likewise, by virtue of the meshing engagement of the gear teeth of the lower idler bevel gear 549*b* with the gear teeth of the fire input bevel gear 533, rotation of the lower idler bevel gear 549*b* in a counter-clockwise direction about the longitudinal axis of the hinge pin 551 causes rotation of the fire input bevel gear 533 in a counter-clockwise direction. Since the distal end of the fire input bevel gear 533 is non-rotatably engaged relative to the proximal end of the firing shaft 557, rotation of the fire input bevel gear 533 in a counter-clockwise direction causes rotation of the firing shaft 557 in a counter-clockwise direction.

Referring to FIG. 5(*e*), the wedge driver 2605 is rotated in a counter-clockwise direction by the rotation of the firing shaft 557, such that wedge 2603 and the blade 51 travel from the proximal end 2604*d* to the distal end 2604*c* of the staple tray 2604 until, when the wedge 2603 and the blade 51 are positioned at the distal end 2604*c* of the staple tray 2604, e.g., the position that is labeled as position A, the wedge 2603 and the blade 51 are housed again within the housing 2615, the blade 51 being rotated relative to the wedge 2603 so as to be in a retracted position, e.g., the cutting edge 51*a* facing upwards and is not exposed.

Once the wedge 2603 and the blade 51 to their initial positions, the surgical device 11 may be employed to move the jaw portion 11*a* relative to the shaft portion 11*b*, e.g., to pivot the jaw portion 11*a* about axis B relative to the shaft portion 11*b*, back to its initial aligned positioned for the purposes of easing the removal of the surgical device from the incision of the patient. In order to perform this function, the surgical device 11 may be operated such that the function selector module 1110 is returned to the second functional position. As set forth above, in this second functional position, the function selector module 1110 causes engagement of the second rotatable drive shaft 1110*b* with an articulation driver 201.

Referring to FIG. 5(*b*), the first rotatable drive shaft 1110*a* is again caused to rotate, e.g., in a counter-clockwise direction, such as by motor 96 (shown in FIG. 2(*b*)). Since the longitudinally-arranged bore of the first rotatable drive shaft 1110*a* and the proximal end of a selector shaft 601 are correspondingly sized and shaped, rotation of the first rotatable drive shaft 1110*a* in a counter-clockwise direction causes rotation of the selector shaft 601 in a counter-clockwise direction. By virtue of the threaded engagement of the threaded portion 607 of the selector shaft 601 within the threaded bore of the function selector block 609, rotation of the selector shaft 601 causes the function selector block 609 to move distally to, e.g., the second position, in which specific gears of the handle 1103 are engaged with each other.

Once the function selector block 609 is returned to the second position, the second rotatable drive shaft 1110*b* may be caused to rotate, e.g., in a clockwise direction, such as by motor 100 (shown in FIG. 2(*b*)). Since the longitudinally-arranged bore of the second rotatable drive shaft 1110*b* and the proximal end of the function shaft 611 are correspondingly sized and shaped, rotation of the second rotatable drive shaft 1110*b* in a clockwise direction causes rotation of the function shaft 611 in a clockwise direction. The fire spur gear 617 of the second rotatable drive shaft 1110*b* is also caused to rotate in a clockwise direction. Due to the engagement of the outer circumferential gear teeth 6191 of the input spur gear 619 with the outer circumferential gear teeth 6231 of the articulation spur gear 623, rotation of the input spur gear 619 in a clockwise direction causes rotation of the articulation spur gear 623 in a counter-clockwise direction.

When the function selector block 609 is in the second position, the rotation spur gear 623 and the articulation spur gear 629 are engaged with the gear shaft 621 such that rotation of the rotation spur gear 623 in a counter-clockwise direction causes rotation of the gear shaft 621 in a counter-clockwise direction and also rotation of the articulation spur gear 629 in a counter-clockwise direction. By virtue of the meshing engagement of the outer circumferential gear teeth 6291 of the articulation spur gear 629 with the outer circumferential gear teeth 6871 of the articulation spur gear 687, rotation of the articulation spur gear 629 in a counter-clockwise direction causes rotation of the articulation spur gear 687 in a clockwise direction.

Rotation of the articulation spur gear 687, which is mounted at an end of the articulation gear shaft 685, in a clockwise direction causes rotation of the articulation gear shaft 685 in a clockwise direction and of the articulation worm gear 689, which is also mounted thereon, in a clockwise direction. By virtue of the engagement of outer circumferential worm gear teeth 6891 of the articulation worm gear 689 with the outer circumferential gear teeth 6911 of the articulation gear 691, rotation of the articulation worm gear 689 in a clockwise direction causes rotation of the articulation gear 691 in a clockwise direction (when viewed into the page) about a pivot axis that is perpendicular to a longitudinal axis of the articulation gear shaft 685. Likewise, rotation of the articulation gear 691 in a clockwise direction causes rotation of the articulation miter gear 692, that is mounted thereon, in a clockwise direction. The miter gear teeth 6921 of the articulation miter gear 692 engage the miter gear teeth 6961 of the articulation miter gear 696, such that rotation of the articulation miter gear 692 in a clockwise direction causes rotation of the articulation miter gear 696 in a clockwise direction.

The articulation miter gear 696 is mounted on the second articulation gear shaft 693. By virtue of the threaded engagement between the threaded rod portion 695 of the second articulation gear shaft 693 and the interior threaded bore of the articulation miter gear 696, rotation of the articulation miter gear 696 in a clockwise direction causes the second articulation gear shaft 693 to move, e.g., proximally (depending on the direction of threads on the second articulation gear shaft 693).

Referring to FIG. 6(*b*) proximal movement of second articulation gear shaft 693 and the articulation shaft 525 which it eventually forms, causes the rack 517 to also move proximally. By virtue of the engagement of the teeth of the rack 517 with the teeth of the rack gear 519, proximal movement of the rack 517 causes the rack gear 519, and the proximal articulation gear 515, to rotate in a counter-clockwise direction (when viewed from above). Also, by virtue of the engagement of the outer circumferential teeth of the proximal articulation gear 515 with the outer circumferential teeth of the distal articulation gear 547, rotation of the proximal articulation gear 515 in a counter-clockwise direction causes rotation of the distal articulation gear 547 in a clockwise direction. Since the distal articulation gear 547 is rotationally fixed relative to the distal pivot housing 543, rotation of the distal articulation gear 547 in a clockwise direction causes the jaw portion 11*a* to move, e.g., articulate, in a clockwise direction (when viewed from above) relative to the shaft portion 11*b* about the hinge pin 551. This movement, e.g., articulation, of the jaw portion 11*a* relative to the shaft portion 11*b* may continue until the longitudinal axes of the jaw portion 11*a* and the shaft portion 11*b* are aligned, thereby easing the removal of the surgical device 11 from the patient's incision.

Once the longitudinal axes of the jaw portion 11*a* and the shaft portion 11*b* have been aligned, the surgical device 11 may be employed to return the shaft portion 11*b* to its initial position relative to the handle 1103, e.g., by rotating the shaft portion 11*b* relative to the handle 1103 about the longitudinal axis D of the handle 1103 until the shaft portion 11*b* and the handle 1103 are in their initial, e.g., aligned, positions relative to each other. Again, this may be particularly desirable when the surgical device 11 employs replaceable staple cartridges, e.g., replaceable staple cartridge 600 as illustrated in FIG. 4(*e*), so as to return the surgical device 11 into a condition which permits it to be used numerous times with different staple cartridges. Once the shaft portion 11*b* has been rotated back to its initial position relative to the handle 1103, the surgical device 11 may be used for a second or more time. Of course, it should be recognized that this particular step may be performed either prior to, or subsequent to, removal of the surgical device 11 from the patient's body.

In order to rotate the shaft portion 11*b* relative to the handle 1103 about the longitudinal axis D of the handle 1103 until the shaft portion 11*b* and the handle 1103 are in their initial positions relative to each other, and as shown in FIG. 5(*d*), the surgical device 11 may be operated such that the function selector module 1110 is returned to the first functional position. As set forth above, in this first functional position, the function selector module 1110 causes engagement of the second rotatable drive shaft 1110*b* with the rotation driver 202.

Referring now to FIG. 5(*a*), the first rotatable drive shaft 1110*a* is caused to rotate, e.g., such as by motor 96 (shown in FIG. 2(*b*)) in, e.g., a clockwise direction. Since the longitudinally-arranged bore of the first rotatable drive shaft 1110*a* and the proximal end of a selector shaft 601 are correspondingly sized and shaped, rotation of the first rotatable drive shaft 1110*a* in a clockwise direction causes rotation of the selector shaft 601 in a clockwise direction. By virtue of the threaded engagement of the threaded portion 607 of the selector shaft 601 within the threaded bore of the function selector block 609, rotation of the selector shaft 601 in a clockwise direction causes the function selector block 609 to be returned to the distal-most, e.g., first position, in which specific gears of the handle 1103 are engaged with each other.

Once the function selector block 609 is returned to the first position, the second rotatable drive shaft 1110*b* may be caused to rotate, e.g., in a clockwise direction, such as by motor 100 (shown in FIG. 2(*b*)). Since the longitudinally-arranged bore of the second rotatable drive shaft 1110*b* and the proximal end of the function shaft 611 are correspondingly sized and shaped, rotation of the second rotatable drive shaft 1110*b* in a clockwise direction causes rotation of the function shaft 611 in a clockwise direction. The input spur gear 619 of the second rotatable drive shaft 1110*b* also rotates in a clockwise direction. Due to the engagement of the outer circumferential gear teeth 6191 of the input spur gear 619 with the outer circumferential gear teeth 6231 of the rotation spur gear 623, rotation of the input spur gear 619 in a clockwise direction causes rotation of the rotation spur gear 623 in a counter-clockwise direction.

When the function selector block 609 is in the first position, the rotation spur gear 623 and the rotation spur gear 631 are engaged with the gear shaft 621 such that rotation of the rotation spur gear 623 in a counter-clockwise direction causes rotation of the gear shaft 621 in a counter-clockwise direction and also rotation of the rotation spur gear 631 in a counter-clockwise direction. By virtue of the meshing engagement of the outer circumferential gear teeth 6311 of the rotation spur gear 631 with the outer circumferential gear teeth 6391 of the rotation spur gear 639, rotation of the rotation spur gear 631 in a counter-clockwise direction causes rotation of the rotation spur gear 639 in a clockwise direction.

Rotation of the rotation spur gear 639, which is mounted at an end of the rotation gear shaft 633, in a clockwise direction causes rotation of the rotation gear shaft 633 in a clockwise direction and rotation of the rotation worm gear 641, which is also mounted thereon, in a clockwise direction. By virtue of the engagement of outer circumferential worm gear teeth 6411 of the rotation worm gear 641 with the outer circumferential gear teeth 6431 of the rotation gear 643, rotation of the rotation worm gear 641 in a clockwise direction causes rotation of the rotation gear 643 in a counter-clockwise direction (as viewed when looking into the page) about a pivot axis that is perpendicular to a longitudinal axis of the rotation gear shaft 633. Likewise, rotation of the rotation gear 643 in a counter-clockwise direction causes rotation of the rotation miter gear 644, that is mounted thereon, in a counter-clockwise direction. The miter gear teeth 6441 of the rotation miter gear 644 engage the miter gear teeth 6691 of the rotation miter gear 669, such that rotation of the rotation miter gear 644 in a counter-clockwise direction causes rotation of the rotation miter gear 669 in a clockwise direction.

The rotation miter gear 669 is mounted on the second rotation gear shaft 665, such that rotation of the rotation miter gear 669 in a clockwise direction causes rotation of the second rotation gear shaft 665 in a clockwise direction and of the rotation spur gear 673 in a clockwise direction. By virtue of the meshing engagement of the outer circumferential gear teeth 6731 of the rotation spur gear 673 with the outer circumferential gear teeth 6791 of the rotating tube spur gear 679, rotation of the rotation spur gear 673 in a clockwise direction causes rotation of the rotating tube spur gear 679 in a counter-clockwise direction and also rotation of the rotating tube 677 mounted thereto in a counter-clockwise direction. The rotation of the rotating tube 677 in a counter-clockwise direction within the mouth 675 at the distal-most end of the handle 1103 may continue until the shaft portion 11b and the handle 1103 are in their initial positions relative to each other.

Figure 1:
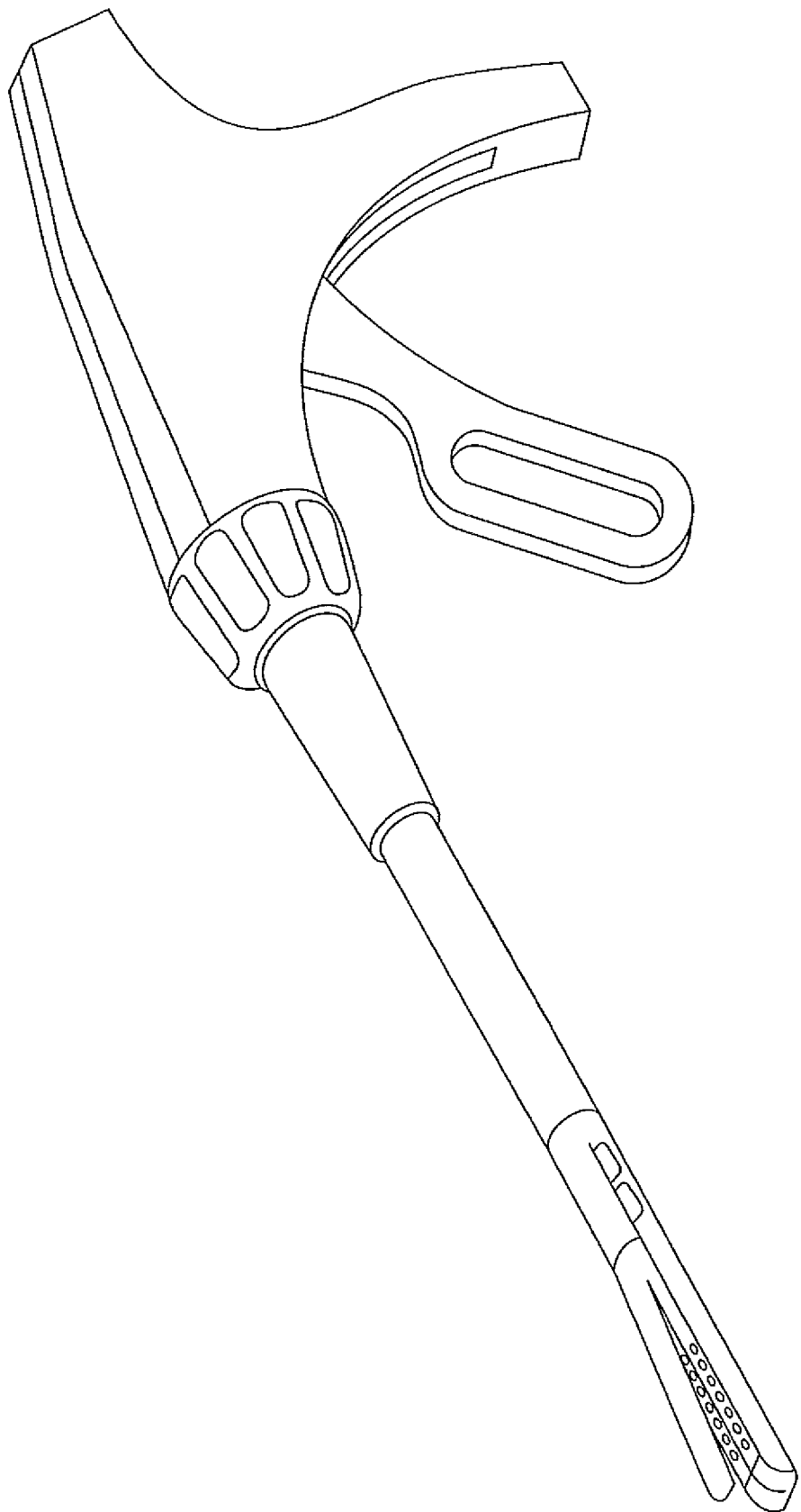
FIG. 1 is a perspective view of a conventional linear clamping, cutting and stapling device.

As set forth above, according to an example embodiment of the present invention, the surgical device 11 may be configured as an attachment to, or may be integral with, a purely mechanical device driver system, such as that illustrated in FIG. 1. Alternatively, in another example embodiment of the present invention, the surgical device 11 may be an electro-mechanical device that is configured to stand alone, e.g., that includes various motors, drive shafts, control systems, etc., in an integral arrangement such that attachment to a separate electro-mechanical surgical system is eliminated. Such an arrangement is illustrated schematically in FIG. 2(c), and may include the advantage that the surgical device 11 is not connected prior to use to a separately-disposed drive system. In this embodiment, first motor 961 and second motor 1001 are arranged within the handle 1103, such that the first and second rotatable drive shafts 1110a and 1110b are connected to, and driven by, the first and second motors 961, 1001, respectively. Still further, the surgical device 11 may be an electro-mechanical device that does not stand alone, but rather includes integrally one or more of motors, drive shafts, control systems, etc., while still being coupleable to a separate electro-mechanical surgical system that includes other ones of motors, drive shafts, control systems, etc.

In still another embodiment, the surgical device 11 may be configured as an attachment to, or may be integral with, an electro-mechanical surgical system, such as an electro-mechanical driver system 1610 illustrated in FIG. 2(a). FIGS. 3(a) through 6(d) illustrate an example embodiment of the surgical device 11 having such an arrangement, e.g., an arrangement in which the surgical device 11 is coupleable via a flexible shaft (having various rotatable drive shafts included therein) to a separate drive unit (having an arrangement of motors for rotating the rotatable drive shafts) included therein. For example, FIG. 2(b) illustrates that the surgical device 11 may include a connection element 1104 that includes a quick connect sleeve 713 having quick connect slots 713a that engage complementary quick connect elements 1664 of a flexible drive shaft 1620, which is described in further detail below (see, for example, FIG. 10).

FIG. 2(a) is, according to an example embodiment of the present invention, a perspective view of an electro-mechanical driver component 1610 to which the surgical device 11 shown and described in connection with FIGS. 3(a) through 6(d) may be connected. Such an electro-mechanical surgical system is described in, e.g., U.S. patent application Ser. No. 09/723,715, filed on Nov. 28, 2000, now Issued as U.S. Pat. No. 6,793,652 on Sep. 21, 2004, U.S. patent application Ser. No. 09/836,781, filed on Apr. 17, 2001, now Issued as U.S. Pat. No. 6,981,941 on Jan. 3, 2006, U.S. patent application Ser. No. 09/887,789, filed on Jun. 22, 2001, now Issued as U.S. Pat. No. 7,032,798 on Apr. 25, 2006, and U.S. patent application Ser. No. 10/099,634, filed on Mar. 15, 2002, now Issued as U.S. Pat. No. 7,951,071 on May 31, 2011, each of which is expressly incorporated herein in their entirety by reference thereto. The electro-mechanical driver component 1610 may include, for example, a remote power console 1612, which includes a housing 1614 having a front panel 1615. Mounted on the front panel 1615 are a display device 1616 and indicators 1618a, 1618b. A flexible shaft 1620 may extend from the housing 1614 and may be detachably attached thereto via a first coupling 1622. The distal end 1624 of flexible shaft 1620 may include a second coupling 1626 adapted to detachably couple, e.g., the surgical device 11 described above, to the distal end 1624 of the flexible shaft 1620. The second coupling 1626 may also be adapted to detachably attach a different surgical instrument or attachment. In another example embodiment, the distal end 1624 of the flexible shaft 1620 may permanently attached to or be integral with a surgical instrument.

Figure 7:
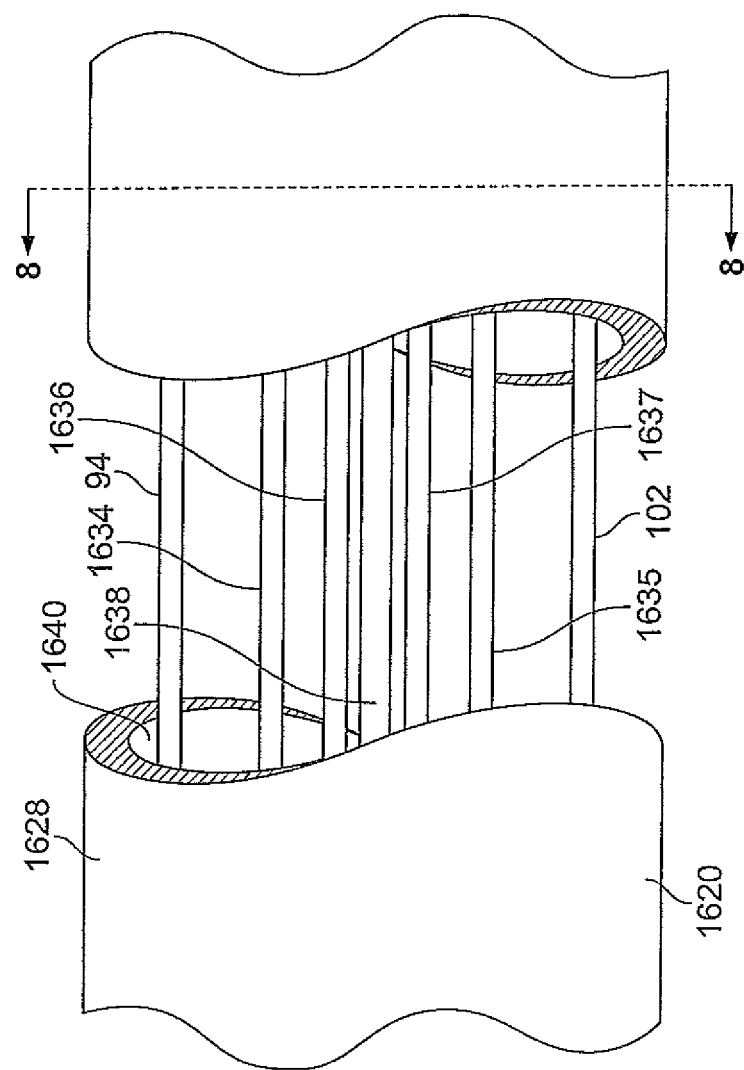
FIG. 7 illustrates a side view, partially in section, of the flexible shaft, according to another example embodiment of the present invention.
Figure 8:
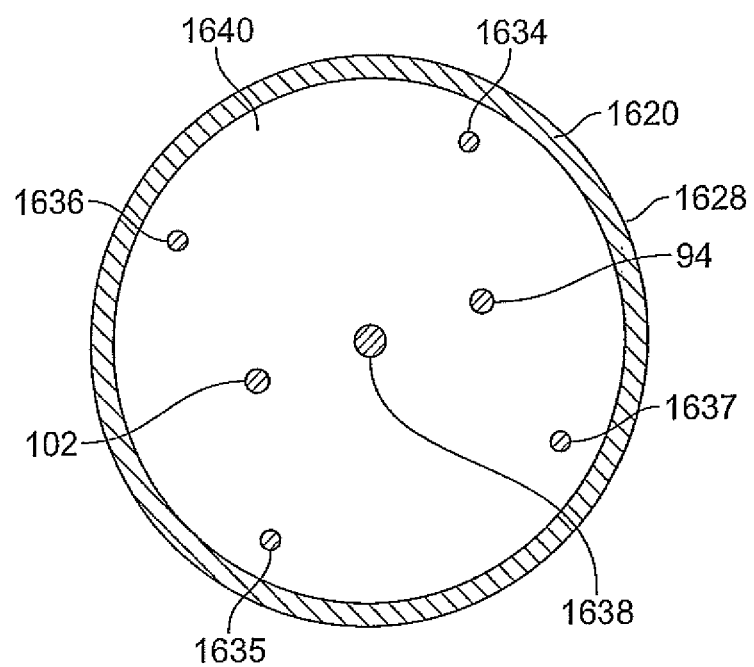
FIG. 8 is a cross-sectional view of the flexible shaft taken along the line 8-8 illustrated in FIG. 7.

Any suitable arrangement of couplings and shafts, e.g., flexible or otherwise, may be employed in order to connect the surgical device 11 to the electro-mechanical drive component 1610 may be employed. For instance, FIGS. 7 through 10 illustrate an arrangement by which the surgical device 11 may be attached to the electro-mechanical power console 1610. Referring to FIG. 7, there is seen a side view, partially in section, of the flexible shaft 1620. According to an example embodiment, the flexible shaft 1620 includes a tubular sheath 1628, which may include a coating or other sealing arrangement configured to provide a fluid-tight seal between the interior channel 1640 thereof and the environment. The sheath 1628 may be formed of a tissue-compatible, sterilizable elastomeric material. The sheath 1628 may also be formed of a material that is autoclavable. Disposed within the interior channel 1640 of the flexible shaft 1620, and extending along the entire length thereof, may be a first rotatable drive shaft 94, a second rotatable drive shaft 102, a first steering cable 1634, a second steering cable 1635, a third steering cable 1636, a fourth steering cable 1637 (it should be noted that such steering cables 1634, 1635, 1636 and 1637 may, in various embodiments of the present invention, be eliminated as the surgical device 11 may be considered to provide sufficient maneuverability without the steering capabilities of these particular steering cables) and a data transfer cable 1638. FIG. 8 is a cross-sectional view of the flexible shaft 1620 taken along the line 8-8 illustrated in FIG. 7 and further illustrates the several cables 94, 102, 1634, 1635, 1636, 1637 and 1638. Each distal end of the steering cables 1634, 1635, 1636, 1637 is affixed to the distal end 1624 of the flexible shaft 1620. Each of the several cables 94, 102, 1634, 1635, 1636, 1637, 1638 may be contained within a respective sheath.

The first rotatable drive shaft 94 and the second rotatable drive shaft 102 may be configured, for example, as highly flexible drive shafts, such as, for example, braided or helical drive cables. It should be understood that such highly flexible drive cables may have limited torque transmission characteristics and capabilities. It should also be understood that the surgical device 11, or other attachments connected to the flexible shaft 1620, may require a higher torque input than the torque transmittable by the drive shafts 94, 102. The drive shafts 94, 102 may thus be configured to transmit low torque but high speed, the high-speed/low-torque being converted to low-speed/high-torque by gearing arrangements disposed, for example, at the distal end and/or the proximal end of the drive flexible shaft 1620, in the surgical instrument or attachment and/or in the remote power console 1612. It should be appreciated that such gearing arrangement(s) may be provided at any suitable location along the power train between the motors disposed in the housing 1614 and the attached surgical instrument or other attachment connected to the flexible shaft 1620. Such gearing arrangement(s) may include, for example, a spur gear arrangement, a planetary gear arrangement, a harmonic gear arrangement, cycloidal drive arrangement, an epicyclic gear arrangement, etc. The surgical device 11 illustrated in FIGS. 3(a) through 6(d) hereinabove provide various gearing arrangements that provide the above-described conversions re: speed and/or torque transmission.

Figure 9:
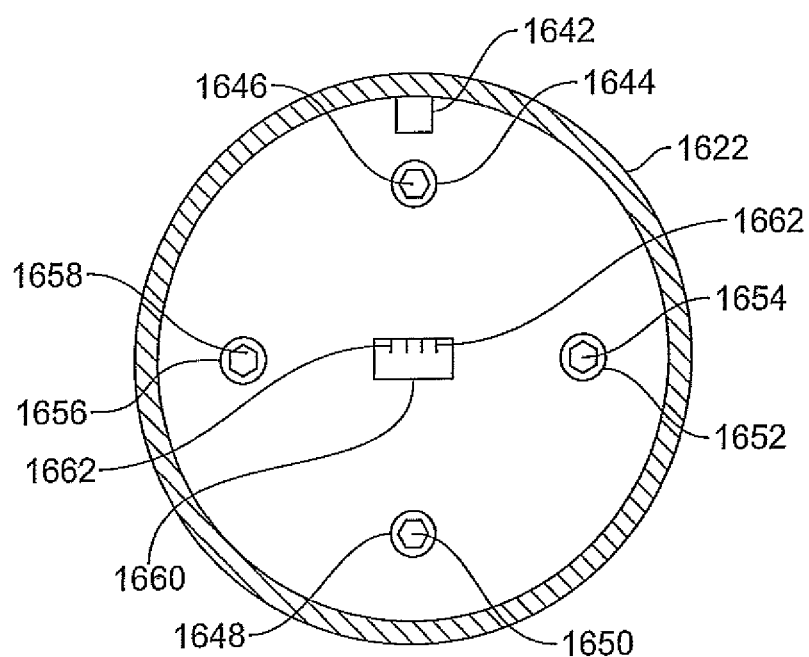
FIG. 9 illustrates a rear end view of first coupling, according to an example embodiment of the present invention.

Referring now to FIG. 9, there is seen a rear end view of first coupling 1622. The first coupling 1622 includes a first connector 1644, a second connector 1648, a third connector 1652 and a fourth connector 1656, each rotatably secured to the first coupling 1622. Each of the connectors 1644, 1648, 1652, 1656 includes a respective recess 1646, 1650, 1654, 1658. As illustrated in FIG. 9, each recess 1646, 1650, 1654, 1658 may be hexagonally shaped. It should be appreciated, however, that the recesses 1646, 1650, 1654, 1658 may have any shape and configuration adapted to non-rotatably couple and rigidly attach the connectors 1644, 1648, 1652, 1656 to respective drive shafts of the motor arrangement contained within the housing 1614. It should be appreciated that complementary projections may be provided on respective drive shafts of the motor arrangement to thereby drive the drive elements of the flexible shaft 1620. It should also be appreciated that the recesses may be provided on the drive shafts and complementary projections may be provided on the connectors 1644, 1648, 1652, 1656. Any other coupling arrangement configured to non-rotatably and releasably couple the connectors 1644, 1648, 1652, 1656 and the drive shafts of the motor arrangement may be provided.

One of the connectors 1644, 1648, 1652, 1656 is non-rotatably secured to the first drive shaft 94, and another one of the connectors 1644, 1648, 1652, 1656 is non-rotatably secured to the second drive shaft 102. The remaining two of the connectors 1644, 1648, 1652, 1656 engage with transmission elements configured to apply tensile forces on the steering cables 1634, 1635, 1636, 1637 to thereby steer the distal end 1624 of the flexible shaft 1620. The data transfer cable 1638 is electrically and logically connected with data connector 1660. The data connector 1660 includes, for example, electrical contacts 1662, corresponding to and equal in number to the number of individual wires contained in the data cable 1638. The first coupling 1622 includes a key structure 1642 configured to properly orient the first coupling 1622 to a mating and complementary coupling arrangement disposed on the housing 1612. The key structure 1642 may be provided on either one, or both, of the first coupling 1622 and the mating and complementary coupling arrangement disposed on the housing 1612. The first coupling 1622 may include a quick-connect type connector, which may engage the first coupling 1622 to the housing 1612 by a simple pushing motion. Seals may be provided in conjunction with any of the several connectors 1644, 1648, 1652, 1656, 1660 to provide a fluid-tight seal between the interior of first coupling 1622 and the environment.

Figure 10:
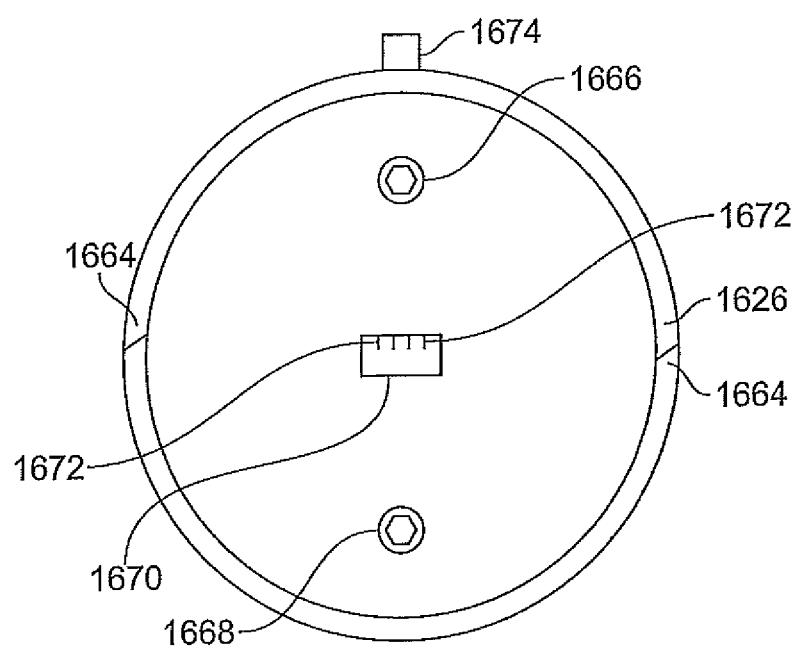
FIG. 10, there is seen a front end view of the second coupling of the flexible shaft, according to an example embodiment of the present invention.

Referring now to FIG. 10, there is seen a front end view of the second coupling 1626 of the flexible shaft 1620. In the example embodiment, the second coupling 1626 includes a first connector 1666 and a second connector 1668, each rotatably secured to the second coupling 1626 and each non-rotatably secured to a distal end of a respective one of the first and second drive shafts 94, 102. A quick-connect type fitting 1664 is provided on the second coupling 1626 to detachably secure the device 11 thereto. The quick-connect type fitting 1664 may be, for example, a rotary quick-connect type fitting, a bayonet type fitting, etc. and may be a fitting complementary to the quick connect sleeve 713 illustrated in FIG. 2(b). A key structure 1674 may be provided on the second coupling 1626 and may be configured to properly align the surgical device 11 to the second coupling 1626. The key structure or other arrangement configured to properly align the surgical device 11 to the flexible shaft 1620 may be provided on either one, or both, of the second coupling 1626 and the surgical device 11. In addition, the key structure may be provided on the device 11, as illustrated in FIG. 2(b) as the slots 713a of the quick connect sleeve 713. A data connector 1670 having electrical contacts 1672 is also provided in the second coupling 1626. Like the data connector 1660 of first coupling 1622, the data connector 1670 of the second coupling 1626 includes contacts 1672 electrically and logically connected to the respective wires of the data transfer cable 1638 and the contacts 1662 of the data connector 1660. Seals may be provided in conjunction with the connectors 1666, 1668, 1670 to provide a fluid-tight seal between the interior of the second coupling 1626 and the environment.

Disposed within the housing 1614 of the remote power console 1612 are electro-mechanical driver elements configured to drive the drive shafts 94, 102 and the steering cables 1634, 1635, 1636, 1637 to thereby operate the electro-mechanical driver component 1610 and the surgical device 11 attached to the second coupling 1626. In the example embodiment illustrated schematically in FIG. 11, five electric motors 96, 100, 1684, 1690, 1696, each operated via a power source, may be disposed in the remote power console 1612. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 11:
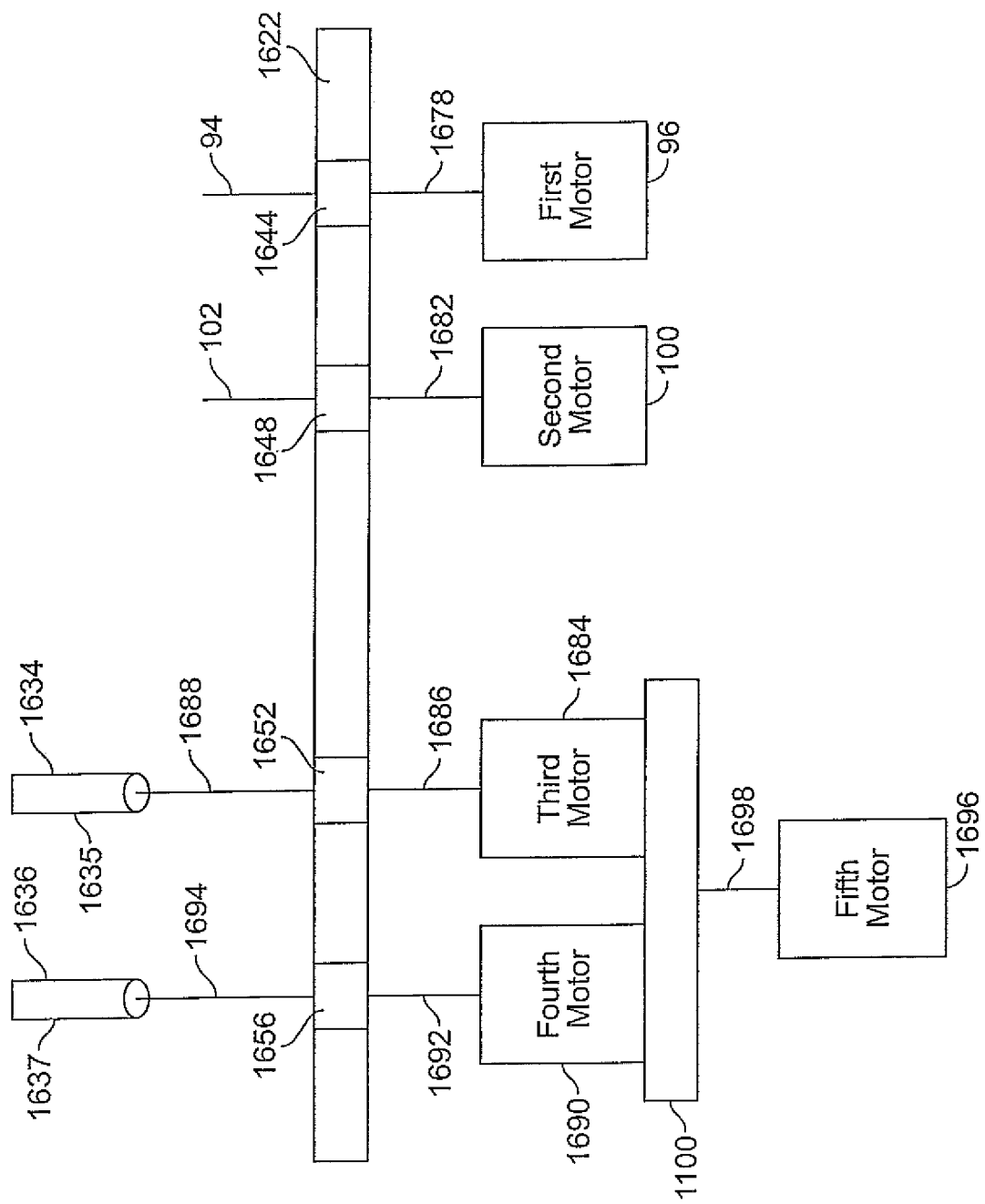
FIG. 11 illustrates schematically an arrangement of motors, according to an example embodiment of the present invention.

FIG. 11 illustrates schematically one possible arrangement of motors. An output shaft 1678 of a first motor 96 engages with the first connector 1644 of the first coupling 1622 when the first coupling 1622, and, therefore, the flexible shaft 1620, is engaged with the housing 1614 to thereby drive the first drive shaft 94 and the first connector 1666 of the second coupling 1626. Similarly, an output shaft 1682 of a second motor 100 engages the second connector 1648 of the first coupling 1622 when the first coupling 1622, and, therefore, flexible shaft 1620 is engaged with the housing 1614 to thereby drive the second drive shaft 102 and the second connector 1668 of the second coupling 1626. An output shaft 1686 of a third motor 1684 engages the third connector 1652 of the first coupling 1622 when the first coupling 1622, and, therefore, the flexible shaft 1620, is engaged with the housing 1614 to thereby drive the first and second steering cables 1634, 1635 via a first pulley arrangement 1688. An output shaft 1692 of a fourth motor 1690 engages the fourth connector 1656 of the first coupling 1622 when the first coupling 1622, and, therefore, the flexible shaft 1620, is engaged with the housing 1614 to thereby drive the third and fourth steering cables 1636, 1637 via a second pulley arrangement 1694. The third and fourth motors 1684, 1690 may be secured on a carriage 1100, which is selectively movable via an output shaft 1698 of a fifth motor 1696 between a first position and a second position to selectively engage and disengage the third and fourth motors 1684, 1690 with the respective pulley arrangement 1688, 1694 to thereby permit the flexible shaft 1620 to become taut and steerable or limp as necessary. It should be appreciated that other mechanical, electrical and/or electro-mechanical mechanisms, etc., may be used to selectively engage and disengage the steering mechanism. The motors may be arranged and configured as described, for example, in U.S. patent application Ser. No. 09/510,923, filed on Feb. 22, 2000, entitled "A Carriage Assembly for Controlling a Steering Wire Mechanism Within a Flexible Shaft," now U.S. Pat. No. 6,517,565, Issued on Feb. 11, 2003, which is expressly incorporated herein in its entirety by reference thereto. It should also be appreciated that, in accordance with other embodiments of the present invention, the steering mechanism may not be present at all, the surgical device 11 providing articulation between the jaw portion 11*a* and the shaft portion 11*b* so as to maneuver the surgical device 11 within a surgical site.

It should be appreciated that any one or more of the motors 96, 100, 1684, 1690, 1696 may be, for example, a high-speed/low-torque motor, a low-speed/high-torque motor, etc. As indicated above, the first rotatable drive shaft 94 and the second rotatable drive shaft 102 may be configured to transmit high speed and low torque. Thus, the first motor 96 and the second motor 100 may be configured as high-speed/low-torque motors. Alternatively, the first motor 96 and the second motor 100 may be configured as low-speed/high-torque motors with a torque-reducing/speed-increasing gear arrangement disposed between the first motor 96 and the second motor 100 and a respective one of the first rotatable drive shaft 94 and the second rotatable drive shaft 102. Such torque-reducing/speed-increasing gear arrangements may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 1612 or in the proximal end of the flexible shaft 1620, such as, for example, in the first coupling 1622. It should be appreciated that the gear arrangement(s) may be provided at the distal and/or proximal ends of the first rotatable drive shaft 94 and/or the second rotatable drive shaft 102 to prevent windup and breakage thereof. As set forth above, the example embodiment described hereinabove includes various such gearing arrangements for providing appropriate speed/torque function.

Figure 12:
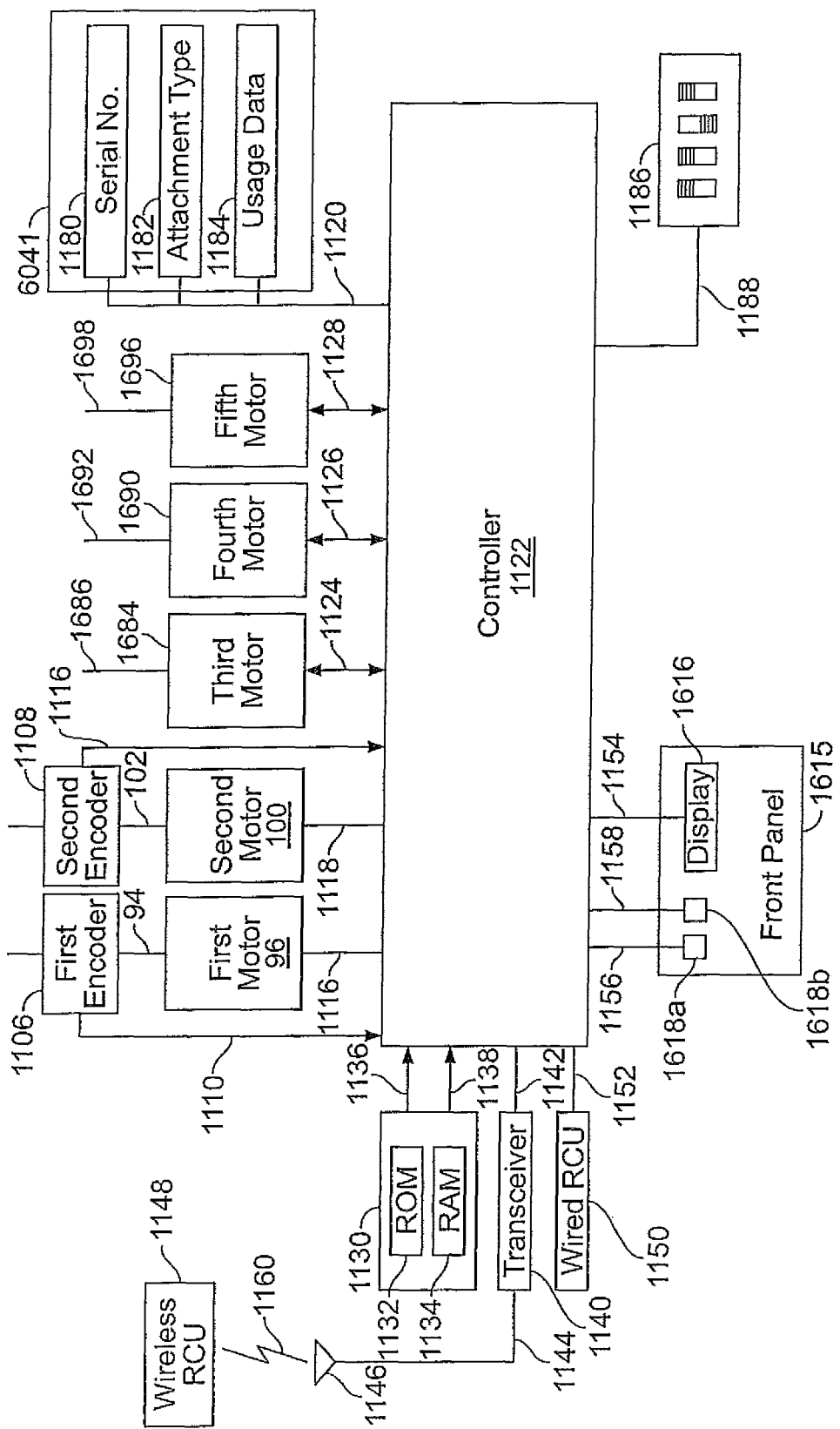
FIG. 12 illustrates a schematic view of the electromechanical driver component, according to an example embodiment of the present invention.

Referring now to FIG. 12, there is seen a schematic view of the electro-mechanical driver component 1610. A controller 1122 is provided in the housing 1614 of remote power console 1612 and is configured to control all functions and operations of the electro-mechanical driver component 1610 and the linear clamping, cutting and stapling device 11 or other surgical instrument or attachment attached to the flexible shaft 1620. A memory unit 1130 is provided and may include memory devices, such as, a ROM component 1132, a RAM component 1134, etc. The ROM component 1132 is in electrical and logical communication with the controller 1122 via a line 1136, and the RAM component 1134 is in electrical and logical communication with controller 1122 via line 1138. The RAM component 1134 may include any type of random-access memory, such as, for example, a magnetic memory device, an optical memory device, a magneto-optical memory device, an electronic memory device, etc. Similarly, the ROM component 1132 may include any type of read-only memory, such as, for example, a removable memory device, such as a PC-Card or PCMCIA-type device. It should be appreciated that the ROM component 1132 and the RAM component 1134 may be configured as a single unit or may be separate units and that the ROM component 1132 and/or the RAM component 1134 may be provided in the form of a PC-Card or PCM-CIA-type device.

The controller 1122 is further connected to the front panel 1615 of the housing 1614 and, more particularly, to the display device 1616 via a line 1154 and the indicators 1618*a*, 1618*b* via respective lines 1156, 1158. The lines 1116, 1118, 1124, 1126, 1128 electrically and logically connect controller 1122 to first, second, third, fourth and fifth motors 96, 100, 1684, 1690, 1696, respectively. A wired remote control unit ("RCU") 1150 is electrically and logically connected to the controller 1122 via a line 1152. A wireless RCU 1148 is also provided and communicates via a wireless link 1160 with a receiving/sending unit 1146 connected via a line 1144 to a transceiver 1140. The transceiver 1140 is electrically and logically connected to the controller 1122 via a line 1142. The wireless link 1160 may be, for example, an optical link, such as an infrared link, a radio link or any other form of wireless communication link.

A switch device 1186, which may include, for example, an array of DIP switches, may be connected to the controller 1122 via a line 1188. The switch device 1186 may be configured, for example, to select one of a plurality of languages used in displaying messages and prompts on the display device 1616. The messages and prompts may relate to, for example, the operation and/or the status of the electro-mechanical driver component 1610 and/or to the surgical device 11 attached thereto.

According to the example embodiment of the present invention, a first encoder 1106 is provided within the second coupling 1626 and is configured to output a signal in response to and in accordance with the rotation of the first drive shaft 94. A second encoder 1108 is also provided within the second coupling 626 and is configured to output a signal in response to and in accordance with the rotation of the second drive shaft 102. The signal output by each of the encoders 1106, 1108 may represent the rotational position of the respective drive shaft 94, 102 as well as the rotational direction thereof. These encodes may be an arrangement of light sources, e.g., LEDs, and optical fibers as illustrated for instance in FIG. 6(e). Alternatively, such encoders 1106, 1108 may include, for example, Hall-effect devices, optical devices, etc. Although the encoders 1106, 1108 are described as being disposed within the second coupling 1626, it should be appreciated that the encoders 1106, 1108 may be provided at any location between the motor system and the surgical device 11. It should be appreciated that providing the encoders 1106, 1108 within the second coupling 1626 or at the distal end of the flexible shaft 1620 may provide an accurate determination of the drive shaft rotation. If the encoders 1106, 1108 are disposed at the proximal end of the flexible shaft 1620, windup of the first and second rotatable drive shafts 94, 102 may result in measurement error.

Figure 13:
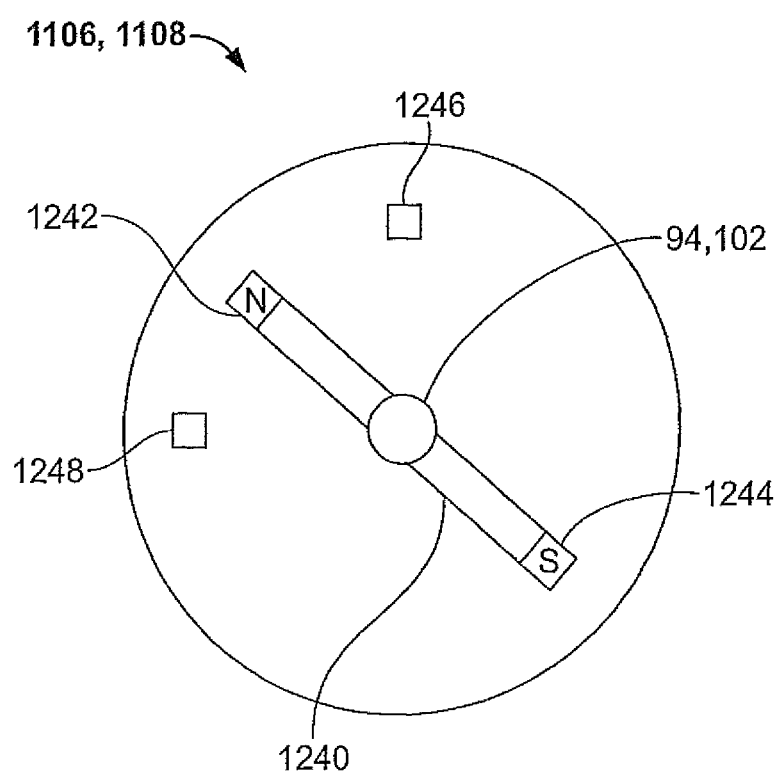
FIG. 13 is a schematic view of an encoder, according to an example embodiment of the present invention.

FIG. 13 is a schematic view of an encoder 1106, 1108, which includes a Hall-effect device. Mounted non-rotatably on the drive shaft 94, 102 is a magnet 1240 having a north pole 1242 and a south pole 1244. The encoder 1106, 1108 further includes a first sensor 1246 and second sensor 1248, which are disposed approximately 90° apart relative to the longitudinal, or rotational, axis of the drive shaft 94, 102. The output of the sensors 1246, 1248 is persistent and changes its state as a function of a change of polarity of the magnetic field in the detection range of the sensor. Thus, based on the output signal from the encoders 1106, 1108, the angular position of the drive shaft 94, 102 may be determined within one-quarter revolution and the direction of rotation of the drive shaft 94, 102 may be determined. The output of each encoder 1106, 1108 is transmitted via a respective line 1110, 1112 of data transfer cable 1638 to controller 1122. The controller 1122, by tracking the angular position and rotational direction of the drive shafts 94, 102 based on the output signal from the encoders 1106, 1108, may thereby determine the position and/or state of the components of the surgical device connected to the electro-mechanical driver component 1610. That is, by counting the revolutions of the drive shaft 94, 102, the controller 1122 may determine the position and/or state of the components of the surgical device connected to the electro-mechanical driver component 1610.

For example, the advancement distance of the first jaw 50 relative to the second jaw 80 and of the wedge 2603 may be functions of, and ascertainable on the basis of, the rotation of the respective drive shafts 94, 102. By ascertaining an absolute position of the first jaw 50 and the wedge 2603 at a point in time, the relative displacement of the first jaw 50 and the wedge 2603, based on the output signal from the encoders 1106, 1108 and the known pitches of the clamp screw 559 and of the wedge driver 2605, may be used to ascertain the absolute position of the first jaw 50 and the wedge 2603 at all times thereafter. The absolute position of the first jaw 50 and the wedge 2603 may be fixed and ascertained at the time that the surgical device 11 is first coupled to the flexible shaft 1620. Alternatively, the position of the first jaw 50 and the wedge 603 relative to, for example, the second jaw 80 may be determined based on the output signal from the encoders 1106, 1108.

Still further, the surgical device 11 may include optical sensors 3001, 3002, 3003 and 3004, as shown, for example, in FIG. 3(b). These optical sensors 3001, 3002, 3003 and 3004 may operate in conjunction with the function selector block 609. Depending on the position of the function selector block 609, corresponding signals to and from various ones of the optical sensors 3001, 3002, 3003 and 3004 are blocked, thereby providing a suitable controller with an indication when the surgical device 11 is in one of the four above-described functional positions, e.g., rotation, articulation, opening/closing of the jaws relative to each other, and firing the cutting and/or stapling mechanism.

As discussed above in connection with FIGS. 2(b) and 10, the surgical device 11 may include a data connector 1272 adapted by size and configuration to electrically and logically connect to connector 1670 of second coupling 1626. In the example embodiment, the data connector 1272 includes contacts 1276 equal in number to the number of contacts 1672 of connector 1670. The memory module 6041 is electrically and logically connected with the data connector 1272. Memory module 6041 may be in the form of, for example, an EEPROM, EPROM, etc. and may be contained, for example, within the staple tray 2604 of the replaceable staple cartridge 2600 in the second jaw 80 of the surgical device 11, as illustrated in FIG. 3(f).

Figure 14:
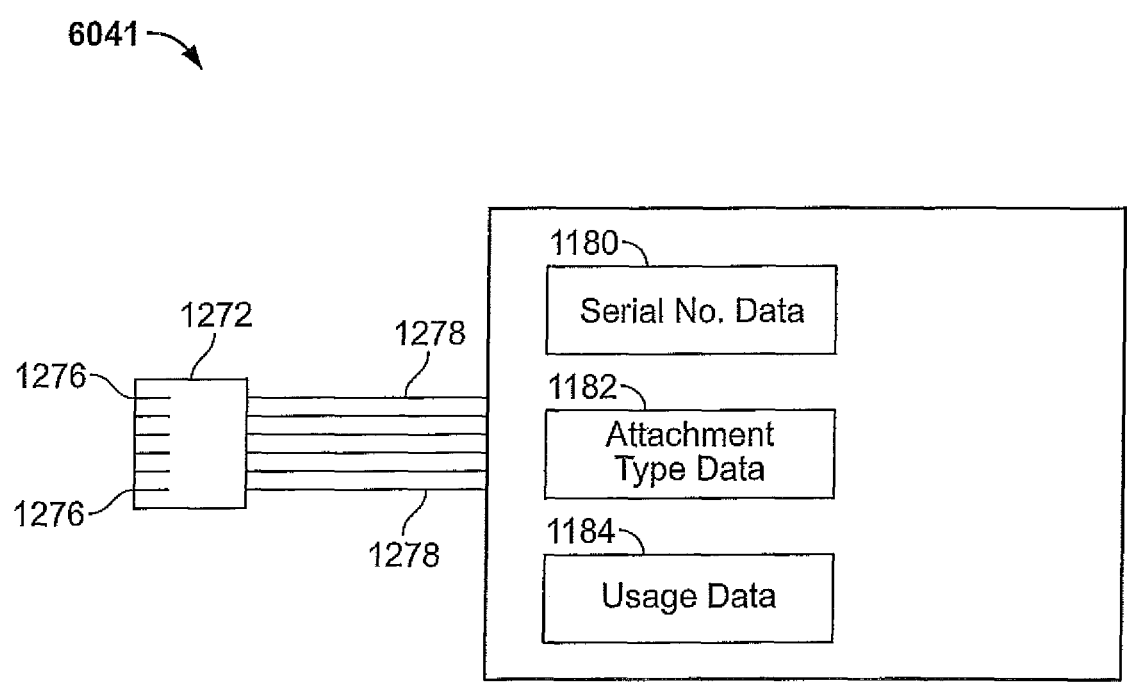
FIG. 14 schematically illustrates the memory module, according to an example embodiment of the present invention.

FIG. 14 schematically illustrates the memory module 6041. As seen in FIG. 14, data connector 1272 includes contacts 1276, each electrically and logically connected to the memory module 6041 via a respective line, e.g., flexible data cable 1278. The memory module 6041 may be configured to store, for example, a serial number data 1180, an attachment type identifier (ID) data 1182 and a usage data 1184. The memory module 6041 may additionally store other data. Both the serial number data 1180 and the ID data 1182 may be configured as read-only data. The serial number data 1180 and/or the ID data 1182 may be stored in a read-only section of the memory module 6041. In the example embodiment, serial number data 1180 may be data uniquely identifying the particular surgical device, whereas the ID data 1182 may be data identifying the type of the attachment, such as, e.g., for an electro-mechanical driver component 1610 to which other types of surgical instruments or attachments are attachable. The usage data 1184 represents usage of the particular attachment, such as, for example, the number of times the first jaw 50 of the surgical device 11 has been opened and closed, or the number of times that the wedge 2603 of the surgical device 11 has been advanced. The usage data 1184 may be stored in a read/write section of the memory module 6041.

It should be appreciated that the attachment attachable to the distal end 1624 of the flexible shaft 1620, e.g., surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 12, the controller 1122 is configured to read the ID data 1182 from the memory module 6041 of the surgical device 11 when the surgical device 11 is initially connected to the flexible shaft 1620. The memory module 6041 is electrically and logically connected to the controller 1122 via the line 1120 of the data transfer cable 1638. Based on the read ID data 1182, the controller 1122 is configured to read or select from the memory unit 1130, an operating program or algorithm corresponding to the type of surgical instrument or attachment connected to the flexible shaft 1620. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory module 6041 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical driver component 1610. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory module 6041 of the surgical device 11 and transferred to the controller 1122 via the data transfer cable 1638. Once the appropriate operating program or algorithm is read by or selected by or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 96, 100, 1684, 1690, 1696 via respective lines 1116, 1118, 1124, 1126, 1128 and is configured to control such motors 96, 100, 1684, 1690, 1696 in accordance with the read, selected or transmitted operating program or algorithm via the respective lines 1116, 1118, 1124, 1126, 1128.

Figure 15:
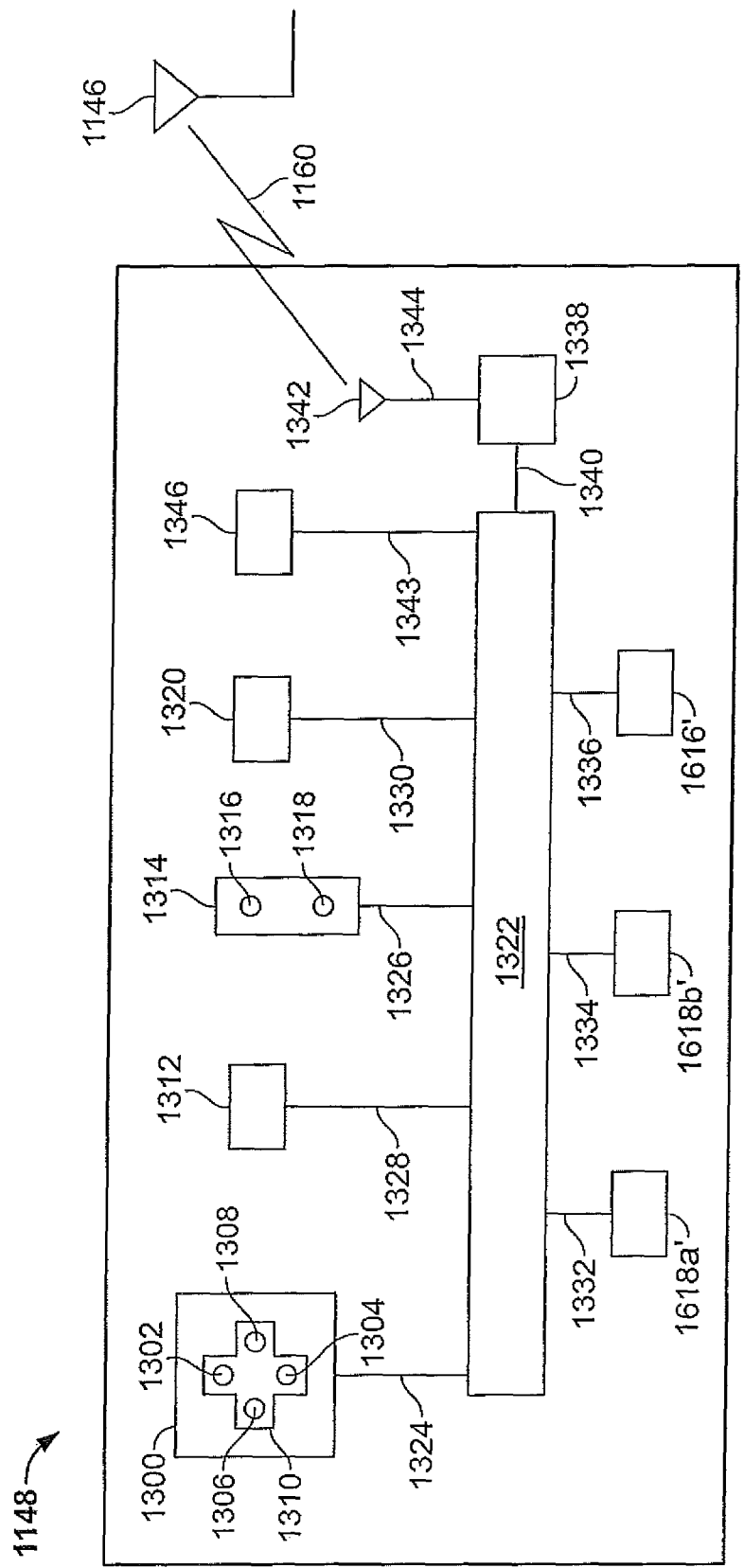
FIG. 15, there is seen a schematic view of a wireless RCU, according to an example embodiment of the present invention.

Referring now to FIG. 15, there is seen a schematic view of wireless RCU 1148. Wireless RCU 1148 includes a steering controller 1300 having a plurality of switches 1302, 1304, 1306, 1308 arranged under a four-way rocker 1310. The operation of switches 1302, 1304, via rocker 1310, controls the operation of first and second steering cables 1634, 1635 via third motor 1684. Similarly, the operation of switches 1306, 1308, via rocker 1310, controls the operation of third and fourth steering cables 1636, 1637 via fourth motor 1692. It should be appreciated that rocker 1310 and switches 1302, 1304, 1306, 1308 are arranged so that the operation of switches 1302, 1304 steers the flexible shaft 1620 in the north-south direction and that the operation of switches 1306, 1308 steers the flexible shaft 1620 in the east-west direction. Reference herein to north, south, east and west is made to a relative coordinate system. Alternatively, a digital joystick, an analog joystick, etc. may be provided in place of rocker 1310 and switches 1302, 1304, 1306, 1308. Potentiometers or any other type of actuator may also be used in place of switches 1302, 1304, 1306, 1308.

The wireless RCU 1148 further includes a steering engage/disengage switch 1312, the operation of which controls the operation of fifth motor 696 to selectively engage and disengage the steering mechanism. The wireless RCU 1148 also includes a two-way rocker 1314 having first and second switches 1316, 1318 operable thereby. The operation of these switches 1316, 1318 controls certain functions of the electro-mechanical driver component 1610 and any surgical instrument or attachment, such as the surgical device 11, attached to the flexible shaft 1620 in accordance with the operating program or algorithm corresponding to the attached device. For example, operation of the two-way rocker 1314 may control the opening and closing of the first jaw 50 and the second jaw 80 of the surgical device 11. The wireless RCU 1148 is provided with yet another switch 1320, the operation of which may further control the operation of the electro-mechanical driver component 1610 and the device attached to the flexible shaft 1620 in accordance with the operating program or algorithm corresponding to the attached device. For example, operation of the switch 1320 may initiate the advancement of the wedge 603 of the surgical device 11.

The wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. The wireless RCU 1148 may include indicators 1618a', 1618b', corresponding to the indicators 1618a, 1618b of front panel 1615, and a display device 1616', corresponding to the display device 1616 of the front panel 1615. If provided, the indicators 1618a', 1618b' are electrically and logically connected to controller 1322 via respective lines 1332, 1334, and the display device 1616' is electrically and logically connected to controller 1322 via line 1336. The controller 1322 is electrically and logically connected to a transceiver 1338 via line 1340, and the transceiver 1338 is electrically and logically connected to a receiver/transmitter 1342 via line 1344. A power supply, for example, a battery, may be provided in wireless RCU 1148 to power the same. Thus, the wireless RCU 1148 may be used to control the operation of the electro-mechanical driver component 1610 and the device 11 attached to the flexible shaft 1620 via wireless link 1160.

The wireless RCU 1148 may include a switch 1346 connected to a controller 1322 via line 1348. Operation of the switch 1346 transmits a data signal to the transmitter/receiver 1146 via wireless link 1160. The data signal includes identification data uniquely identifying the wireless RCU 1148. This identification data is used by the controller 1122 to prevent unauthorized operation of the electro-mechanical driver component 1610 and to prevent interference with the operation of the electro-mechanical driver component 610 by another wireless RCU. Each subsequent communication between the wireless RCU 1148 and the electro-mechanical device surgical 610 may include the identification data. Thus, the controller 1122 may discriminate between wireless RCUs and thereby allow only a single, identifiable wireless RCU 1148 to control the operation of the electro-mechanical driver component 1610 and the surgical device 11 attached to the flexible shaft 1620.

Based on the positions of the components of the surgical device attached to the flexible shaft 1620, as determined in accordance with the output signals from the encoders 1106, 1108, the controller 1122 may selectively enable or disable the functions of the electro-mechanical driver component 1610 as defined by the operating program or algorithm corresponding to the attached device. For example, for the surgical device 11, the firing function controlled by the operation of the switch 1320 may be disabled unless the space or gap between the first jaw 50 and the second jaw 80 is determined to be within an acceptable range.

Figure 16:
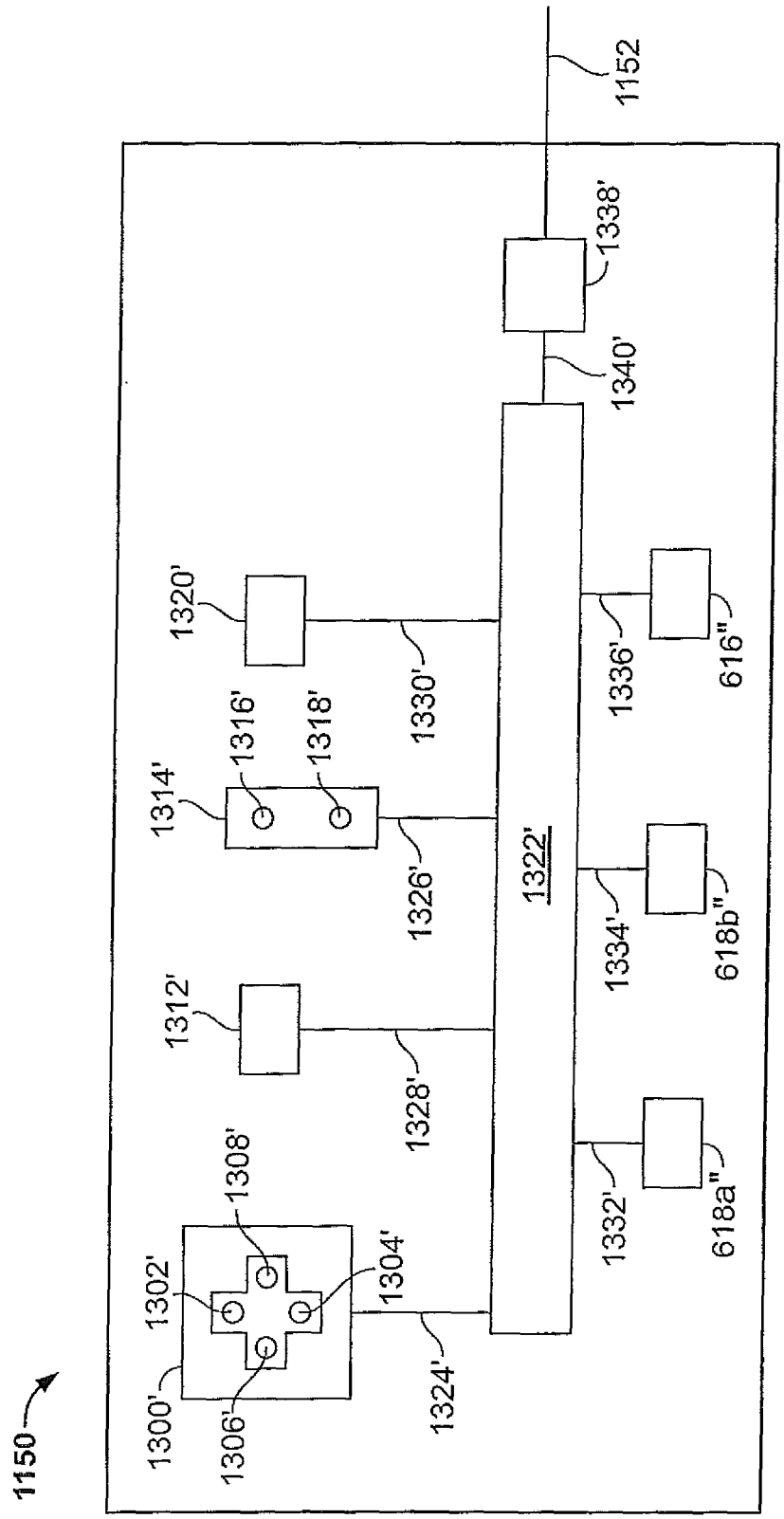
FIG. 16, there is seen a schematic view of a wired RCU, according to an example embodiment of the present invention.

Referring now to FIG. 16, there is seen a schematic view of a wired RCU 1150. In the example embodiment, wired RCU 1150 includes substantially the same control elements as the wireless RCU 1148 and further description of such elements is omitted. Like elements are indicated in FIG. 16 with an accompanying prime. It should be appreciated that the functions of the electro-mechanical driver component 1610 and the device attached to the flexible shaft 1620, e.g., the surgical device 11, may be controlled by the wired RCU 1150 and/or by the wireless RCU 1148. In the event of a battery failure, for example, in the wireless RCU 1148, the wired RCU 1150 may be used to control the functions of the electro-mechanical driver component 1610 and the device attached to the flexible shaft 1620.

As described hereinabove, the front panel 1615 of the housing 1614 includes the display device 1616 and the indicators 1618a, 1618b. The display device 1616 may include an alpha-numeric display device, such as an LCD display device. The display device 1616 may also include an audio output device, such as a speaker, a buzzer, etc. The display device 1616 is operated and controlled by controller 1122 in accordance with the operating program or algorithm corresponding to the device attached to the flexible shaft 1620, e.g., the surgical device 11. If no surgical instrument or attachment is so attached, a default operating program or algorithm may be read by or selected by or transmitted to controller 1122 to thereby control the operation of the display device 1616 as well as the other aspects and functions of the electro-mechanical driver component 1610. If the surgical device 11 is attached to the flexible shaft 1620, the display device 1616 may display, for example, data indicative of the gap between the first jaw 50 and the second jaw 80 as determined in accordance with the output signal of encoders 1106, 1108, as more fully described hereinabove.

Similarly, the indicators 1618a, 1618b are operated and controlled by the controller 1122 in accordance with the operating program or algorithm corresponding to the device attached to the flexible shaft 1620, e.g., the surgical device 11. The indicator 1618a and/or the indicator 1618b may include an audio output device, such as a speaker, a buzzer, etc., and/or a visual indicator device, such as an LED, a lamp, a light, etc. If the surgical device 11 is attached to the flexible shaft 1620, the indicator 1618a may indicate, for example, that the electro-mechanical driver component 1610 is in a power ON state, and the indicator 618b may, for example, indicate whether the gap between the first jaw 50 and the second jaw 80 is determined to be within the acceptable range. It should be appreciated that although two indicators 1618a, 1618b are described, any number of additional indicators may be provided as necessary. Additionally, it should be appreciated that although a single display device 1616 is described, any number of additional display devices may be provided as necessary.

The display device 1616' and the indicators 1618a', 1618b' of wired RCU 1150 and the display device 1616" and indicators 1618a", 1618b" of the wireless RCU 1148 are similarly operated and controlled by respective controller 1322, 1322' in accordance with the operating program or algorithm of the device attached to the flexible shaft 1620.

FIGS. 15 and 16 illustrate schematic views of a wireless and a wired RCU, respectively, each of which is configured to control, upon actuation by an operator, the various functions to be performed by the surgical device 11, e.g., rotation, articulation, opening/closing of the jaws relative to each other and firing a cutting and/or stapling mechanism. As set forth above, the surgical device 11 may also include various other arrangements for controlling the performance of these functions. For example, FIG. 3(b) illustrates that, in accordance with an embodiment of the present invention, the surgical device 11 may include a rotation/articulation control device 3006 and/or an open/close/fire control device 3007.

In the embodiment shown, the rotation/articulation control device 3006 is a joystick-type device that is positioned on a top surface of the handle 1103 so as to be actuatable by an operator's thumb when the operator is holding the handle 1103. The rotation/articulation control device 3006 may function similarly to the above-described four-way rocker 1310 of the wireless RCU 1148, in that movement of the rotation/articulation control device 3006 in a north-south direction may control the operation of the rotation driver 202 when the surgical device 11 is in a rotation mode, e.g., when the function selector block 609 is positioned in the first functional position. For example, when the rotation/articulation control device 3006 is moved by an operator in a north direction, e.g., by pushing the rotation/articulation control device 3006 distally, the rotation driver 202 may be actuated so as to cause the second rotatable drive shaft 1110b to rotate in a direction suitable to cause the shaft portion 11b to rotate in a clockwise direction relative to the handle 1103. Likewise, when the rotation/articulation control device 3006 is moved by an operator in a south direction, e.g., by pushing the rotation/articulation control device 3006 proximally, the rotation driver 202 may be actuated so as to cause the second rotatable drive shaft 1110b to rotate in a direction suitable to cause the shaft portion 11b to rotate in a counter-clockwise direction relative to the handle 1103. The surgical device 11 may be configured such that, if the function selector block 609 is not positioned in the first functional position, e.g., in rotation mode, the rotation driver 202 may be locked-out, e.g., prevented from moving whereby movement of the rotation/articulation control device 3006 in either of the north or south directions will not cause actuation of the rotation driver 202.

The rotation/articulation control device 3006 may also function similarly to the above-described four-way rocker 1310 of the wireless RCU 1148, in that movement of the rotation/articulation control device 3006 in an east-west direction may control the operation of the articulation driver 201 when the surgical device 11 is in a articulation mode, e.g., when the function selector block 609 is positioned in the second functional position. For example, when the rotation/articulation control device 3006 is moved by an operator in a west direction, e.g., by pushing the rotation/articulation control device 3006 to the left, the articulation driver 201 may be actuated so as to cause the second rotatable drive shaft 1110b to rotate in a direction suitable to cause the jaw portion 11a to rotate in a clockwise direction relative to the shaft portion 11b. Likewise, when the rotation/articulation control device 3006 is moved by an operator in an east direction, e.g., by pushing the rotation/articulation control device 3006 to the right, the articulation driver 201 may be actuated so as to cause the second rotatable drive shaft 1110b to rotate in a direction suitable to cause the jaw portion 11a to rotate in a counter-clockwise direction relative to the shaft portion 11b. The surgical device 11 may be configured such that, if the function selector block 609 is not positioned in the second functional position, e.g., in articulation mode, the articulation driver 201 may be locked-out, e.g., prevented from moving whereby movement of the rotation/articulation control device 3006 in either of the east or west directions will not cause actuation of the articulation driver 201.

Also, in the embodiment shown, the open/close/fire control device 3007 is a trigger-type device that is suitably positioned, e.g., on a bottom surface of the handle 1103, and sized so as to be actuatable by an operator's forefinger when the operator is holding the handle 1103. The open/close/fire control device 3007 may function similarly to the above-described two-way rocker 1314 of the wireless RCU 1148, in that movement of the open/close/fire control device 3007 in first and second directions may control the operation of the clamping driver 88 when the surgical device 11 is in a clamping mode, e.g., when the function selector block 609 is positioned in the third functional position. For example, when the open/close/fire control device 3007 is moved by an operator in a first direction, e.g., by depressing a top portion of the open/close/fire control device 3007, the clamping driver 88 may be actuated so as to cause the second rotatable drive shaft 1110b to rotate in a direction suitable to cause the first jaw to open relative to the second jaw 80. Likewise, when the open/close/fire control device 3007 is moved by an operator in a second direction, e.g., by depressing a bottom portion of the open/close/fire control device 3007, the clamping driver 88 may be actuated so as to cause the second rotatable drive shaft 1110b to rotate in a direction suitable to cause the first jaw to close relative to the second jaw 80. The surgical device 11 may be configured such that, if the function selector block 609 is not positioned in the third functional position, e.g., in clamping mode, the clamping driver 88 may be locked-out, e.g., prevented from moving whereby movement of the open/close/fire control device 3007 in either of the first or second directions will not cause actuation of the clamping driver 88.

The open/close/fire control device 3007 may also function similarly to the above-described switch 1320 of the wireless RCU 1148, in that movement of the open/close/fire control device 3007 in a first and second direction may control the operation of the firing driver 98 when the surgical device 11 is in a firing mode, e.g., when the function selector block 609 is positioned in the fourth functional position. For example, when the open/close/fire control device 3007 is moved by an operator in a first direction, e.g., by depressing a top portion of the open/close/fire control device 3007, the firing driver 98 may be actuated so as to cause the second rotatable drive shaft 1110b to rotate in a direction suitable to cause the firing shaft 557 and the wedge driver 2605 to rotate in a clockwise direction to thereby drive the wedge 2603 and/or the blade 51 through a section of tissue. Likewise, when the open/close/fire control device 3007 is moved by an operator in a second direction, e.g., by depressing a bottom portion of the open/close/fire control device 3007, the firing driver 98 may be actuated so as to cause the firing shaft 557 and the wedge driver 2605 to rotate in a counter-clockwise direction to thereby retract the wedge 2603 and/or the blade 51 back to their initial positions. The surgical device 11 may be configured such that, if the function selector block 609 is not positioned in the fourth functional position, e.g., in firing mode, the firing driver 98 may be locked-out, e.g., prevented from moving whereby movement of the open/close/fire control device 3007 in either of the first or second directions will not cause actuation of the firing driver 98.

The transmission of signals from the rotation/articulation control device 3006 and/or the open/close/fire control device 3007 to appropriate controllers may be performed either by wired connection or wireless transmission, using the communication arrangements similar to those illustrated in FIGS. 15 and 16, respectively.

The surgical device 11 of the present invention may also employ an imaging arrangement, e.g., a camera. In such an arrangement, an imaging device may be positioned at a suitable location of the surgical device 11 so as to provide to an operator imaging data corresponding to a surgical site. Advantageously, the imaging device is articulatable along with the jaw portion 11a, such that appropriate image data may be provided to an operator irrespective of whether the jaw portion 11a has been rotated clockwise or counter-clockwise relative to the shaft portion 11b.

As set forth above, one problem with conventional surgical devices, and in particular with the conventional linear clamping, cutting and stapling devices such as that illustrated in FIG. 1, is that the opposing jaws may be difficult to maneuver within a patient. It may be necessary for a surgeon to move the opposing jaws between various angles in order to position the desired tissue between the opposing jaws. However, it may also be desirable to make an incision in a patient that is as small as possible, and the small size of an incision limits the degree to which the opposing jaws may be maneuvered. Example embodiments of the present invention may provide improved maneuverability of a surgical device, e.g., the surgical device 11, within a patient.

Another problem with the conventional surgical devices, and in particular with the foregoing linear clamping, cutting and stapling devices such as that illustrated in FIG. 1, is that the opposing jaws may not be sufficiently hemostatic. Specifically, the opposing jaws of the foregoing surgical devices may not be clamped together with sufficient force, thereby reducing the effectiveness of the surgical device. Example embodiments of the present invention may provide improved clamping of a section of tissue disposed between the jaws of a surgical device, e.g., the surgical device 11, thereby providing a sufficiently hemostatic condition with respect to the clamped section of tissue.

Figure 2C:
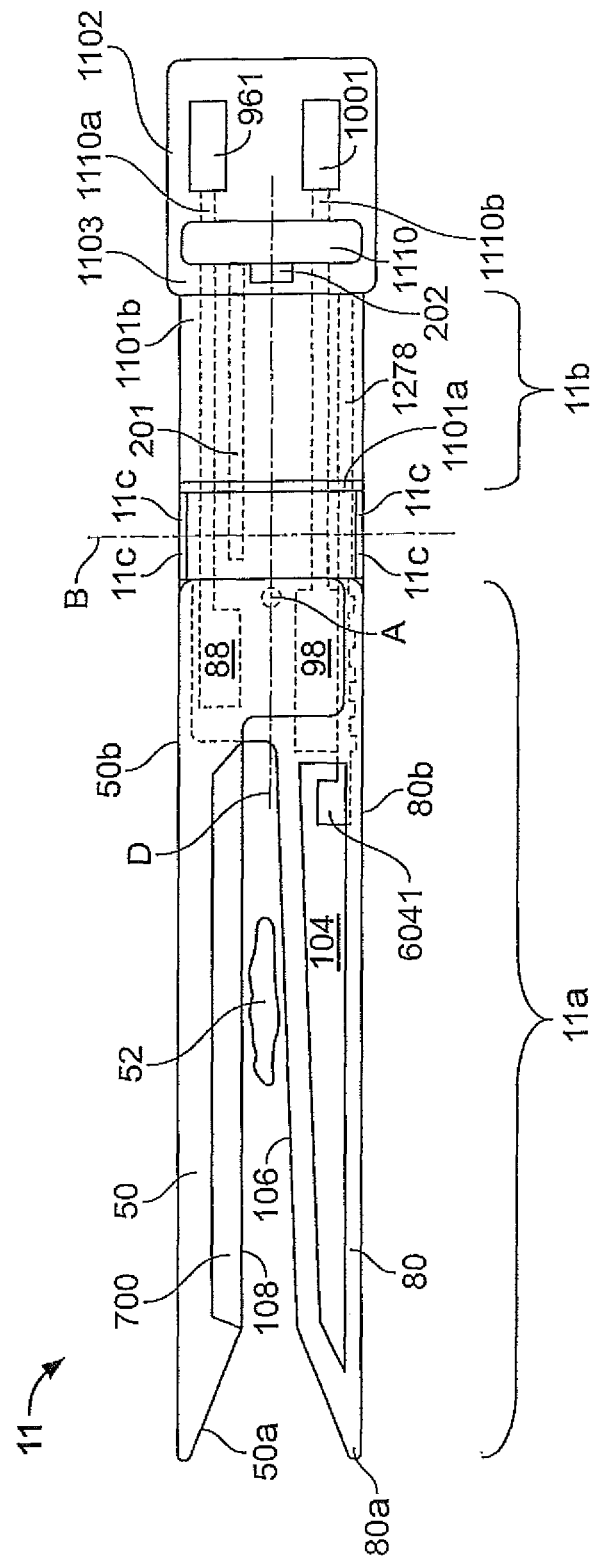
FIG. 2(c) is a schematic diagram that illustrates some of the components of a surgical device, according to another example embodiment of the present invention.

As set forth above, the surgical device of the present invention may employ motors to drive the first and second rotatable drive shafts 1110a and 1110b, wherein the motors are integral with the surgical device 11. For example, FIG. 2(c) is a schematic diagram that illustrates an arrangement of the surgical device 11, according to an example embodiment of the present invention, in which the first motor 961 and second motor 1001 are arranged within the handle 1103, such that the first and second rotatable drive shafts 1110a and 1110b are connected to the first and second motors 961, 1001, respectively. FIGS. 17(a) through 18(d) provide additional details of such an embodiment, and particularly, an arrangement in which various components, e.g., motors, power source, etc., are integral with the device.

Figure 17A:
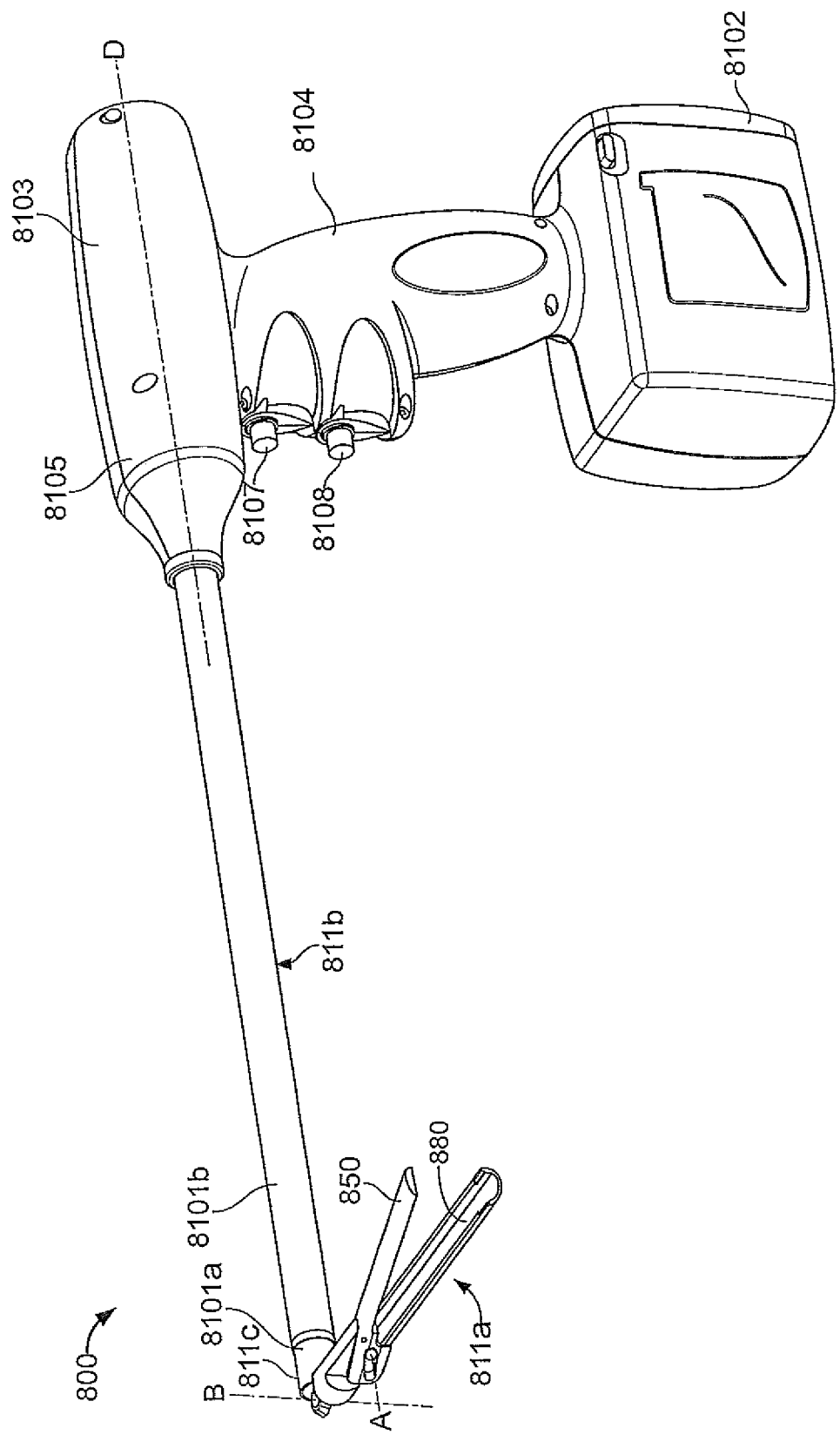
FIG. 17(a) is a side perspective view of such a surgical device, according to an example embodiment of the present invention.

FIG. 17(a) is a side perspective view of such a surgical device, according to an example embodiment of the present invention. Referring now to FIG. 17(a), there is shown a surgical device 800 that is configured to stand alone, e.g., that includes various motors, drive shafts, control systems, etc., in an integral arrangement such that attachment to a separate electro-mechanical surgical system is eliminated. Such an arrangement may include the advantage that the surgical device 800 is not connected prior to use to a separately-disposed drive system. The surgical device 800 is configured so as to be particularly well-suited for insertion into the body of a patient, e.g., via a cannula (not shown). In the embodiment shown, the surgical device 800 is a clamping, cutting and stapling device. The surgical device 800 includes a jaw portion 811a that is pivotably coupled to a shaft portion 811b by a hinge portion 811c. The jaw portion 811*a* includes a first jaw 850 having a distal end and a proximal end, and a second jaw 880 having a distal end and a proximal end. The first jaw 850 and the second jaw 880 are pivotably coupled relative to each other at or near their respective proximal ends. As shown, the first jaw 850 and the second jaw 880 are pivotable relative to each other about pivot axis A. In this arrangement, the jaws are configured such that, upon opening and closing of the first jaw 850 relative to the second jaw 880 and at points in the movement of the first jaw 850 relative to the second jaw 880, both the first jaw 850 and the second jaw 880, e.g., their longitudinal axes, remain within a plane. It should be understood, however, that the surgical device 800 may instead be configured such that the first jaw 850 and the second jaw 880 are pivotable relative to each other about a pivot axis that is oriented differently from that shown.

As mentioned above, the jaw portion 811*a* is pivotably coupled to the shaft portion 811*b* by the hinge portion 811*c*. Specifically, the jaw portion 811*a* is pivotable relative to the shaft portion 811*b* about a pivot axis B, which may be positioned at any location on or between the jaw portion 811*a* and the shaft portion 811*b*, and at any circumferential location relative to the jaw portion 811*a* and the shaft portion 811*b*. In the example embodiment shown, the pivot axis B is oriented vertically, and within the page, in the view shown. In this arrangement, the jaw portion 811*a* and the shaft portion 811*b* are configured such that, upon articulation of the jaw portion 811*a* relative to the shaft portion 811*b* and at any point in the movement of the jaw portion 811*a* relative to the shaft portion 811*b*, the jaw portion 811*a* and the shaft portion 811*b* remain within a plane that is perpendicular to the pivot axis B. It should be recognized that, in other example embodiments, the pivot axis B may have a different orientation, so as to enable the jaw portion 811*a* to pivot within a different plane. The jaw portion 811*a* may be pivotable to and between any angles relative to the shaft portion 811*b*, such that the jaw portion 811*a* can be selectively positioned as desired during use.

Furthermore, the surgical device 800 may provide rotation of various components about a longitudinal axis of the surgical device 800. For example, in various embodiments, the jaw and/or shaft portions 811*a*, 811*b* may be rotatable relative to a handle 8103 (described in additional detail below), that is attached to a proximal end of the shaft portion 811*b*, about a longitudinal axis D of the handle 8103, e.g., the longitudinal axis D of the handle 8103 at the point where the handle 8103 meets the shaft portion 811*b*. The shaft portion 811*b* may include a distal portion 8101*a*, to which the jaw portion 811*a* is connected, and a proximal portion 8101*b*, which may be connected to the handle 8103.

Generally, the handle 8103 may be grasped by an operator to operate the surgical device 800. The handle 8103 has a proximal portion 8102, which in the embodiment shown, forms a base. In addition, the handle 8103 has an intermediate portion 8104, which includes several finger-actuated control buttons 8107, 8108 and rocker devices 8117, 8118. Still further, the handle 8103 has a distal portion 8105 that is connected to the shaft portion 811*b*.

Figure 17B:
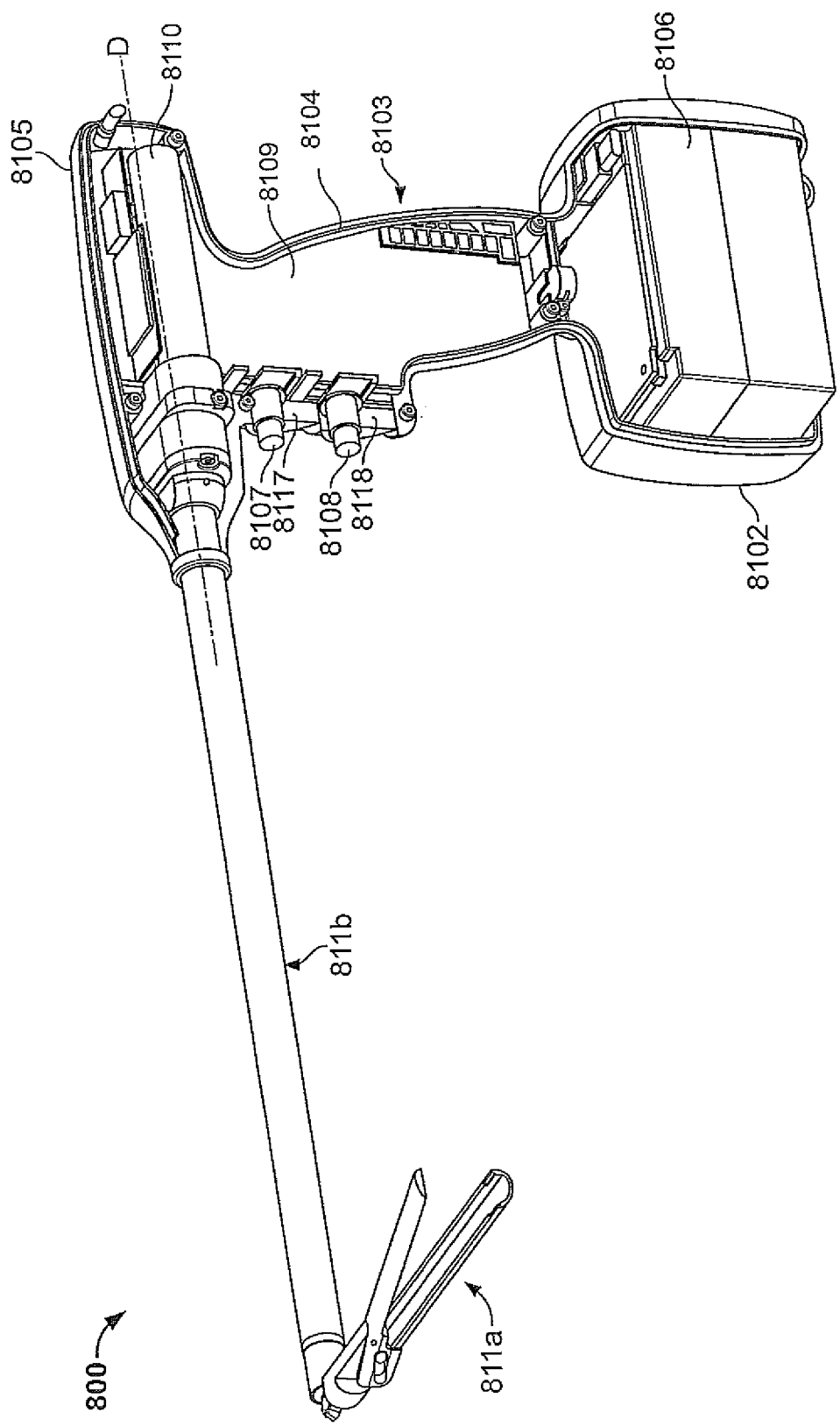
FIG. 17(b) is a partial cutaway view of the surgical device of FIG. 17(a), showing additional details of the components internal to the handle.
Figure 17C:
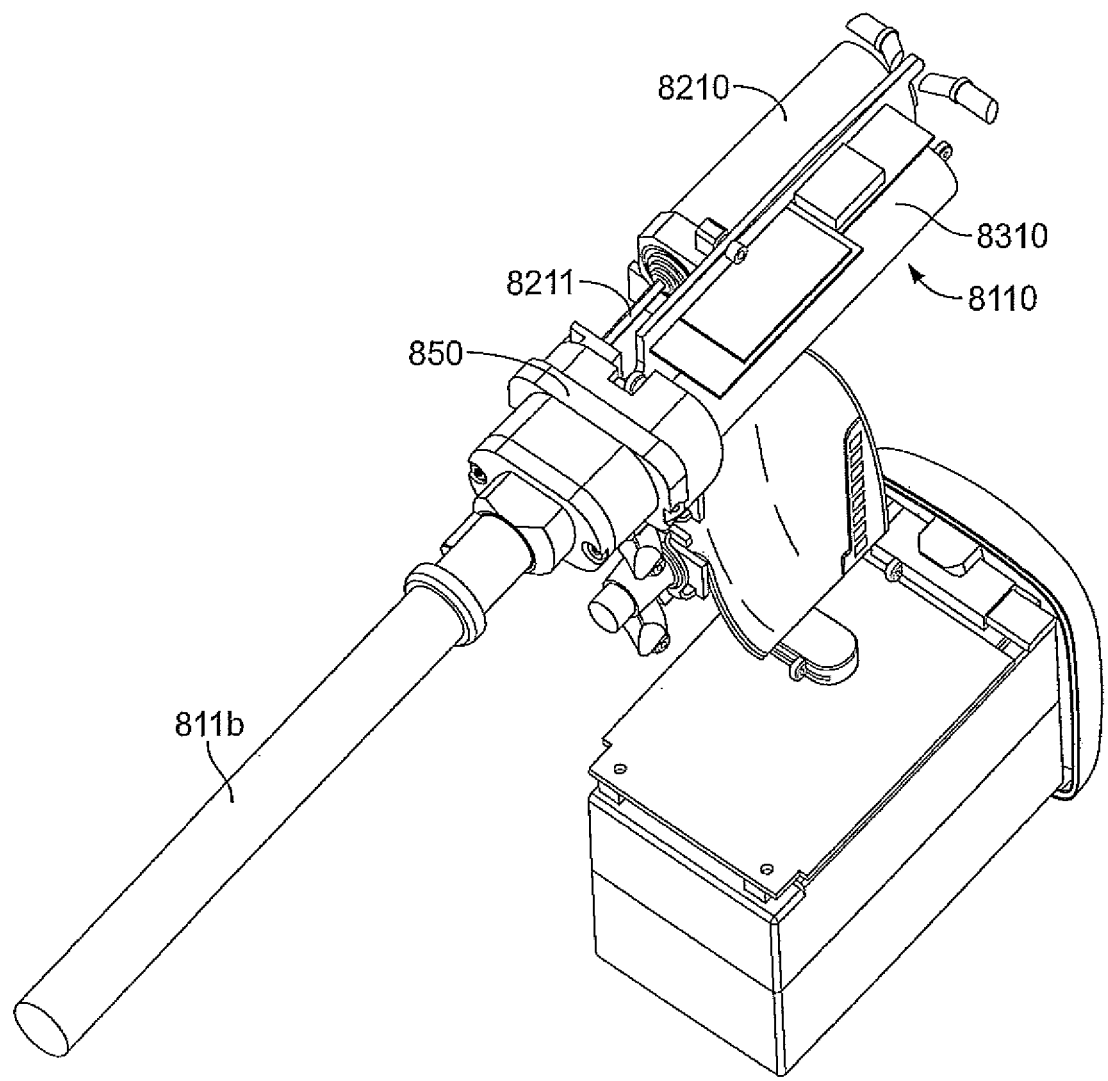
FIG. 17(c) is a partially cutaway, top perspective view of the surgical device of FIG. 17(a), which illustrates additional details of the drive mechanism.
Figure 18A:
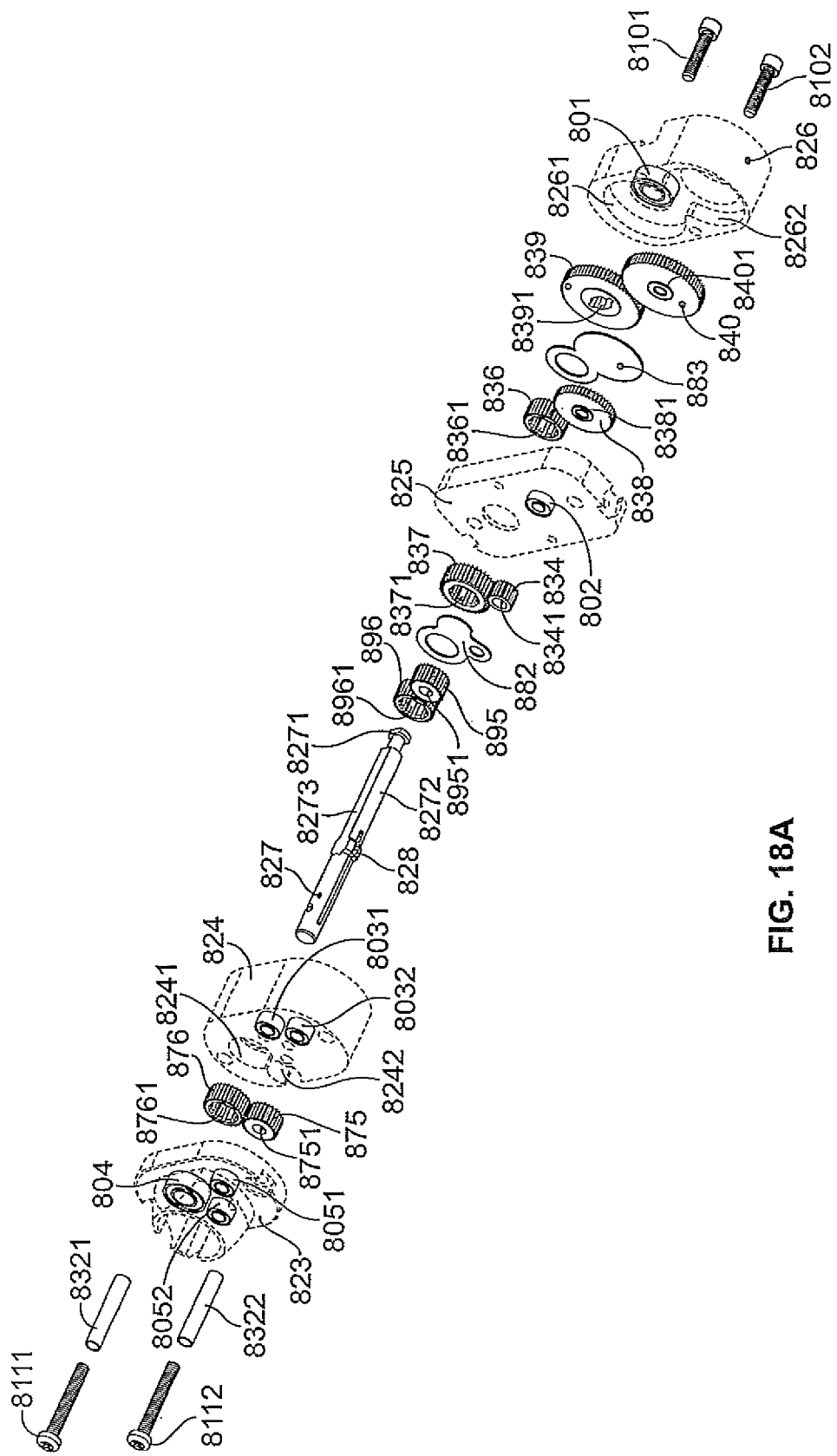
FIG. 18(a) is an exploded perspective view of a selector gearbox assembly.
Figure 18D:
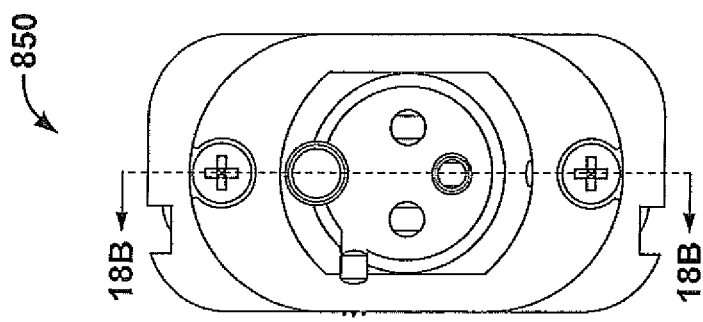
FIG. 18(d) is a front view of the selector gearbox assembly of FIG. 18(a).
Figure 18C:
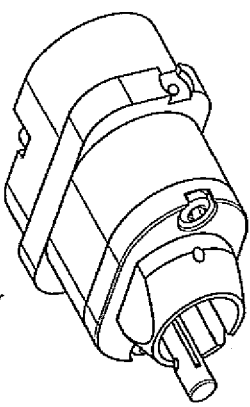
FIG. 18(c) is a perspective view of the selector gearbox assembly of FIG. 18(a)
Figure 18B:
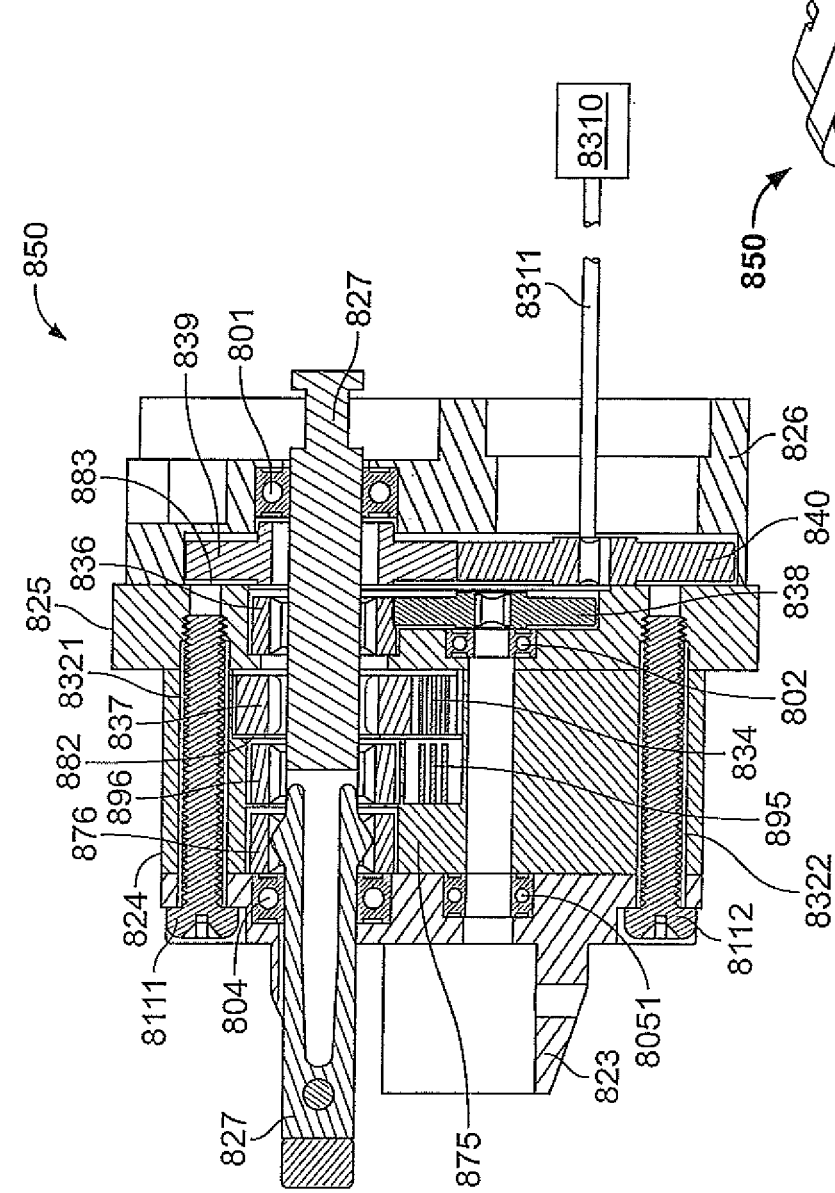
FIG. 18(b) is a cross-sectional view of the selector gearbox assembly of FIG. 18(a)

FIG. 17(*b*) is a partial cutaway view of the surgical device 800, showing additional details of the components internal to the handle 8103. As shown, the proximal portion 8102 of the handle 8103 provides a housing in which a power source, e.g., a battery 8106, may be situated. The battery 8106 may be configured to supply power to any of the components of the surgical device 800. As set forth above, this arrangement may provide an advantage over other surgical devices in that attachment of the surgical device 800 to a power source of a separate electro-mechanical surgical system may be eliminated.

Likewise, the intermediate portion 8104 of the handle 8103 provides a housing in which a circuit board 8109 may be situated. The circuit board 8109 may be configured to control the various operations of the surgical device 800, as set forth in additional detail below. As set forth above, this arrangement may provide an advantage over other surgical devices in that attachment of the surgical device 800 to a control system, e.g., software and the like, of a separate electro-mechanical surgical system may be eliminated.

Located on the proximal side of the intermediate portion 8104 of the handle 8103 are control buttons 8107, 8108 and rocker devices 8117, 8118. Each one of the control buttons 8107, 8108 and rocker devices 8117, 8118 include a respective magnet that is moved by the actuation of an operator. In addition, the circuit board 8109 includes, for each one of the control buttons 8107, 8108 and rocker devices 8117, 8118, respective Hall-effect switches that are actuated by the movement of the magnets in the control buttons 8107, 8108 and rocker devices 8117, 8118. For example, located immediately proximal to the control button 8107 is a Hall-effect switch that is actuated upon the movement of a magnet within the control button 8107 upon the operator actuating the control button 8107. The actuation of the Hall-effect switch causes the circuit board 8109 to provide appropriate signals to a function selection module 8210 and an input drive component 8310 (explained further below) to close the first jaw 850 relative to the second jaw 880 and/or to fire a stapling/cutting cartridge within the second jaw 880.

Also, located immediately proximal to the rocker device 8117 is a Hall-effect switch that is actuated upon the movement of a magnet within the rocker device 8117 upon the operator actuating the rocker device 8117. The actuation of the Hall-effect switch causes the circuit board 8109 to provide appropriate signals to the function selection module 8210 and the input drive component 8310 to articulate the jaw portion 811*a* relative to the shaft portion 811*b*. Advantageously, movement of the rocker device 8117 in a first direction may cause the jaw portion 811*a* to articulate relative to the shaft portion 811*b* in a first direction, while movement of the rocker device 8117 in an opposite, e.g., second, direction may cause the jaw portion 811*a* to articulate relative to the shaft portion 811*b* in an opposite, e.g., second, direction.

Furthermore, located immediately proximal to the control button 8108 is a Hall-effect switch that is actuated upon the movement of a magnet within the control button 8108 upon the operator actuating the control button 8108. The actuation of the Hall-effect switch causes the circuit board 8109 to provide appropriate signals to a function selection module 8210 and an input drive component 8310 to open the first jaw 850 relative to the second jaw 880.

In addition, located immediately proximal to the rocker device 8118 is a Hall-effect switch that is actuated upon the movement of a magnet within the rocker device 8118 upon the operator actuating the rocker device 8118. The actuation of the Hall-effect switch causes the circuit board 8109 to provide appropriate signals to the function selection module 8210 and the input drive component 8310 to rotate the shaft portion 811*b*, or at least a portion thereof, relative to the handle 8103. Advantageously, movement of the rocker device 8118 in a first direction may cause the shaft portion 811*b*, or at least a portion thereof, to rotate relative to the handle 8103 in a first direction, while movement of the rocker device 8118 in an opposite, e.g., second, direction may cause the shaft portion 811*b*, or at least a portion thereof, to rotate relative to the handle 8103 in an opposite, e.g., second, direction.

Still further, the distal portion 8105 of the handle 8103 provides a housing in which a drive mechanism 8110 may be situated. The drive mechanism 8110 may be configured to drive shafts and/or gear components in order to perform the various operations of the surgical device 800, as set forth above. For example, the drive mechanism 8110 may be configured to drive shafts and/or gear components in order to selectively move the jaw portion 811*a* relative to the shaft portion 811*b*, to rotate the shaft portion 811*b* (or portions of the surgical device 800 that are distal thereto) about longitudinal axis D relative to the handle 8103, to move the first jaw 850 relative to the second jaw 880, and/or to fire a stapling and cutting cartridge within the second jaw 880. As set forth above, this arrangement may provide an advantage over other surgical devices in that attachment of the surgical device 800 to a drive system, e.g., motors, etc., of a separate electro-mechanical surgical system may be eliminated.

FIG. 17(*c*) is a partially cutaway, top perspective view of the surgical device 800, which illustrates additional details of the drive mechanism 8110. As shown in FIG. 17(*c*), the drive mechanism 8110 may include a selector gearbox assembly 850 that is located immediately proximal relative to the shaft portion 811. Proximal to the selector gearbox assembly 850 is a function selection module 8210 that functions to selectively move gear elements within the selector gearbox assembly 850 into engagement with an input drive component 8310.

FIGS. 18(*a*) through 18(*d*) illustrate various views of the selector gearbox assembly 850. Specifically, FIG. 18(*a*) is an exploded perspective view of the selector gearbox assembly 850. Referring to FIG. 18(*a*), the sga 850 includes a pair of screws 8101 and 8102. Each one of the pair of screws 8101 and 8102 are received within respective openings of a proximal housing 826. In addition, a bearing 801 is seated within a correspondingly shaped recess of the proximal housing 826. The proximal housing 826 also has a pair of adjacent and overlapping recesses 8261, 8262 in its distal face. A first recess 8261 is configured to receive a spur gear 839 having gear teeth about its outer circumference. In addition, the spur gear 839 has a centrally-disposed orifice 8391 extending therethrough, the centrally-disposed orifice 8391 defining an opening that has an elongated, slotted shape. A second recess 8262 is configured to receive a spur gear 840 having gear teeth about its outer circumference. In addition, the spur gear 840 has a centrally-disposed orifice 8401 extending therethrough, the centrally-disposed orifice 8401 defining a non-circular opening. The gear teeth of the spur gear 839 are meshingly engaged with the gear teeth of the spur gear 840. Located distally relative to the spur gears 839, 840 is a spacer element 883.

Located distally relative to the spacer element 883 is a spur gear 836 having gear teeth about its outer circumference. In addition, the spur gear 836 has a centrally-disposed orifice 8361 extending therethrough. The centrally-disposed orifice 8361 defines an opening that has longitudinally-extending slots positioned at various intervals along its inner circumferential surface. The selector gearbox assembly 850 also includes a spur gear 838 having gear teeth about its outer circumference. In addition, the spur gear 838 has a centrally-disposed orifice 8381 extending therethrough, the centrally-disposed orifice 8381 defining a non-circular opening. The gear teeth of the spur gear 836 are meshingly engaged with the gear teeth of the spur gear 838. Located distally relative to the spur gear 838 is a bearing 802. The bearing 802, as well as the spur gears 836, 838 are maintained within respective recesses of a first intermediate housing 825.

Located distally relative to the first intermediate housing 825 is a spur gear 837 having gear teeth about its outer circumference. In addition, the spur gear 837 has a centrally-disposed orifice 8371 extending therethrough. The centrally-disposed orifice 8371 defines an opening that has longitudinally-extending slots positioned at various intervals along its inner circumferential surface. The selector gearbox assembly 850 also includes a spur gear 834 having gear teeth about its outer circumference. In addition, the spur gear 834 has a centrally-disposed orifice 8341 extending therethrough, the centrally-disposed orifice 8341 defining a non-circular opening. The gear teeth of the spur gear 837 are meshingly engaged with the gear teeth of the spur gear 834. Located distally relative to the spur gears 834, 837 is a spacer 882.

Located distally relative to the spacer element 882 is a spur gear 896 having gear teeth about its outer circumference. In addition, the spur gear 896 has a centrally-disposed orifice 8961 extending therethrough. The centrally-disposed orifice 8961 defines an opening that has longitudinally-extending slots positioned at various intervals along its inner circumferential surface. The selector gearbox assembly 850 also includes a spur gear 895 having gear teeth about its outer circumference. In addition, the spur gear 895 has a centrally-disposed orifice 8951 extending therethrough, the centrally-disposed orifice 8951 defining a non-circular opening. The gear teeth of the spur gear 896 are meshingly engaged with the gear teeth of the spur gear 895. Located distally relative to the spur gears 895, 896 are bearings 8031, 8032. The bearings 8031, 8032, as well as the spur gears 895, 896 are maintained within respective recesses of a second intermediate housing 824.

The second intermediate housing 824 also has a pair of adjacent and overlapping recesses 8241, 8242 in its distal face. A first recess 8241 is configured to receive a spur gear 876 having gear teeth about its outer circumference. In addition, the spur gear 876 has a centrally-disposed orifice 8761 extending therethrough, the centrally-disposed orifice 8761 defining an opening that has longitudinally-extending slots positioned at various intervals along its inner circumferential surface. A second recess 8242 is configured to receive a spur gear 875 having gear teeth about its outer circumference. In addition, the spur gear 875 has a centrally-disposed orifice 8751 extending therethrough, the centrally-disposed orifice 8751 defining a non-circular opening. The gear teeth of the spur gear 876 are meshingly engaged with the gear teeth of the spur gear 875.

Located distally relative to the spur gears 875, 876 are bearings 804, 8051 and 8052. The bearings 804, 8051 and 8052 are maintained within respective recesses of a distal housing 823. The proximal housing 826, the first intermediate housing 825, the second intermediate housing 824 and the distal housing 823 are attached to each other via screws 8101 and 8102 from the proximal end of the selector gearbox assembly 850 and via screws 8111 and 8112 (maintained in sleeves 8321 and 8322, respectively) from the distal end thereof.

The selector gearbox assembly 850 also includes a selector rod 827. The selector rod has a head 8271 at its proximal end. The head 8271 is configured to engage the shaft 8211 of the function selection module 8210. In addition, the selector rod 827 includes a proximal portion 8272. The proximal portion 8272 has oppositely-disposed flat portions 8273 along its outer circumference. The proximal portion 8272 resides within the opening 8391 of the spur gear 839, the flat portions 8273 being keyed therewithin such that the selector rod 827 is locked into rotatable engagement with the spur gear 839. The selector rod 827 also includes oppositely-disposed nubs 828 at about its axial midpoint. The nubs 828 extend radially outerwardly from the outer circumference of the selector rod 827.

In operation, the jaw portion 811a is maintained in an initial position in which it is axially aligned with the shaft portion 811b, such as a position similar to the position shown in FIG. 3(b). In this position, the surgical device 800 may be inserted, e.g., through a trocar, into a surgical site. Depending on the position of the incision and the tissue to be clamped, stapled and cut, the user may then operate the surgical device 800.

Once the surgical device 800 has been inserted within a patient, the shaft portion 811b, or at least a portion thereof, may be rotated, e.g., the shaft portion 811b may be rotated relative to and about the longitudinal axis D of the handle 8103. Of course, it should be recognized that, in the example embodiment described herein, rotation of the shaft portion 811b relative to the handle 8103 also causes rotation of the jaw portion 811a disposed distally relative to the shaft portion 811b. In other embodiments, rotation may be achieved by the jaw portion 811a rotating relative to and about a longitudinal axis of the shaft portion 811b, or, in an embodiment in which the jaw portion 811a is coupled directly to the handle 8103, by the jaw portion 811a rotating relative to and about a longitudinal axis of the handle 8103. For the purposes of this application, the "shaft portion" is intended to refer to any portion of the component of the surgical device that is located distally relative to a handle.

Once the shaft portion 811b has been rotated relative to the handle 8103, the surgical device 800 may be employed to move the jaw portion 811a relative to the shaft portion 811b, e.g., to pivot the jaw portion 811a about axis B relative to the shaft portion 811b. In order to perform this articulation function, the surgical device 800 may be operated such that the function selector module 8210 is moved to an articulation function position. As set forth above, in this articulation function position, the function selector module 8210 causes engagement of the main drive shaft 8311 of the main motor drive component 8310 with appropriate gears of the selector gearbox assembly 850, as set forth more fully below.

Generally, the function selector module 8210 is actuated such that the shaft 8211 moves the selector rod 827 to an articulation position. In the embodiment shown, the articulation function position is a position in which the selector rod 827 is moved to its proximal-most position. With the selector rod 827 here, the nubs 828 of the selector rod 827 are positioned within the longitudinal slots located on the inner circumferential surface of the opening 8361 of the spur gear 836.

With the selector rod 827 so positioned, the main motor drive component is then actuated. Specifically, an operator may move the finger-actuated rocker device 8117 in a first direction. The corresponding Hall-effect switch that is located immediately proximal to the rocker device 8117 senses the movement of the magnet in the rocker device 3117 and generates an appropriate signal that is sent to, and received by, the main motor drive component 8310. The main motor drive component 8310 turns the shafts 8311 in response to the received signals. In an example embodiment, the main motor drive component 8310 may turn the shaft 8311 in a clockwise direction (as previously explained, for the sake of simplicity, all references herein to a rotational direction, e.g., clockwise or counterclockwise, refer to a view from the proximal end of the surgical device towards the distal end of the surgical device 800, unless otherwise noted; furthermore, it should be recognized that, while the disclosure hereinbelow includes, for each of the components of the surgical device 800, various references to rotational directions in order to perform a specific function, these directions are merely exemplary because certain components may be differently configured, e.g., threaded portions may have a right-hand thread as opposed to a left-hand thread, etc., such that the rotational directions set forth herein may be reversed in order to perform the same below-described functions).

The distal end of the shaft 8311 is keyed to the non-circular opening 8401 of the spur gear 840, such that clockwise rotation of the shaft 8311 causes the spur gear 840 to rotate in a clockwise direction. Because the gear teeth on the outer circumference of the spur gear 840 are meshingly engaged with the gear teeth on the outer circumference of the spur gear 839, clockwise rotation of the spur gear 840 causes the spur gear 839 to rotate in a counter-clockwise direction. As set forth above, the proximal portion 8272 of the selector rod 827 is keyed within the non-circular opening 8391 of the spur gear 839, such that counter-clockwise rotation of the spur gear 839 causes the selector rod 827 to rotate in a counter-clockwise direction. Also, because the selector rod 827 is in an axial position in which the nubs 828 of the selector rod 827 are positioned within the longitudinal slots located on the inner circumferential surface of the opening 8361 of the spur gear 836, counter-clockwise rotation of the selector rod 827 causes the spur gear 836 to rotate in a counter-clockwise direction.

Because the gear teeth on the outer circumference of the spur gear 836 are meshingly engaged with the gear teeth on the outer circumference of the spur gear 838, counter-clockwise rotation of the spur gear 836 causes the spur gear 838 to rotate in a clockwise direction. The non-circular opening 8381 of the spur gear 838 is keyed to a shaft, such as the shaft 525 illustrated in, e.g., FIG. 4(d), such that clockwise rotation of the spur gear 838 causes articulation of the jaw portion 811a relative to the shaft portion 811b about axis B in a first, e.g., counter-clockwise direction (when viewed from above) in the manner described hereinabove or in any other manner. Of course, the movement, e.g., articulation, in the opposite direction may also be accomplished by reversing the direction in which the above-described gears are caused to rotate.

Once the jaw portion 811a has been articulated about axis B relative to the shaft portion 811b, the jaws 850, 880 may be moved, e.g., opened, so as to enable a section of tissue to be disposed therebetween. In order to perform this opening function, the surgical device 800 may be operated such that the function selector module 8210 is moved to an opening function position. As set forth above, in this opening function position, the function selector module 8210 causes engagement of the main drive shaft 8311 of the main motor drive component 8310 with appropriate gears of the selector gearbox assembly 850, as set forth more fully below.

Generally, the function selector module 8210 is actuated such that the shaft 8211 moves the selector rod 827 to a clamping position. In the embodiment shown, the clamping function position is a position in which the selector rod 827 is moved to an axial position at which the nubs 828 of the selector rod 827 are positioned within the longitudinal slots located on the inner circumferential surface of the opening 8961 of the spur gear 896.

With the selector rod 827 so positioned, the main motor drive component 8310 is then actuated. Specifically, an operator may move the finger-actuated control button 8108. The corresponding Hall-effect switch that is located immediately proximal to the control button 8108 senses the movement of the magnet in the control button 8108 and generates an appropriate signal that is sent to, and received by, the main motor drive component 8310. The main motor drive component 8310 turns the shaft 8311 in response to the received signals. In an example embodiment, the main motor drive component 8310 may turn the shaft 8311 in a clockwise direction.

Since the distal end of the shaft 8311 is keyed to the non-circular opening 8401 of the spur gear 840, clockwise rotation of the shaft 8311 causes the spur gear 840 to rotate in a clockwise direction. Also, because the gear teeth on the outer circumference of the spur gear 840 are meshingly engaged with the gear teeth on the outer circumference of the spur gear 839, clockwise rotation of the spur gear 840 causes the spur gear 839 to rotate in a counter-clockwise direction. As set forth above, the proximal portion 8272 of the selector rod 827 is keyed within the non-circular opening 8961 of the spur gear 896, such that counter-clockwise rotation of the spur gear 839 causes the selector rod 827 to rotate in a counter-clockwise direction. Also, because the selector rod 827 is in an axial position in which the nubs 828 of the selector rod 827 are positioned within the longitudinal slots located on the inner circumferential surface of the opening 8961 of the spur gear 896, counter-clockwise rotation of the selector rod 827 causes the spur gear 896 to rotate in a counter-clockwise direction.

Because the gear teeth on the outer circumference of the spur gear 896 are meshingly engaged with the gear teeth on the outer circumference of the spur gear 895, counter-clockwise rotation of the spur gear 896 causes the spur gear 895 to rotate in a clockwise direction. The non-circular opening 8951 of the spur gear 895 is keyed to a shaft, such as the shaft 527 illustrated in, e.g., FIG. 4(*d*), such that clockwise rotation of the spur gear 895 causes the first jaw 850 to move, e.g., be opened, relative to the second jaw 880) in the manner described hereinabove or in any other manner.

Once the first and second jaws 850, 880 have been opened to a desired position relative to each other, and once a section of tissue desired to be operated on is satisfactorily positioned between the first and second jaws 850, 880 of the surgical device 800, the first and second jaws 850, 880 are closed so as to clamp the section of tissue therebetween.

In order to close the first and second jaws 50, 80 relative to each other, the function selector module 8210 may remain in the clamping function position. As set forth above, in this clamping function position, the selector rod 827 is positioned such that the nubs 828 of the selector rod 827 are positioned within the longitudinal slots located on the inner circumferential surface of the opening 8961 of the spur gear 896.

With the selector rod 827 so positioned, the main motor drive component 8310 is then actuated in a reverse direction from that described above. Specifically, an operator may move the finger-actuated control button 8107. The corresponding Hall-effect switch that is located immediately proximal to the control button 8107 senses the movement of the magnet in the control button 8107 and generates an appropriate signal that is sent to, and received by, the main motor drive component 8310. The main motor drive component 8310 turns the shaft 8311 in response to the received signals. In this example embodiment, the main motor drive component 8310 may turn the shaft 8311 in a counter-clockwise direction.

Since the distal end of the shaft 8311 is keyed to the non-circular opening 8401 of the spur gear 840, counter-clockwise rotation of the shaft 8311 causes the spur gear 840 to rotate in a counter-clockwise direction. Also, because the gear teeth on the outer circumference of the spur gear 840 are meshingly engaged with the gear teeth on the outer circumference of the spur gear 839, counter-clockwise rotation of the spur gear 840 causes the spur gear 839 to rotate in a clockwise direction. As set forth above, the proximal portion 8272 of the selector rod 827 is keyed within the non-circular opening 8391 of the spur gear 839, such that clockwise rotation of the spur gear 839 causes the selector rod 827 to rotate in a clockwise direction. Also, because the selector rod 827 is in an axial position in which the nubs 828 of the selector rod 827 are positioned within the longitudinal slots located on the inner circumferential surface of the opening 8961 of the spur gear 896, clockwise rotation of the selector rod 827 causes the spur gear 896 to rotate in a clockwise direction.

Because the gear teeth on the outer circumference of the spur gear 896 are meshingly engaged with the gear teeth on the outer circumference of the spur gear 895, clockwise rotation of the spur gear 896 causes the spur gear 895 to rotate in a counter-clockwise direction. The non-circular opening 8951 of the spur gear 895 is keyed to a shaft, such as the shaft 527 illustrated in, e.g., FIG. 4(*d*), such that counter-clockwise rotation of the spur gear 895 causes the first jaw 850 to move, e.g., be closed, relative to the second jaw 880) in the manner described hereinabove or in any other manner, thereby clamping the section of tissue between the first and second jaws 850, 880.

Once a section of tissue has been clamped between the first and second jaws 850, 880, the section of tissue may be cut and/or stapled. It should be recognized that, while the present invention is illustrated as using both cutting and stapling elements, the surgical device 800 may employ only one such element, or else may employ a different type of surgical instrument.

Before the surgical device 800 is inserted into a patient's body, a staple cartridge 578 is provided within the second jaw 880. In an embodiment, the surgical device 800 is a single-use device, in which the staple cartridge is integral to the second jaw 880. Alternatively, the surgical device 800 may have a replaceable staple cartridge, e.g., replaceable staple cartridge 600 as illustrated in FIG. 4(*e*), thereby permitting the surgical device 800 to be used numerous times with different staple cartridges. In this embodiment, if the surgical device 800 is being used for the first time, the staple cartridge 600 may be pre-installed during manufacture and assembly of the surgical device 800, or else may be installed by the user just prior to using the surgical device 800. If the surgical device 800 is being used for the second or more time, the staple cartridge 600 may be installed by the user just prior to using the surgical device 800. When the staple cartridge 600 is inserted into the second jaw 880, the distal end of the firing shaft 557 is received within the proximally-facing opening 605*d* of the wedge driver 605.

With the staple cartridge 600 installed within the second jaw 80 of the surgical device 800, the surgical device 800 may be operated such that the function selector module 8210 is moved to a firing function position. As set forth above, in this firing function position, the selector rod 827 is positioned such that the nubs 828 of the selector rod 827 are positioned within the longitudinal slots located on the inner circumferential surface of the opening 8371 of the spur gear 837.

With the selector rod 827 so positioned, the main motor drive component 8310 is then actuated. Specifically, an operator may again move the finger-actuated control button 8107. The corresponding Hall-effect switch that is located immediately proximal to the control button 8107 senses the movement of the magnet in the control button 8107 and generates an appropriate signal that is sent to, and received by, the main motor drive component 8310. The main motor drive component 8310 turns the shaft 8311 in response to the received signals. In this example embodiment, the main motor drive component 8310 may turn the shaft 8311 in a counter-clockwise direction.

Since the distal end of the shaft 8311 is keyed to the non-circular opening 8401 of the spur gear 840, counter-clockwise rotation of the shaft 8311 causes the spur gear 840 to rotate in a counter-clockwise direction. Also, because the gear teeth on the outer circumference of the spur gear 840 are meshingly engaged with the gear teeth on the outer circumference of the spur gear 839, counter-clockwise rotation of the spur gear 840 causes the spur gear 839 to rotate in a clockwise direction. As set forth above, the proximal portion 8272 of the selector rod 827 is keyed within the non-circular opening 8391 of the spur gear 839, such that clockwise rotation of the spur gear 839 causes the selector rod 827 to rotate in a clockwise direction. Also, because the selector rod 827 is in an axial position in which the nubs 828 of the selector rod 827 are positioned within the longitudinal slots located on the inner circumferential surface of the opening 8371 of the spur gear 837, clockwise rotation of the selector rod 827 causes the spur gear 837 to rotate in a clockwise direction.

Because the gear teeth on the outer circumference of the spur gear 837 are meshingly engaged with the gear teeth on the outer circumference of the spur gear 834, clockwise rotation of the spur gear 837 causes the spur gear 834 to rotate in a counter-clockwise direction. The non-circular opening 8341 of the spur gear 834 is keyed to a shaft, such as the shaft 529 illustrated in, e.g., FIG. 4(*d*), such that counter-clockwise rotation of the spur gear 834 causes the cutting and/or stapling of the tissue in the manner described hereinabove or in any other manner, e.g., by driving a staple pushing element and/or cutting blade through the section of tissue.

Once the section of tissue is cut and/or stapled, the surgical device 800 may be employed to return the wedge 2603 and the blade 51 to their initial positions. This may be particularly desirable when the surgical device 800 employs replaceable staple cartridges, e.g., replaceable staple cartridge 600 as illustrated in FIG. 4(*e*), thereby permitting the surgical device 800 to be used numerous times with different staple cartridges. Once the wedge 2603 and the blade 51 have been moved to their initial positions, the surgical device 800 may be used for a second or more time. To do so, the user may remove the spent staple cartridge 600 and insert in the surgical device 800 a new staple cartridge 600, the distal end of the firing shaft 557 being received within the proximally-facing opening 2605*d* of the wedge driver 2605 of the new staple cartridge 2600. Of course, it should be recognized that this step of returning the wedge 2603 and the blade 51 to their initial positions may be performed either prior to, or subsequent to, removal of the surgical device 800 from the patient's body.

In order to return the wedge 2603 and the blade 51 to their initial positions, the function selector module 8210 may remain in the firing function position. As set forth above, in this firing function position, the selector rod 827 is positioned such that the nubs 828 of the selector rod 827 are positioned within the longitudinal slots located on the inner circumferential surface of the opening 8371 of the spur gear 837.

With the selector rod 827 so positioned, the main motor drive component 8310 is then actuated in a reverse direction as described above. Specifically, an operator may again move the finger-actuated control button 8107. The corresponding Hall-effect switch that is located immediately proximal to the control button 8107 senses the movement of the magnet in the control button 8107 and generates an appropriate signal that is sent to, and received by, the main motor drive component 8310. The main motor drive component 8310 turns the shaft 8311 in response to the received signals. In this example embodiment, the main motor drive component 8310 may turn the shaft 8311 in a clockwise direction.

Since the distal end of the shaft 8311 is keyed to the non-circular opening 8401 of the spur gear 840, clockwise rotation of the shaft 8311 causes the spur gear 840 to rotate in a clockwise direction. Also, because the gear teeth on the outer circumference of the spur gear 840 are meshingly engaged with the gear teeth on the outer circumference of the spur gear 839, clockwise rotation of the spur gear 840 causes the spur gear 839 to rotate in a counter-clockwise direction. As set forth above, the proximal portion 8272 of the selector rod 827 is keyed within the non-circular opening 8391 of the spur gear 839, such that counter-clockwise rotation of the spur gear 839 causes the selector rod 827 to rotate in a counter-clockwise direction. Also, because the selector rod 827 is in an axial position in which the nubs 828 of the selector rod 827 are positioned within the longitudinal slots located on the inner circumferential surface of the opening 8371 of the spur gear 837, counter-clockwise rotation of the selector rod 827 causes the spur gear 837 to rotate in a counter-clockwise direction.

Because the gear teeth on the outer circumference of the spur gear 837 are meshingly engaged with the gear teeth on the outer circumference of the spur gear 834, counter-clockwise rotation of the spur gear 837 causes the spur gear 834 to rotate in a clockwise direction. The non-circular opening 8341 of the spur gear 834 is keyed to a shaft, such as the shaft 529 illustrated in, e.g., FIG. 4(*d*), such that clockwise rotation of the spur gear 834 causes the cutting and/or stapling elements, e.g., the wedge 2603 and the blade 51, to be returned to their initial positions in the manner described hereinabove or in any other manner.

Once the wedge 2603 and the blade 51 to their initial positions, the surgical device 800 may be employed to move the jaw portion 811*a* relative to the shaft portion 811*b*, e.g., to pivot the jaw portion 811*a* about axis B relative to the shaft portion 811*b*, back to its initial aligned positioned for the purposes of easing the removal of the surgical device from the incision of the patient. In order to perform this function, the surgical device 800 may be operated such that the function selector module 8210 is moved back to the articulation function position. As set forth above, in this articulation function position, the function selector module 8210 causes engagement of the main drive shaft 8311 of the main motor drive component 8310 with appropriate gears of the selector gearbox assembly 850, as set forth more fully below.

Generally, the function selector module 8210 is actuated such that the shaft 8211 moves the selector rod 827 back to the articulation function position in which the nubs 828 of the selector rod 827 are positioned within the longitudinal slots located on the inner circumferential surface of the opening 8361 of the spur gear 836.

With the selector rod 827 so positioned, the main motor drive component is then actuated in the reverse direction from that described above. Specifically, an operator may move the finger-actuated rocker device 8117 in a second direction. The corresponding Hall-effect switch that is located immediately proximal to the rocker device 8117 senses the movement of the magnet in the rocker device 3117 and generates an appropriate signal that is sent to, and received by, the main motor drive component 8310. The main motor drive component 8310 turns the shafts 8311 in response to the received signals. In an example embodiment, the main motor drive component 8310 may turn the shaft 8311 in a counter-clockwise direction. The distal end of the shaft 8311 is keyed to the non-circular opening 8401 of the spur gear 840, such that counter-clockwise rotation of the shaft 8311 causes the spur gear 840 to rotate in a counter-clockwise direction. Because the gear teeth on the outer circumference of the spur gear 840 are meshingly engaged with the gear teeth on the outer circumference of the spur gear 839, counter-clockwise rotation of the spur gear 840 causes the spur gear 839 to rotate in a clockwise direction. As set forth above, the proximal portion 8272 of the selector rod 827 is keyed within the non-circular opening 8391 of the spur gear 839, such that clockwise rotation of the spur gear 839 causes the selector rod 827 to rotate in a clockwise direction. Also, because the selector rod 827 is in an axial position in which the nubs 828 of the selector rod 827 are positioned within the longitudinal slots located on the inner circumferential surface of the opening 8361 of the spur gear 836, clockwise rotation of the selector rod 827 causes the spur gear 836 to rotate in a clockwise direction.

Because the gear teeth on the outer circumference of the spur gear 836 are meshingly engaged with the gear teeth on the outer circumference of the spur gear 838, clockwise rotation of the spur gear 836 causes the spur gear 838 to rotate in a counter-clockwise direction. The non-circular opening 8381 of the spur gear 838 is keyed to a shaft, such as the shaft 525 illustrated in, e.g., FIG. 4(*d*), such that counter-clockwise rotation of the spur gear 838 causes articulation of the jaw portion 811*a* relative to the shaft portion 811*b* about axis B in the second, e.g., clockwise direction (when viewed from above) in the manner described hereinabove or in any other manner. Of course, the movement, e.g., articulation, in the opposite direction may also be accomplished by reversing the direction in which the above-described gears are caused to rotate.

Once the longitudinal axes of the jaw portion 811*a* and the shaft portion 811*b* have been aligned, the surgical device 800 may be employed to return the shaft portion 811*b* to its initial position relative to the handle 8103, e.g., by rotating the shaft portion 811*b* relative to the handle 8103 about the longitudinal axis D of the handle 8103 until the shaft portion 811*b* and the handle 8103 are in their initial, e.g., aligned, positions relative to each other. Again, this may be particularly desirable when the surgical device 800 employs replaceable staple cartridges, e.g., replaceable staple cartridge 600 as illustrated in FIG. 4(*e*), so as to return the surgical device 800 into a condition which permits it to be used numerous times with different staple cartridges. Once the shaft portion 811*b* has been rotated back to its initial position relative to the handle 8103, the surgical device 800 may be used for a second or more time. Of course, it should be recognized that this particular step may be performed either prior to, or subsequent to, removal of the surgical device 800 from the patient's body.

Those skilled in the art will appreciate that numerous modifications of the exemplary embodiment described hereinabove may be made without departing from the spirit and scope of the present invention. Although exemplary embodiments of the present invention have been described and disclosed in detail herein, it should be understood that this invention is in no sense limited thereby.

What is claimed is:

1. A surgical device, comprising:
   a handle;
   a shaft having a proximal end portion coupled to the handle and a distal end portion and defining a longitudinal axis;
   a jaw portion pivotably coupled to the distal end portion of the shaft, the jaw portion including:
     a first jaw member;
     a second jaw member; and
     a cutting and stapling element;
   a first rotatable drive shaft;
   a second rotatable drive shaft;
   a first driver;
   a second driver;
   a third driver; and
   a function selector module movable by the first rotatable drive shaft between a first functional position in which the second rotatable drive shaft engages the first driver, a second functional position in which the second rotatable drive shaft engages the second driver, and a third functional position in which the second rotatable drive shaft engages the third driver configured to pivot the first jaw member relative to the second jaw member.

2. The surgical device according to claim 1, further comprising:
   a first motor coupled to the first rotatable drive shaft, the first motor configured to rotate the first rotatable drive shaft.

3. The surgical device according to claim 2, further comprising:
   a second motor coupled to the second rotatable drive shaft, the second motor configured to rotate the second rotatable drive shaft.

4. The surgical device according to claim 1, wherein the first driver is configured to rotate the shaft about the longitudinal axis defined by the shaft relative to the handle.

5. The surgical device according to claim 1, wherein the second driver is configured to pivot the jaw portion about a pivot axis perpendicular to the longitudinal axis.

6. The surgical device according to claim 1, further comprising:
   a fourth driver, wherein the function selector module movable by the first rotatable drive shaft to a fourth functional position in which the second rotatable drive shaft engages the fourth driver configured to move the cutting and stapling element.

7. A surgical device, comprising:
   a handle;
   a shaft having a proximal end portion coupled to the handle and a distal end portion and defining a longitudinal axis;
   a jaw portion pivotably coupled to the distal end portion of the shaft, the jaw portion including:
     a first jaw member;
     a second jaw member; and
     a cutting and stapling element
   a rotatable drive shaft;
   a plurality of drivers, wherein a first driver of the plurality of drivers is configured to pivot the first jaw member relative to the second jaw member; and a function selector module movable between a plurality of positions in which the rotatable drive shaft engages one of the plurality of drivers.

8. The surgical device according to claim 7, further comprising:
a first motor configured to move the function selector module.

9. The surgical device according to claim 8, further comprising:
a second motor coupled to the rotatable drive shaft, the second motor configured to rotate the rotatable drive shaft.

10. The surgical device according to claim 7, wherein a second driver of the plurality of drivers is configured to rotate the shaft about the longitudinal axis defined by the shaft relative to the handle.

11. The surgical device according to claim 7, wherein a third driver of the plurality of drivers is configured to pivot the jaw portion about a pivot axis perpendicular to the longitudinal axis.

12. The surgical device according to claim 7, wherein a fourth driver of the plurality of drivers is configured to move the cutting and stapling element.

* * * * *